US011638540B2

(12) United States Patent
Halac et al.

(10) Patent No.: US 11,638,540 B2
(45) Date of Patent: May 2, 2023

(54) SYSTEMS AND METHOD FOR ACTIVATING ANALYTE SENSOR ELECTRONICS

(71) Applicant: DexCom, Inc., San Diego, CA (US)

(72) Inventors: Jason Halac, San Diego, CA (US); Sebastian Bohm, San Diego, CA (US); Vincent Peter Crabtree, San Diego, CA (US); David DeRenzy, San Diego, CA (US); Mark S. Dervaes, Carlsbad, CA (US); Nicholas Kalfas, San Diego, CA (US); Zebediah L. McDaniel, San Diego, CA (US); Michael Levozier Moore, Poway, CA (US); Todd Andrew Newhouse, San Diego, CA (US); Michael A. Ploof, Del Mar, CA (US); Stephen Alan Reichert, San Diego, CA (US); Peter C. Simpson, Cardiff, CA (US); Alexander Leroy Teeter, Poway, CA (US); Rodolfo Garcia, Pembroke Pines, FL (US); Jaroslaw Piotrowiak, San Diego, CA (US); Thomas George O'Connell, San Diego, CA (US); Arlene G. Doria, Chula Vista, CA (US)

(73) Assignee: Dexcom, Inc., San Diego, CA (US)

(*) Notice: Subject to any disclaimer, the term of this patent is extended or adjusted under 35 U.S.C. 154(b) by 368 days.

(21) Appl. No.: 16/400,873

(22) Filed: May 1, 2019

(65) Prior Publication Data

US 2019/0336053 A1 Nov. 7, 2019

Related U.S. Application Data

(60) Provisional application No. 62/666,554, filed on May 3, 2018.

(51) Int. Cl.
A61B 5/145 (2006.01)
A61B 5/1455 (2006.01)
(Continued)

(52) U.S. Cl.
CPC ........ *A61B 5/14532* (2013.01); *A61B 5/0031* (2013.01); *A61B 5/1455* (2013.01);
(Continued)

(58) Field of Classification Search
CPC .............. A61B 5/14532; A61B 5/0031; A61B 5/14546; A61B 5/6847; A61B 5/14503;
(Continued)

(56) References Cited

U.S. PATENT DOCUMENTS 6,001,067 A 12/1999 Shults et al.
6,424,847 B1 7/2002 Mastrototaro et al.
(Continued)

FOREIGN PATENT DOCUMENTS

EP 1075209 A1 2/2001

OTHER PUBLICATIONS

International Search Report and Written Opinion dated Sep. 5, 2019 for Application No. PCT/US2019/030279.
(Continued)

*Primary Examiner* — Matthew Kremer
*Assistant Examiner* — Kyle W. Kretzer
(74) *Attorney, Agent, or Firm* — Patterson + Sheridan, LLP

(57) ABSTRACT

Various analyte sensor systems for controlling activation of analyte sensor electronics circuitry are provided. Related methods for controlling analyte sensor electronics circuitry are also provided. Various analyte sensor systems for monitoring an analyte in a host are also provided. Various circuits for controlling activation of an analyte sensor system are also provided. Analyte sensor systems utilizing a state
(Continued)

machine having a plurality of states for collecting a plurality of digital counts and waking a controller responsive to a wake up signal are also provided. Related methods for such analyte sensor systems are also provided. Systems for controlling activation of analyte sensor electronics circuitry utilizing a magnetic sensor are further provided. One or more display device configured to display one or more analyte concentration values are also provided.

20 Claims, 22 Drawing Sheets

(51) Int. Cl.
*A61B 5/00* (2006.01)
*H04Q 9/00* (2006.01)
*H04W 76/14* (2018.01)
(52) U.S. Cl.
CPC ...... *A61B 5/14503* (2013.01); *A61B 5/14546* (2013.01); *A61B 5/6847* (2013.01); *A61B 5/6849* (2013.01); *H04Q 9/00* (2013.01); *A61B 2560/0209* (2013.01); *A61B 2560/029* (2013.01); *A61B 2560/0257* (2013.01); *A61B 2562/0257* (2013.01); *H04Q 2209/40* (2013.01); *H04Q 2209/883* (2013.01); *H04W 76/14* (2018.02)
(58) Field of Classification Search
CPC .......... A61B 5/1455; A61B 2560/0257; A61B 2560/029; A61B 2560/0266; A61B 2562/0257; A61B 2560/0209; A61B 5/6849; A61B 5/145; H04Q 9/00; H04Q 2209/40; H04Q 2209/883; H04Q 2209/43; H04Q 2209/823; H04W 76/14
See application file for complete search history.

(56) References Cited

U.S. PATENT DOCUMENTS

| | | | |
|---|---|---|---|
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,565,509 | B1 | 5/2003 | Say et al. |
| 6,579,690 | B1 | 6/2003 | Bonnecaze et al. |
| 6,931,327 | B2 | 8/2005 | Goode, Jr. et al. |
| 7,310,544 | B2 | 12/2007 | Brister et al. |
| 9,801,575 | B2 | 10/2017 | Böhm et al. |
| 10,405,800 | B2 * | 9/2019 | Ganton ................ A61B 5/0006 |
| 10,656,695 | B2 * | 5/2020 | Cronin ................ A61B 5/6804 |
| 2005/0027463 | A1 | 2/2005 | Goode, Jr. et al. |
| 2005/0043598 | A1 | 2/2005 | Goode, Jr. et al. |
| 2005/0154271 | A1 | 7/2005 | Rasdal et al. |
| 2005/0192557 | A1 | 9/2005 | Brauker et al. |
| 2005/0203360 | A1 | 9/2005 | Brauker et al. |
| 2006/0020187 | A1 | 1/2006 | Brister et al. |
| 2006/0222566 | A1 | 10/2006 | Brauker et al. |
| 2006/0258929 | A1 | 11/2006 | Goode, Jr. et al. |
| 2007/0016381 | A1 | 1/2007 | Kamath et al. |
| 2007/0027385 | A1 | 2/2007 | Brister et al. |
| 2007/0032706 | A1 | 2/2007 | Kamath et al. |
| 2007/0197890 | A1 | 8/2007 | Boock et al. |
| 2007/0203966 | A1 | 8/2007 | Brauker et al. |
| 2007/0208245 | A1 | 9/2007 | Brauker et al. |
| 2008/0033254 | A1 | 2/2008 | Kamath et al. |
| 2008/0108942 | A1 | 5/2008 | Brister et al. |
| 2008/0119703 | A1 | 5/2008 | Brister et al. |
| 2009/0146826 | A1 | 6/2009 | Gofman et al. |
| 2009/0318792 | A1 | 12/2009 | Fennell et al. |
| 2012/0078071 | A1 * | 3/2012 | Bohm ................ A61B 5/14532 600/345 |
| 2012/0172691 | A1 | 7/2012 | Brauker et al. |
| 2012/0265035 | A1 * | 10/2012 | Bohm ................ G01N 27/3274 600/309 |
| 2013/0137946 | A1 | 5/2013 | Geske et al. |
| 2013/0217979 | A1 * | 8/2013 | Blackadar ............ A61B 5/1123 600/301 |
| 2014/0266776 | A1 * | 9/2014 | Miller .................. A61B 5/0015 340/870.01 |
| 2017/0172472 | A1 * | 6/2017 | Wedekind .............. G16H 40/67 |
| 2017/0172473 | A1 * | 6/2017 | Wedekind ............ A61B 5/0004 |
| 2019/0129491 | A1 * | 5/2019 | Biederman, III ....... G06F 1/163 |
| 2019/0342637 | A1 | 11/2019 | Halac et al. |

OTHER PUBLICATIONS

Office Action from European Patent Application No. 19796938.9, dated Dec. 10, 2020, 3 pages.
Extended European Search Report for Application No. 19796938.9, dated Dec. 9, 2021, 12 pages.

* cited by examiner

SYSTEMS AND METHOD FOR ACTIVATING ANALYTE SENSOR ELECTRONICS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/666,554, filed May 3, 2018. The aforementioned application is incorporated by reference herein in its entirety, and is hereby expressly made a part of this specification.

TECHNICAL FIELD

The present developments relate generally to medical devices such as analyte sensors, and more particularly, but not by way of limitation, to systems, devices, and methods related to activating analyte sensor electronics on such medical devices.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display. The transmission to wireless display devices can be wireless. The remote device can then provide the user with information about the user's blood glucose levels. Because systems using such implantable sensors can provide more up to date information to users, they may reduce the risk of a user failing to regulate the user's blood glucose levels. Nevertheless, such systems typically still rely on the user to take action in order to regulate the user's blood glucose levels, for example, by making an injection.

Such systems may typically include a glucose sensor implantable into a host and sensor electronics circuitry for processing and communicating glucose related information. In such systems, however, the sensor and the sensor electronics circuitry are usually designed to be connected for the first time by a user or host after the sensor has been implanted into the user. Consequently, a pre-connected system can potentially reduce the amount of user interaction involved with deploying an analyte sensor system.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

In view of the above characteristics associated with some systems, there exists a need for an analyte sensor system in which an analyte sensor and analyte sensor electronics circuitry are configured to be electrically and mechanically coupled to each other before the analyte sensor is implanted into the user or host. The present disclosure relates generally to controlling activation of sensor electronics for the wireless communication of analyte data gathered using an analyte sensor system. More particularly, the present disclosure is directed to systems, methods, apparatuses, and devices, for using multiple techniques for controlling such activation in an analyte sensor system in which the analyte sensor is connected both electrically and mechanically to analyte sensor electronics circuitry before the analyte sensor is implanted in the host.

There are numerous advantages associated with the systems, methods, devices, and other aspects and embodiments of the present disclosure. For example, an analyte sensor system in which the analyte sensor is configured to be connected to the analyte sensor electronics circuitry before implantation may not need a lot of user interaction, and may be smaller, simpler, more elegant, and/or cheaper, and may have less sealing, deployment, and connection issues. For example, analyte sensor connection, alignment, and retention, and isolation issues related to analyte sensor connection at the time of transcutaneous implantation may be avoided. By way of further example, in systems not designed to be pre-connected, a seal may need to be made between the analyte sensor electronics circuitry and the analyte sensor and/or housing thereof when the analyte sensor and the analyte sensor electronics circuitry are brought together in the field. But, in a pre-connected system, this sealing can be accomplished during system manufacturing. Hence, faults that may occur as a result of analyte sensor insertion can be avoided. Another example advantage of the pre-connected system is that it may be advantageous for the analyte sensor system to enter an active state to capture analyte measurement values near the time the analyte sensor is implanted into the user. This can enable an analyte processing algorithm to more accurately assess the time of sensor implantation and thereby more accurately process sensor signal analyte values.

There can also be a number of challenges associated with implementing a pre-connected analyte sensor system. For example, in non-pre-connected systems, monitoring the analyte sensor electronics circuitry for electrical signals indicative of an analyte sensor being present in the circuit may be used to activate the analyte sensor system. But, in a pre-connected system, such signals may be subject to noise, which may lead to false triggering/activation of the system. Additionally, monitoring of the analyte sensor prior to implantation may cause unwanted changes to the analyte sensor (e.g., deviation from calibration values). Therefore, monitoring the analyte sensor electronics for only analyte sensor signals may in certain instances not be well suited as a primary or sole means for activation purposes.

Alternative and/or additional means of activating the analyte sensor system may thus be employed. Such means, however, should be robust to false wake-up events, should maintain accurate analyte sensor calibration, should not consume significant power, and should enable sufficiently rapid wake-up of the analyte sensor system. Additionally, pre-connected systems should provide improved user experience, for example, by reducing and/or eliminating user steps associated with connection, and/or reducing and/or eliminating the possibility of combining incompatible sensors and electronics. Furthermore, and for example, pre-connected systems and solutions may facilitate initiation of connections (e.g., wireless connections) faster in closed-loop systems (e.g., automated insulin delivery systems and related or similar systems and applications) that may lead to reduced gaps in the analyte data. Also, in a healthcare provider scenario (e.g., in a doctor's or other medical office) or the like, the amount of time involved with setting up such systems (e.g., including time for sensor implantation into a user's body and/or for activating or establishing operation of analyte sensor electronics) may be substantially reduced.

Embodiments of the present disclosure overcome these challenges and provide the above described advantages by using multiple methods of detecting and confirming conditions for activating analyte sensor electronics circuitry. By using one or more verification methods, embodiments of the present disclosure provide a system that is more robust to false wake-ups, thus saving power and providing better overall reliability as well as providing the other advantages described above. To implement a robust wake-up or activation procedure and to avoid false wake-up events, according to embodiments of the present disclosure, multiple indicators of analyte sensor insertion can be used to trigger analyte sensor electronics circuitry to exit a lower power state. In many embodiments, the system is designed to largely avoid changing the properties of the analyte sensor, to be robust to signal noise that may be experienced prior to analyte sensor implantation (e.g., that may result from humidity, temperature, vibration, etc.), and to operate in a manner feasible for a low power battery-operated device.

In terms of the multiple techniques that may be used for detecting activation events for the analyte sensor electronics circuitry, such techniques may generally be divided into those that utilize primary signals and those that utilize secondary signals. As referred to herein, primary signals may generally relate to signals pertaining to, correlating to, derived from, characterizing, and/or describing analyte information as derived from a host who is using the analyte sensor. As referred to herein, secondary signals may generally relate to information gathered using the analyte sensor system, where the gathered information is information other than the primary signal(s) (e.g., the gathered information is not information used in a primary signal capacity to describe a relationship between the signal and the analyte information). Secondary signals or information may be gathered using the analyte sensor (e.g., one or more electrodes) and/or other means. Such other means may include circuits or components internal to the analyte sensor system or external thereto, as described in further detail herein. Additionally, secondary signals or information may be gathered using the analyte sensor system and/or external components alone, or in conjunction with user interaction.

Combining multiple techniques that may be used for detecting activation events for the analyte sensor electronics circuitry, for example, where one technique can be used to check another technique that may be subject to noise or false triggers, for example, where one or more primary signal can be used to check one or more secondary signals, can increase system robustness to false wake ups. In some instances, a primary signal (e.g., analyte value or signal that may be representative thereof, such as a voltage, current, count, or other signal) can be used in combination with a secondary signal that may be gathered/derived using the analyte sensor signal (e.g., analyte sensor impedance, capacitance, etc.). In some instances, the primary signal can be used in combination with one or more secondary signals that are not derived/gathered using means other than or in addition to the analyte sensor. In embodiments, primary signal information can be combined with secondary signal information, which may be or include one or more non-analyte sensor signals or information. In embodiments, the analyte sensor system can use primary signal(s) and/or secondary signal(s) gathered/derived using the analyte sensor, and one or more signals or information gathered/derived using means other than the analyte sensor (e.g., an accelerometer signal or other technique as described herein) and can compare the foregoing at one or more time periods for purposes of activating the analyte sensor system. In this manner, embodiments of the present disclosure can more accurately assess activation times, and/or better avoid and/or reduce false wake ups in a pre-connected analyte sensor system, while maintaining a battery efficient lower power mode and robust sensor performance.

A first aspect of the present disclosure includes a system for controlling activation of analyte sensor electronics circuitry. The system includes an analyte sensor that is electrically and mechanically coupled to analyte sensor electronics circuitry prior to transitioning the system into an operational state. The analyte sensor electronics circuitry is adapted to perform a number of operations. One such operation is to trigger an indication for the system to exit a lower power state and transition into the operational state. The indication is triggered based on a threshold value associated with deployment of the system. Another such operation is to, responsive to the indication, generate a control signal operable to cause the analyte sensor to gather information related to a level of an analyte in a host. Yet another such operation is to generate a comparison between the information related to the level of the analyte in the host and a condition. The system exits the lower power state and transitions into the operational mode based on the indication being triggered and the comparison indicating that the level of the analyte in the host satisfies the condition.

In certain implementations of the first aspect, which may be generally applicable but are also particularly applicable in connection with any other implementation of the first aspect, the analyte sensor electronics circuitry is further adapted to cause the system to trigger the indication in response to the threshold value being satisfied for at least a predetermined amount of time.

In certain implementations of the first aspect, which may be generally applicable but are also particularly applicable in connection with any other implementation of the first aspect, the indication is a signal generated using one or more of an activation detection circuit and an activation detection component that are adapted to detect one or more of insertion of the analyte sensor into the host and deployment of the system.

In certain implementations of the first aspect, which may be generally applicable but are also particularly applicable in connection with any other implementation of the first aspect, the control signal is a signal operable to cause a potentiostat to apply a voltage bias to the analyte sensor and thereby cause the analyte sensor to gather the information related to the level of the analyte in the host.

In certain implementations of the first aspect, which may be generally applicable but are also particularly applicable in connection with any other implementation of the first aspect, after the system transitions to the operational state, the system continues gathering the information related to the level of the analyte in the host and communicates the information to one or more display devices or one or more partner devices.

In certain implementations of the first aspect, which may be generally applicable but are also particularly applicable in connection with any other implementation of the first aspect, the threshold value is related to a level of a known analyte typically present in a human host.

In certain implementations of the first aspect, which may be generally applicable but are also particularly applicable in connection with any other implementation of the first aspect, the indication is generated using one or more of (1) a detected proximity between the analyte sensor electronics circuitry and a reference object; (2) a temperature monitored using the analyte sensor electronics circuitry; (3) an output of an accelerometer of the analyte sensor electronics circuitry; (4) a response generated using wireless signaling transmitted or received by the analyte sensor electronics; (5) a detected change in air pressure measured by the analyte sensor electronics circuitry; (6) audio information monitored by the analyte sensor electronics circuitry; (7) a signal generated by the analyte sensor electronics circuitry in response to photons detected by the analyte sensor electronics circuitry; (8) a conductivity measured between two terminals of the analyte sensor electronics circuitry; (9) a mechanical switch located on or within a housing of the analyte sensor electronics circuitry; (10) a component adapted to change a connection between two conductive elements of the analyte sensor electronics circuitry, in response to movement of the component; and (11) a measured strain.

In certain implementations of the first aspect, which may be generally applicable but are also particularly applicable in connection with any other implementation of the first aspect, the system exits the lower power state based on the determination that the level of analyte in a host exceeds a threshold value.

In certain implementations of the first aspect, which may be generally applicable but are also particularly applicable in connection with any other implementation of the first aspect, the analyte sensor electronics circuitry is further adapted to cause the system to trigger the indication in response to a condition being satisfied for programmed intervals of time.

In certain implementations of the first aspect, which may be generally applicable but are also particularly applicable in connection with any other implementation of the first aspect, the information related to the level of the analyte in the host is used to generate detected counts. Further, the condition includes a threshold characteristic for the counts. If the comparison indicates that the detected counts meet the threshold, the system exits the lower power state and enters the operational mode.

A second aspect of the present disclosure includes a method for controlling analyte sensor electronics circuitry. The method includes the analyte sensor electronics circuitry obtaining a first signal generated using one or more of an analyte sensor and a secondary sensor. The method further includes determining whether a first condition is met based on the first signal obtained by the analyte sensor electronics circuitry. The method also includes, responsive to the first condition being met, the analyte sensor electronics circuitry activating an analyte measurement circuit. Additionally, the method includes the analyte measurement circuit using the analyte sensor to gather information related to an analyte value in a host. The analyte sensor was coupled to the analyte sensor electronics before the analyte sensor was implanted into the host. The method also includes the analyte sensor electronics circuitry determining whether the information related to the analyte value in the host meets a second condition.

Additionally, the method according to the second aspect includes, responsive to the analyte sensor electronics circuitry determining that the information related to the analyte value in the host meets the second condition, the sensor electronics circuitry exiting the lower power consumption mode. Alternatively, the method includes, responsive to the analyte sensor electronics circuitry determining that the information related to the analyte value in the host does not meet the second condition, the analyte sensor electronics circuitry remaining in the lower power consumption mode and obtaining a second electrical signal that indicates whether the first condition has been met.

In certain implementations of the second aspect, which may be generally applicable but are also particularly applicable in connection with any other implementation of the second aspect, the second condition is met if the information related to the analyte value indicates that the level of the analyte value in the host satisfies a threshold value.

In certain implementations of the second aspect, which may be generally applicable but are also particularly applicable in connection with any other implementation of the second aspect, the first condition represents a proximity of the analyte sensor electronics circuitry to a reference point.

In certain implementations of the second aspect, which may be generally applicable but are also particularly applicable in connection with any other implementation of the second aspect, the first condition represents a level of acceleration detected using an accelerometer.

In certain implementations of the second aspect, which may be generally applicable but are also particularly applicable in connection with any other implementation of the second aspect, the first condition relates to one or more electrical characteristics measured for the analyte sensor.

A third aspect of the present disclosure includes a system for monitoring an analyte in a host. The system includes an analyte sensor. The analyte sensor includes one or more electrodes that are adapted to gather information related to a level of the analyte in the host. The system also includes sensor electronics circuitry mechanically and electrically coupled to the analyte sensor before the analyte sensor is implanted into the host. The sensor electronics circuitry is adapted to generate a secondary indicator using a first condition and a measurement of an electrical signal passed between at least two of the one or more electrodes. The sensor electronics circuitry is further adapted to cause the system to enter the active state in response to the sensor electronics circuitry generating a confirmation of the secondary indicator using a second condition and the information related to the level of the analyte in the host.

In certain implementations of the third aspect, which may be generally applicable but are also particularly applicable in connection with any other implementation of the third aspect, the sensor electronics circuitry is further adapted to use the measurement of the electrical signal passed between the at least two of the one or more electrodes to determine one or more of an impedance, capacitance, voltage, and current associated with the one or more electrodes.

A fourth aspect of the present disclosure includes a system for monitoring an analyte in a host. The system includes analyte sensor electronics circuitry. The system further includes an analyte sensor that is mechanically and electrically coupled to the analyte sensor electronics circuitry before the analyte sensor is implanted into the host. In addition, the system includes an activation detection circuit coupled to the analyte sensor. The activation detection circuit is adapted to generate a control signal operable to cause the analyte sensor to obtain information related to a level of the analyte in the host. The control signal is generated in response to an electrical signal indicating that a first condition is satisfied. The analyte sensor electronics circuitry is adapted to cause the system to change states if the level of the analyte in the host satisfies a second condition and if the electrical signal indicates that the first condition is satisfied.

In certain implementations of the fourth aspect, which may be generally applicable but are also particularly applicable in connection with any other implementation of the fourth aspect, the indication that the first condition is satisfied is generated using one or more of parameters, inputs, and/or variables. For example, any of the following, alone or in combination, may be used for generating the indication. The indication may be generated using a detected proximity between the analyte sensor electronics circuitry and a reference object. The indication may be generated using a temperature monitored by the analyte sensor electronics circuitry. The indication may be generated using an output of an accelerometer of the analyte sensor electronics circuitry. In embodiments, the indication may be generated using a response generated using wireless signaling transmitted or received by the analyte sensor electronics. Further, the indication may be generated using a detected change in air pressure measured by the analyte sensor electronics circuitry. Audio information that can be monitored by the analyte sensor electronics circuitry may also be used to generate the indication. Additionally, the indication may be generated using a signal generated by the analyte sensor electronics circuitry in response to photons detected by the analyte sensor electronics circuitry. A conductivity measured between two terminals of the analyte sensor electronics circuitry may also be used to generate the indication. In some cases, the indication may be generated using a mechanical switch located on or within a housing of the analyte sensor electronics circuitry. In embodiments, the indication may be generated using a component adapted to change a connection between two conductive elements of the analyte sensor electronics circuitry, in response to movement of the component. The indication can be generated using a measured strain.

A fifth aspect of the present disclosure includes a system for monitoring an analyte in a host. The system includes analyte sensor electronics circuitry. The system further includes an analyte sensor adapted to be coupled to the analyte sensor electronics circuitry before the analyte sensor is implanted into the host. Additionally, the system includes an activation detection circuit coupled to the analyte sensor. The activation detection circuit is adapted to monitor a secondary sensor according to a sampling frequency and to increase the sampling frequency in response to a first event detected using the secondary sensor. The activation detection circuit is further adapted to monitor the secondary sensor according to the increased sampling frequency and to generate a control signal in response to detecting a second event. The control signal is operable to cause the analyte sensor to make a measurement for obtaining information indicative of a level of the analyte in the host when the analyte sensor is implanted in the host. The analyte sensor electronics circuitry is further adapted to cause the system to change states in response to the information indicative of the level of the analyte in the host satisfying a condition, and further in response to the activation detection circuit detecting the second event.

In certain implementations of the fifth aspect, which may be generally applicable but are also particularly applicable in connection with any other implementation of the fifth aspect, the sampling frequency is set according to a classification of one or more of the first event and the second event as determined by an activation detection component.

A sixth aspect of the present disclosure includes a circuit for controlling activation of an analyte sensor system. The circuit includes a detection circuit adapted to indicate whether a signal at an input terminal of the detection circuit meets a condition. The detection circuit is further adapted to trigger the analyte system to exit a lower power state if the detection circuit indicates that the signal meets the condition. The circuit also include a first switch element adapted to control a coupling between the input terminal of the detection circuit and a first terminal of an analyte sensor. The analyte sensor is adapted to gather information related to an analyte level in a host. The circuit further includes a second switch element adapted to control a coupling between the first terminal of the analyte sensor and a first terminal of a potentiostat. The potentiostat is adapted to apply a voltage bias to the analyte sensor that causes the analyte sensor to gather the information related to the level of the analyte in the host. The input terminal of the detection circuit is coupled to a second terminal of the analyte sensor and to a second terminal of the potentiostat. The circuit is adapted to generate additional detectable events for activating the analyte sensor system, including by, at a first time, causing the second switch element to couple the first terminal of the analyte sensor to the first terminal of the potentiostat and the first switch element to decouple the input terminal of the detection circuit from the first terminal of the analyte sensor. At a second time, the circuit is adapted to cause the second switch element to decouple the first terminal of the analyte sensor from the first terminal of the potentiostat and the first switch element to couple the input terminal of the detection circuit to the first terminal of the analyte sensor.

In certain implementations of the sixth aspect, which may be generally applicable but are also particularly applicable in connection with any other implementation of the sixth aspect, the circuit also includes a capacitive element coupled between the input terminal of the detection circuit and a second reference voltage.

In certain implementations of the sixth aspect, which may be generally applicable but are also particularly applicable in connection with any other implementation of the sixth aspect, the second switch element is adapted to couple the input terminal of the detection circuit to the first terminal of the analyte sensor through a resistive element.

In certain implementations of the sixth aspect, which may be generally applicable but are also particularly applicable in connection with any other implementation of the sixth aspect, the circuit further includes a third switch element adapted to couple the input terminal of the detection circuit to the second reference voltage.

In certain implementations of the sixth aspect, which may be generally applicable but are also particularly applicable in connection with any other implementation of the sixth aspect, when the third switch element couples the input terminal of the detection circuit to the second reference voltage, the capacitive element is discharged.

In certain implementations of the sixth aspect, which may be generally applicable but are also particularly applicable in connection with any other implementation of the sixth aspect, a terminal of the third switch element is coupled to a clock that causes the third switch element to periodically couple the input terminal of the detection circuit to the second reference voltage.

In certain implementations of the sixth aspect, which may be generally applicable but are also particularly applicable in connection with any other implementation of the sixth aspect, the first switch element is driven by a common signal and the second switch element is driven by an inverted version of the common signal.

In certain implementations of the sixth aspect, which may be generally applicable but are also particularly applicable in connection with any other implementation of the sixth aspect, the first switch element and the second switch element are driven by a common signal and have opposite polarities.

In certain implementations of the sixth aspect, which may be generally applicable but are also particularly applicable in connection with any other implementation of the sixth aspect, a voltage at the input terminal of the detection circuit is indicative of a current between the first terminal of the analyte sensor and the second terminal of the analyte sensor when the analyte sensor is implanted in a host.

In certain implementations of the sixth aspect, which may be generally applicable but are also particularly applicable in connection with any other implementation of the sixth aspect, a reference terminal of the detection circuit is coupled to a first reference voltage. The detection circuit includes a comparator.

In certain implementations of the sixth aspect, which may be generally applicable but are also particularly applicable in connection with any other implementation of the sixth aspect, the second voltage reference is ground.

In some embodiments, an analyte sensor system is provided. The analyte sensor system includes an analyte sensor. The analyte sensor system includes a state machine configured to cause a first voltage potential to be applied across the analyte sensor during a first sampling state and cause a second voltage potential to be applied across the analyte sensor during a second sampling state. The analyte sensor system includes analyte sensor measurement circuitry configured to generate a first digital count corresponding to a first current flowing through the analyte sensor during the first sampling state based on application of the first voltage potential and generate a second digital count corresponding to a second current flowing through the analyte sensor during the second sampling state based on application of the second voltage potential. The analyte sensor system includes detection circuitry configured to determine a first difference between the second digital count and the first digital count and generate a controller wake up signal responsive to at least the first difference satisfying a threshold value. The analyte sensor system includes a controller configured to enter a lower power state for at least a duration of the first sampling state, the second sampling state and the determination of the first difference and to transition from the lower power state to an operational state responsive to the controller wake up signal. The controller is configured to determine an impedance of the analyte sensor based at least in part on the first difference.

In some embodiments, the state machine is configured to cause initiation of the first voltage potential applied across the analyte sensor during a first delay state that immediately precedes the first sample state, and the analyte sensor measurement circuitry is configured to suspend generation of digital counts during the first delay state.

In some embodiments, the state machine is configured to cause initiation of the second voltage potential applied across the analyte sensor during a second delay state that immediately precedes the second sample state, and the analyte sensor circuitry is configured to suspend generation of digital counts during the second delay state.

In some embodiments, the state machine is configured to cause a zero-voltage potential to be applied across the analyte sensor during a third delay state that follows the second sampling state, and the analyte sensor measurement circuitry is configured to suspend generation of digital counts during the third delay state.

In some embodiments, the detection circuitry includes a first sample buffer configured to store the first digital count. In some embodiments, the detection circuitry includes a differentiator configured to receive the first digital count from the first sample buffer, receive the second digital count from the analyte sensor measurement circuitry, and determine the first difference.

In some embodiments, the detection circuitry includes an accumulator configured to generate a sum of the first difference and at least a second difference between a third digital count and a fourth digital count. The third digital count corresponds to a third current flowing through the analyte sensor during a subsequent instance of the first sampling state and the fourth digital count corresponds to a fourth current flowing through the analyte sensor during a subsequent instance of the second sampling state. In some embodiments, the detection circuitry is configured to generate the controller wake up signal responsive to at least the sum of the first difference and the second difference satisfying the threshold value.

In some embodiments, the controller is configured to define at least one parameter of the state machine before entering the lower power state. In some embodiments, in a first operating mode of the analyte sensor system, the first voltage potential is zero volts and the second voltage potential is greater than the first voltage potential by a predetermined amount, and in a second operating mode of the analyte sensor system, the first voltage potential is the same as a voltage potential applied across the analyte sensor to determine analyte concentrations within the host and the second voltage potential is greater than the first voltage potential by the predetermined amount.

In some embodiments, a method for controlling an analyte sensor system is provided. The method includes utilizing a state machine to cause a first voltage potential to be applied across an analyte sensor during a first sampling state and cause a second voltage potential to be applied across the analyte sensor during a second sampling state. The method includes utilizing analyte sensor measurement circuitry to generate a first digital count corresponding to a first current flowing through the analyte sensor during the first sampling state based on application of the first voltage potential and generate a second digital count corresponding to a second current flowing through the analyte sensor during the second sampling state based on application of the second voltage potential. The method includes utilizing detection circuitry to determine a first difference between the second digital count and the first digital count, and generate a controller wake up signal responsive to at least the first difference satisfying a threshold value. The method includes causing a controller to enter a lower power state for at least a duration of the first sampling state, the second sampling state and the determination of the first difference, transition from the lower power state to an operational state responsive to the controller wake up signal and determine an impedance of the analyte sensor based at least in part on the first difference.

In some embodiments, the method includes initiating application of the first voltage potential across the analyte sensor during a first delay state that immediately precedes the first sample state and suspending generation of digital counts by the analyte sensor measurement circuitry during the first delay state.

In some embodiments, the method includes initiating application of the second voltage potential across the analyte sensor during a second delay state that immediately precedes the second sample state and suspending generation of digital counts by the analyte sensor measurement circuitry during the second delay state.

In some embodiments, the method includes utilizing the state machine to cause a zero-voltage potential to be applied across the analyte sensor during a third delay state that follows the second sample state and suspending generation of digital counts by the analyte sensor measurement circuitry during the third delay state.

In some embodiments, the method includes storing the first digital count in a first sample buffer prior to determining the first difference. In some embodiments, the method includes receiving, by a differentiator, the first digital count from the first sample buffer, receiving, by the differentiator, the second digital count from the analyte sensor measurement circuitry, and utilizing the differentiator to determine the first difference.

In some embodiments, the method includes utilizing an accumulator to generate a sum of the first difference and at least a second difference between a third digital count and a fourth digital count, the third digital count corresponding to a third current flowing through the analyte sensor during a subsequent instance of the first sampling state and the fourth digital count corresponding to a fourth current flowing through the analyte sensor during a subsequent instance of the second sampling state.

In some embodiments, the method includes generating the controller wake up signal responsive to at least the sum of the first difference and the second difference satisfying the threshold value.

In some embodiments, the method includes utilizing the controller to define at least one parameter of the state machine before entering the lower power state.

In some embodiments, in a first operating mode of the analyte sensor system, the first voltage potential is zero volts and the second voltage potential is greater than the first voltage potential by a predetermined amount and, in a second operating mode of the analyte sensor system, the first voltage potential is the same as a voltage potential applied across the analyte sensor to determine analyte concentrations within the host and the second voltage potential is greater than the first voltage potential by the predetermined amount.

In some embodiments, a system for controlling activation of analyte sensor electronics circuitry is provided. The system includes an analyte sensor, a magnetic sensor configured to trigger a wake signal responsive to a magnet being brought sufficiently close to the magnetic sensor, and analyte sensor electronics circuitry configured to exit a lower power state and transition into an operational state responsive to the wake signal and, responsive to transitioning into the operational state, receive an indication of one or more analyte concentration values from the analyte sensor.

In some embodiments, the magnet is disposed on a display device configured to display the one or more analyte concentration values. In some embodiments, the magnetic sensor is configured to trigger the wake signal responsive to the magnet being moved in at least one of a predetermined motion and a predetermined spatial orientation with respect to the magnetic sensor.

In some embodiments, a display device configured to display one or more analyte concentration values is provided. The display device includes a microphone configured to generate one or more audio waveforms of a sound made by an applicator while deploying the analyte sensor system. The display device includes a processor configured to execute an application while the applicator is deploying the analyte sensor system. The application is configured to analyze the one or more audio waveforms and identify one of a successful deployment and an unsuccessful deployment of the analyte sensor system based on the analyzing the one or more audio waveforms. The display device includes a display configured to display at least one of a first indication of a successful deployment responsive to the application identifying the successful deployment and a second indication of an unsuccessful deployment responsive to the application identifying the unsuccessful deployment.

In some embodiments, the analyzing the one or more audio waveforms includes identifying at least one portion of the one or more audio waveforms indicative of at least one part of the applicator performing a known movement of the successful deployment.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices for wireless communication of analyte data. In various deployments described herein, the analyte data is glucose data generated by an analyte sensor system configured to connect to display devices, partner devices (e.g., medical devices such as an insulin pump), other remote connectable devices, and the like. Implementing aspects of the present disclosure, including more particularly, the systems, methods, apparatuses, and devices described herein that provide increased robustness against false or otherwise undesired activation, wakeups, and/or related mode or state changes, or the like, for components of an analyte sensor system, may improve the accuracy, robustness, and/or power management of the analyte sensor system in wireless communications with a display device, one or more partner devices, and/or other (e.g., electronic) devices. Moreover, implementing aspects of the present disclosure may also allow for improving performance with respect to longevity and usability of the analyte sensor system.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

System Overview & Example Configurations

Figure 1:
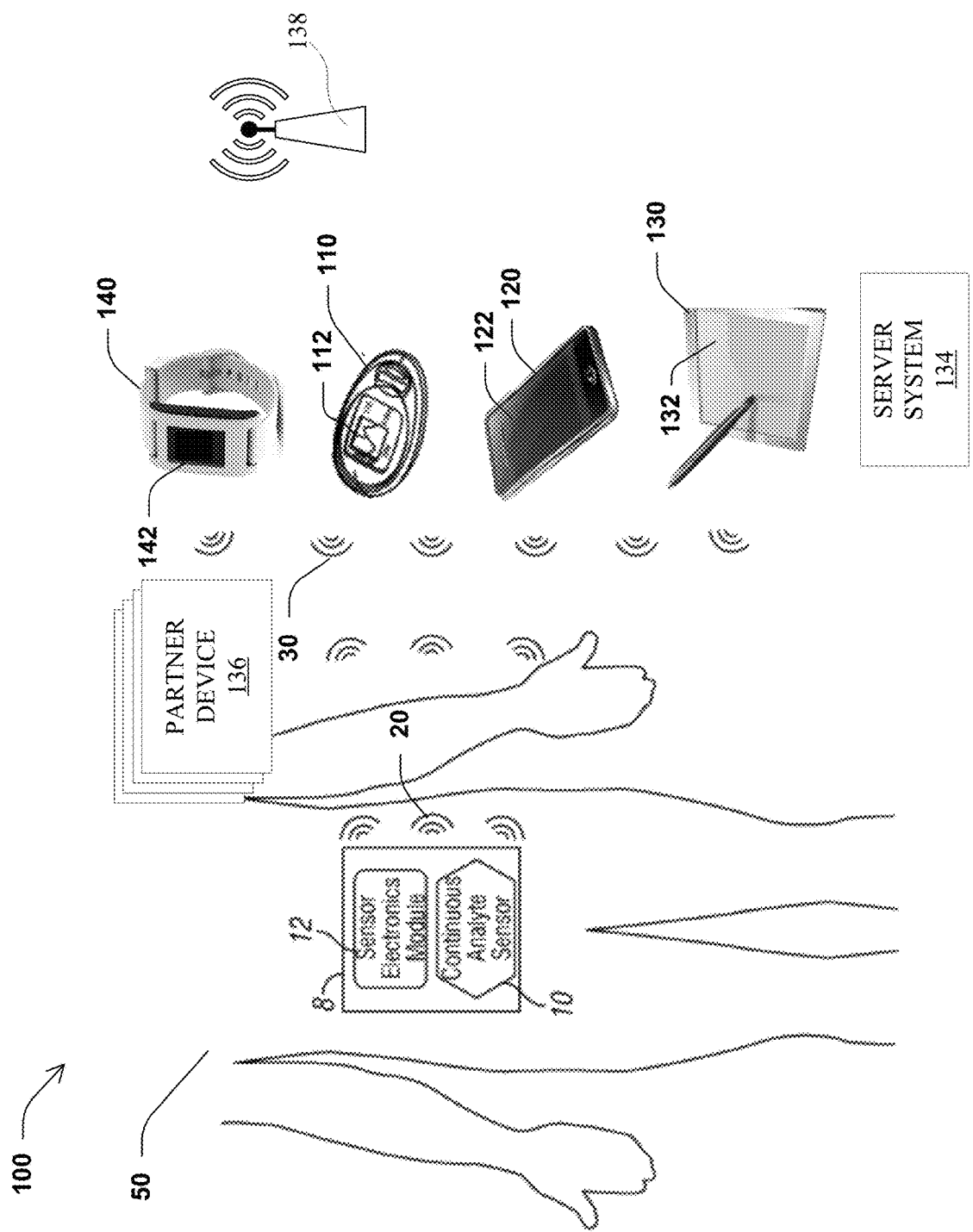
FIG. 1 illustrates aspects of an example system that may be used in connection with some embodiments.

FIG. 1 depicts system 100 that may be used in connection with embodiments of the present disclosure that involve gathering, monitoring, and/or providing information regarding analyte values present in a user's body, including for example the user's blood glucose values. System 100 depicts aspects of analyte sensor system 8 that may be communicatively coupled to display devices 110, 120, 130, and 140, partner devices 136, and/or server system 134.

Analyte sensor system 8 in the illustrated embodiment includes analyte sensor electronics module 12 and analyte sensor 10 associated with analyte sensor electronics module 12. Analyte sensor electronics module 12 may be electrically and mechanically coupled to analyte sensor 10 before analyte sensor 10 is implanted in a user or host. Accordingly, analyte sensor 10 may not require a user to couple analyte sensor electronics module 12 to analyte sensor 10. For example, analyte sensor electronics module 12 may be physically/mechanically and electrically coupled to analyte sensor 10 during manufacturing, and this physical/mechanical and electrical connection may be maintained during shipping, storage, insertion, use, and removal of analyte sensor system 8. As such, the electro-mechanically connected components (e.g., analyte sensor 10 and analyte sensor electronics module 12) of analyte sensor system 8 may be referred to as a "pre-connected" system. Analyte sensor electronics module 12 may be in wireless communication (e.g., directly or indirectly) with one or more of display devices 110, 120, 130, and 140. In addition, or alternatively to display devices 110, 120, 130, and 140, analyte sensor electronics module 12 may be in wireless communication (e.g., directly or indirectly) with partner devices 136 and/or server system 134. Likewise, in some examples, display devices 110-140 may additionally or alternatively be in wireless communication (e.g., directly or indirectly) with partner devices 136 and/or server system 134. Various couplings shown in FIG. 1 can be facilitated with wireless access point 138, as also mentioned below.

In certain embodiments, analyte sensor electronics module 12 includes electronic circuitry associated with measuring and processing analyte sensor data or information, including prospective algorithms associated with processing and/or calibration of the analyte sensor data/information. Analyte sensor electronics module 12 can be physically/mechanically connected to analyte sensor 10 and can be integral with (non-releasably attached to) or releasably attachable to analyte sensor 10. Analyte sensor electronics module 12 may also be electrically coupled to analyte sensor 10, such that the components may be electromechanically coupled to one another. Analyte sensor electronics module 12 may include hardware, firmware, and/or software that enables measurement and/or estimation of levels of the analyte in a host/user via analyte sensor 10 (e.g., which may be/include a glucose sensor). For example, analyte sensor electronics module 12 can include one or more of a potentiostat, a power source for providing power to analyte sensor 10, other components useful for signal processing and data storage, and a telemetry module for transmitting data from the sensor electronics module to one or more display devices. Electronics can be affixed to a printed circuit board (PCB) within analyte sensor system 8, or platform or the like, and can take a variety of forms. For example, the electronics can take the form of an integrated circuit (IC), such as an Application-Specific Integrated Circuit (ASIC), a microcontroller, a processor, and/or a state machine.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

With further reference to FIG. 1, display devices 110, 120, 130, and/or 140 can be configured for displaying (and/or alarming) displayable sensor information that may be transmitted by sensor electronics module 12 (e.g., in a customized data package that is transmitted to the display devices based on their respective preferences). Each of display devices 110, 120, 130, or 140 can (respectively) include a display such as touchscreen display 112, 122, 132, /or 142 for displaying sensor information and/or analyte data to a user and/or receiving inputs from the user. For example, a graphical user interface (GUI) may be presented to the user for such purposes. In embodiments, the display devices may include other types of user interfaces such as voice user interface instead of or in addition to a touchscreen display for communicating sensor information to the user of the display device and/or receiving user inputs. In embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1 may include a custom display device, for example, analyte display device 110, specially designed for displaying certain types of displayable sensor information associated with analyte data received from sensor electronics module 12 (e.g., a numerical value and/or an arrow, in embodiments). In embodiments, one of the plurality of display devices 110, 120, 130, 140 includes a smartphone, such as mobile phone 120, based on an Android, iOS, or other operating system, and configured to display a graphical representation of the continuous sensor data (e.g., including current and/or historic data).

As further illustrated in FIG. 1 and mentioned above, system 100 may also include wireless access point (WAP) 138 that may be used to couple one or more of analyte sensor system 8, the plurality display devices 110, 120, 130, 140 etc., server system 134, and medical device 136 to one another. For example, WAP 138 may provide WiFi and/or cellular or other wireless connectivity within system 100. Near Field Communication (NFC) may also be used among devices of system 100 for exchanging data, as well as for performing specialized functions, e.g., waking up or powering a device or causing the device (e.g., analyte sensor electronics module 12 and/or a transmitter) to exit a lower power mode or otherwise change states and/or enter an operational mode. Server system 134 may be used to collect analyte data from analyte sensor system 8 and/or the plurality of display devices, for example, to perform analytics thereon, generate universal or individualized models for glucose levels and profiles, provide services or feedback, including from individuals or systems remotely monitoring the analyte data, and so on. Partner device(s) 136, by way of overview and example, can usually communicate (e.g., wirelessly) with analyte sensor system 8, including for authentication of partner device(s) 136 and/or analyte sensor system 8, as well as for the exchange of analyte data, medicament data, other data, and/or control signaling or the like. Partner devices 136 may include a passive device in example embodiments of the disclosure. One example of partner device 136 may be an insulin pump for administering insulin to a user in response and/or according to an analyte level of the user as measured/approximated using analyte sensor system 8. For a variety of reasons, it may be desirable for such an insulin pump to receive and track glucose values transmitted from analyte sensor system 8 (with reference to FIG. 1 for example). One example reason for this is to provide the insulin pump a capability to suspend/activate/control insulin administration to the user based on the user's glucose value being below/above a threshold value.

Figure 2:
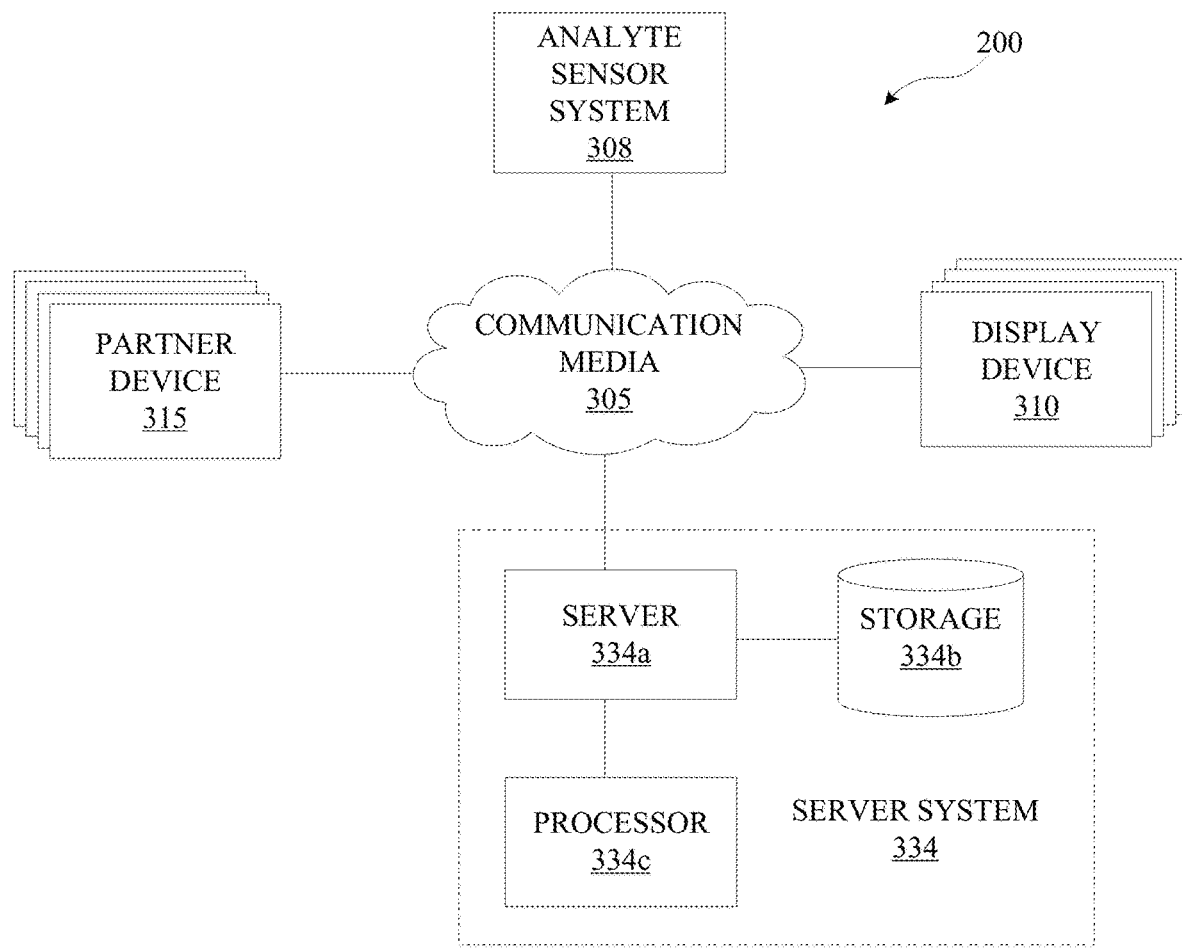
FIG. 2 illustrates aspects of an example system that may be used in connection with some embodiments.

Referring now to FIG. 2, system 200 is depicted. System 200 may be used in connection with implementing embodiments of the disclosed systems, methods, apparatuses, and/or devices, including, for example, aspects described above in connection with FIG. 1. By way of example, various below-described components of FIG. 2 may be used to provide wireless communication of analyte (e.g., glucose) data, for example among/between analyte sensor system 308, display devices 310, partner devices 315, and/or one or more server systems 334, and so on.

As shown in FIG. 2, system 200 may include analyte sensor system 308, one or more display devices 310, and/or one or more partner devices 315. Additionally, in the illustrated embodiment, system 200 includes server system 334, which can in turn includes server 334a coupled to processor 334c and storage 334b. Analyte sensor system 308 may be coupled to display devices 310, partner devices 315, and/or server system 334 via communication media 305. Some details of the processing, gathering, and exchanging of data, and/or executing actions (e.g., providing medicaments or related instructions) by analyte sensor system 308, partner devices 315, and/or display device 310, etc., are provided below.

Analyte sensor system 308, display devices 310, and/or partner devices 315 may exchange messaging (e.g., control signaling) via communication media 305, and communication media 305 may also be used to deliver analyte data to display devices 310, partner devices 315, and/or server system 334. As alluded to above, display devices 310 may include a variety of electronic computing devices, such as, for example, a smartphone, tablet, laptop, wearable device, etc. Display devices 310 may also include analyte display device 110 that may be customized for the display and conveyance of analyte data and related notifications etc. Partner devices 315 may include medical devices, such as an insulin pump or pen, connectable devices, such as a smart fridge or mirror, key fob, and other devices.

In embodiments, communication media 305 may be based on one or more wireless communication protocols, such as for example Bluetooth, Bluetooth Low Energy (BLE), Zig-Bee, WiFi, IEEE 802.11 protocols, Infrared (IR), Radio Frequency (RF), 2G, 3G, 4G, 5G, etc., and/or wired protocols and media. It will also be appreciated upon studying the present disclosure that communication media can be implemented as one or more communication links, including in some cases, separate links, between the components of system 200, whether or not such links are explicitly shown in FIG. 2 or referred to in connection therewith. By way of illustration, analyte sensor system 308 may be coupled to display device 310 via a first link of communication media 305 using BLE, while display device 310 may be coupled to server system 334 by a second link of communication media 305 using a cellular communication protocol (e.g., 4G LTE/5G and the like). In embodiments, a BLE signal may be temporarily attenuated to minimize data interceptions. For example, attenuation of a BLE signal through hardware or firmware design may occur temporarily during moments of data exchange (e.g., pairing).

In embodiments, the elements of system 200 may be used to perform operations of various processes described herein and/or may be used to execute various operations and/or features described herein with regard to one or more disclosed systems and/or methods. Upon studying the present disclosure, one of skill in the art will appreciate that system 200 may include single or multiple analyte sensor systems 308, communication media 305, and/or server systems 334.

As mentioned, communication media 305 may be used to connect or communicatively couple analyte sensor system 308, display devices 310, partner devices 315, and/or server system 334 to one another or to a network. Communication media 305 may be implemented in a variety of forms. For example, communication media 305 may include one or more of an Internet connection, such as a local area network (LAN), a person area network (PAN), a wide area network (WAN), a fiber optic network, internet over power lines, a hard-wired connection (e.g., a bus), DSL, and the like, or any other kind of network connection or communicative coupling. Communication media 305 may be implemented using any combination of routers, cables, modems, switches, fiber optics, wires, radio (e.g., microwave/RF, AM, FM links etc.), and the like. Further, communication media 305 may be implemented using various wireless standards, such as Bluetooth®, BLE, Wi-Fi, IEEE 802.11, 3GPP standards (e.g., 2G GSM/GPRS/EDGE, 3G UMTS/CDMA2000, or 4G LTE/LTE-A/LTE-U, 5G, or subsequent generation), etc. Upon reading the present disclosure, one of skill in the art will recognize other ways to implement communication media 305 for communications purposes and will also recognize that communication media 305 may be used to implement features of the present disclosure using as of yet undeveloped communications protocols that may be deployed in the future.

Further referencing FIG. 2, server 334a may receive, collect, and/or monitor information, including analyte data, medicament data, and related information, from analyte sensor system 308, partner devices 315 and/or display devices 310, such as input responsive to the analyte data or medicament data, or input received in connection with an analyte monitoring application running on analyte sensor system 308 or display device 310, or a medicament delivery application running on display device 310 or partner device 315. As such, server 334a may receive, collect, and/or monitor information from partner devices 315, such as, for example, information related to the provision of medicaments to a user and/or information regarding the operation of one or more partner devices 315. Server 334a may also receive, collect, and/or monitor information regarding a user of analyte sensor system 308, display devices 310, and/or partner devices 315.

In embodiments, server 334a may be adapted to receive such information via communication media 305. This information may be stored in storage 334b and may be processed by processor 334c. For example, processor 334c may include an analytics engine capable of performing analytics on information that server 334a has collected, received, etc. via communication media 305. In embodiments, server 334a, storage 334b, and/or processor 334c may be implemented as a distributed computing network, such as a Hadoop® network, or as a relational database or the like. The aforementioned information may then be processed at server 334a such that services may be provided to analyte sensor system 308, display devices 310, partner devices 315, and/or a user(s) thereof. For example, such services may include diabetes management feedback for the user.

In embodiments, a database may be implemented in server system 334 that may pair user accounts to one or more analyte sensor systems 308 using communication media 305. Based on, for example, an expected lifetime of individual components or one or more groups of components of analyte sensor system 308, or analyte sensor system 308 as a whole, and/or based on diagnostic feedback received by analyte sensor system 308, server system 334 may be able to determine if a given analyte sensor system 308 or component or group(s) of components thereof is expired or passed its useful life. A user may receive an indication, notification, alert, or warning, for example, on display device 310 and/or through analyte sensor system 308, from server system 334, that analyte sensor system 308 or a component or group(s) of components thereof has expired or passed its useful life or will do so soon or within a given amount of time. In embodiments, a user may receive an indication, notification, alert, or warning on display device 310 from server system 334 about the expected lifetime of analyte sensor system 308 or a component or group(s) of components thereof.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication media 305. Such communications may include the delivery of analyte data, medicament data, and/or messaging related thereto (e.g., advertisement, authentication, command, or other messaging). For example, server 334a may process and exchange messages between and/or among analyte sensor system 308, display devices 310, and/or partner devices 315 related to frequency bands, timing of transmissions, security/encryption, alarms, alerts, notifications, and so on. Server 334a may update information stored on analyte sensor system 308, partner devices 315, and/or display devices 310, for example, by delivering applications thereto or updating the same, and/or by reconfiguring system parameters or other settings of analyte sensor system 308, partner devices 315, and/or display devices 310. Server 334a may send/receive information to/from analyte sensor system 308, partner devices 315, and/or display devices 310 in real time, periodically, sporadically, or on an event-drive basis. Further, server 334a may implement cloud computing capabilities for analyte sensor system 308, partner devices 315, and/or display devices 310.

With the above description of aspects of the presently disclosed systems and methods for wireless communication of analyte data, examples of some specific features of the present disclosure will now be provided. It will be appreciated by one of skill in the art upon studying the present disclosure that these features may be implemented using aspects and/or combinations of aspects of the example configurations described above, whether or not explicit reference is made to the same.

Analyte Data

Referring back to FIG. 1, as mentioned above, in embodiments, analyte sensor system 8 is provided for measurement of an analyte in a host or user. By way of an overview and an example, analyte sensor system 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices (e.g., display devices 110, 120, 130, 140, partner devices 136, and/or server system 134).

Analyte sensor system 8 may include: analyte sensor 10 configured to measure a concentration or level of the analyte in the host, and analyte sensor electronics module 12 that is typically physically connected to analyte sensor 10 before analyte sensor 10 is implanted in a user. In embodiments, analyte sensor electronics module 12 includes electronics configured to process a data stream associated with an analyte concentration measured by analyte sensor 10, in order to generate sensor information that includes raw sensor data, transformed sensor data, and/or any other sensor data, for example. Analyte sensor electronics module 12 may further be configured to generate analyte sensor information that is customized for respective display devices 110, 120, 130, 140, partner devices 136, and/or server system 134. Analyte sensor electronics module 12 may further be configured such that different devices may receive different sensor information and may further be configured to wirelessly transmit sensor information to such display devices 110, 120, 130, 140, partner devices 136, and/or server system 134.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Preconnected Analyte Sensor System

As alluded to above with reference to FIG. 1, in embodiments, analyte sensor 10 includes a continuous glucose sensor, for example, a subcutaneous, transdermal (e.g., transcutaneous), or intravascular device. In embodiments, such a sensor or device can analyze a plurality of intermittent blood samples. Analyte sensor 10 can use any method of analyte measurement, including for example glucose-measurement, including enzymatic, chemical, physical, electrochemical, spectrophotometric, polarimetric, calorimetric, iontophoretic, radiometric, immunochemical, and the like.

In embodiments where analyte sensor 10 is a glucose sensor, analyte sensor 10 can use any method, including invasive, minimally invasive, and non-invasive sensing techniques (e.g., fluorescence monitoring), or the like, to provide a data stream indicative of the concentration of glucose in a host. The data stream may be a raw data signal, which may be converted into a calibrated and/or filtered data stream that can be used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of an analyte, glucose for example, and providing an output signal that represents the concentration of the analyte, again glucose for example (e.g., as a form of analyte data).

In embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example.

The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Before system activation, analyte sensor electronics module 12 is typically maintained in a lower power mode in order to conserve or manage battery capacity. Analyte sensor electronics module 12, in order to begin gathering analyte data in an active power state, should generally be activated reliably. For example, it may be preferable not to activate analyte sensor electronics module 12 until around the time when analyte sensor 10 is implanted in a host. This may help maintain more accurate sensor calibration, may reduce power consumption, and/or may generally increase analyte measurement accuracy, etc. In some embodiments, the activation of analyte sensor electronics module 12 and/or certain circuits thereof may at least primarily occur prior to analyte sensor 10 implantation (e.g., within 5 minutes, 1 minute, 30 s, 10 s, 1 s, or less than 1 s before implantation, or the like). In some embodiments, activation of analyte sensor electronics module 12 may at least primarily occur during or substantially during implantation (e.g., at least partially while analyte sensor 10 is translating to the deployed position). In some embodiments, activation of analyte sensor electronics module 12 may at least primarily occur after the time of analyte sensor 10 implantation (e.g., within less than 1 s, 1 s, 5 s, 30 s, 1 min, 3 mins, 5 mins, 10 mins, more than 10 mins after implantation, or the like). In embodiments, it is preferred for analyte sensor electronics module 12 to exit a lower power state at or shortly before the time around which analyte sensor 10 is implanted. This may allow the time of implantation to be more accurately recorded.

In systems that are not pre-connected, analyte sensor 10 and analyte sensor electronics module 12 are usually mechanically and electrically connected for the first time after analyte sensor 10 is implanted into the user. Electrodes of analyte sensor electronics module 12 are typically monitored to detect an analyte related signal when analyte sensor electronics module 12 is coupled to an already implanted analyte sensor 10. Analyte sensor system 8 may then be activated in response to the coupling and detection of a particular level or characteristic of analyte in a user. However, in a pre-connected analyte sensor system 8, analyte sensor 10 may be electromechanically coupled to analyte sensor electronics module 12 before analyte sensor system 8 is delivered to user and thus analyte sensor electronics module 12 is already coupled to analyte sensor 10 at the time of sensor implantation. As alluded to above, this pre-coupling or pre-connection can lead to erroneous wakeups or activation from a lower power state, for example due to a signal generated by analyte sensor system 8 prior to sensor implantation (e.g., in situations of high humidity, static electricity, current leakage, or noise). Also, to improve accuracy in converting a sensor signal to an analyte value with a sensor processing algorithm, it may be preferred that analyte sensor 10 is not voltage biased by analyte sensor electronics module 12 before implantation.

Operations that may cause changes to properties of analyte sensor 10 should generally be minimized before implantation. Accordingly, it may be preferred to avoid or at least reduce the occurrence of voltage biasing analyte sensor 10 before implantation. Applying voltage bias to analyte sensor 10 on a relatively long-term basis (e.g., during storage) may cause analyte sensor 10 to have a shorter than intended use life following implantation. This may be due to, for example, consumption of reference or enzyme capacity that may be contained on analyte sensor 10. Moreover, an analyte processing algorithm that may be used by analyte sensor system 8 may rely upon characterized performance values of analyte sensor 10. These characterized performance values may include a baseline signal, analyte sensitivity, signal drift, lot performance metrics, curve fitting variables, tabular values, calibration codes, and/or additional factors that may be used as part of a signal processing algorithm in connection with determining analyte values. Thus, in some instances particularly for factory calibrated analyte sensors 10, it can be important to have a relatively accurate estimate of analyte sensor 10 performance parameters and/or characteristics at the time of implantation into a user, in order to enable accurate generation of analyte values. Significant durations (e.g., during shelf life) of applying a voltage bias across analyte sensor 10 may cause deviations from one or more predetermined performance metrics. This may tend to decrease the accuracy of analyte values determined using a sensor processing algorithm to convert one or more measured analyte sensor 10 signals to analyte values after analyte sensor 10 implantation. Additionally, deviation from the calibrated state of analyte sensor 10 during storage can cause the algorithm to report less accurate or inaccurate analyte values.

Furthermore, the amount of power (e.g., mW) used by the circuitry and/or other components (e.g., within analyte sensor electronics module) that control activation of analyte sensor system 8 should generally be minimized, reduced, and/or considered in connection with making system level performance tradeoffs where possible. For measurements generated using analyte sensor 10 or other circuits or components, care should generally be taken to minimize, reduce, and/or control power usage prior to activation of analyte sensor system 8. Power budgets may be at least somewhat limited by a battery capacity of analyte sensor system 8. Thus, analyte sensor system 8 may primarily remain in a lower power or mostly non-operational state prior to activation, and techniques used to control system activation and/or exit the lower power state may consume a small portion of available power.

In embodiments, lower power consumption is achieved by, for example, selecting a reduced or minimum viable polling or sampling frequency for power usage and detectability of a system activating event and/or trigger. In some cases, a sampling or polling frequency used to monitor an activating event/trigger/characteristic may be varied based on the type of detection scheme that is being used (e.g., capacitance measurement versus accelerometer input, as will be described below). In connection with reducing power consumption, lower power state machines that perform measurement and logic functions to trigger system wakeup without powering up a main system processor may be employed. For example, a lower power state can be effectively maintained through employing a reduced and/or variable, adaptable, programmable, and/or configurable polling or sampling frequency. In some cases, this lower power state can be facilitated through the use of low power state machines. The lower power state, in which power consumption can be controlled/reduced, can in this fashion largely be maintained notwithstanding periodic polling/sampling that may be done in connection with detecting an activation event for analyte sensor system 8.

In embodiments, analyte sensor system 8 is made more robust to false wake ups, and if a false wake up is detected, the system can return to a lower power state. For example, if at any point analyte sensor system 8 detects that analyte sensor 10 generates a signal that does not satisfy a threshold or one or more characteristics indicative of a wakeup event, analyte sensor system 8 may return to or remain in the lower power state. By way of example, in such a lower power state, there may be no data transmission or analyte measurements by analyte sensor electronics module 12. Lower power and active states may be implemented primarily in firmware in many cases, but some wake up circuits may have hardware integration to enable more robust activation detection mechanisms (e.g., discharging a capacitor, etc., as will be described herein).

Accordingly, embodiments of the present disclosure involve employing multiple techniques and/or mechanisms/components/circuits for detecting and confirming that a lower power state of pre-connected analyte sensor system 8 may be changed. By way of illustration, such a change may entail analyte sensor system 8 being activated, caused to exit a lower power state, and/or caused to move into a more active state. This may take place in response to conditions that indicate analyte sensor 10 has been implanted into a user. In one example, analyte sensor system 8 can detect an analyte using analyte sensor 10 and a potentiostat or other measurement device that applies a voltage bias on one or more electrodes of analyte sensor 10 and measures the resulting amount of current that flows. This current and/or related signals may be referred to herein as a primary signal.

Additionally, by way of example, there may be a characteristic signal profile that can be measured when analyte sensor 10 is implanted into tissue of a host. Such a characteristic signal profile can result from changes in analyte sensor 10 when analyte sensor 10 is first exposed to the tissue environment, for example due to membrane hydration and/or resulting changes in analyte and/or ionic concentrations. Such characteristic signal profiles may be referred to herein as secondary signals. In embodiments, secondary signals may include or involve the use of capacitance, impedance, or other electrical measurements of analyte sensor 10.

The signal characteristics of a primary signal measured using analyte sensor 10 (e.g., voltage or current or the like) along with in vivo and/or in factory calibration information for analyte sensor 10 may be used by an analyte processing algorithm implemented, for example, using analyte sensor electronics module 12 to convert the primary signal to analyte concentration levels. The signal characteristics of the primary signal may change over time. Examples of signal profiles for analyte values (e.g., which may be measured in mg/dL) or for other measurements taken using one or more electrodes of analyte sensor 10 (e.g., voltage, current, digital "counts," etc.) include the following: gradient of signal, threshold of signal, integration over time, slope, balance, range, or any other characteristics that may be used to specifically identify the signal. Such signal profiles/characteristics can be predefined in analyte sensor system 8.

Employing multiple of the above-referenced techniques and other means for activation/state change, etc., in a pre-connected analyte sensor system 8 can better enable accurately detecting implantation of analyte sensor 10 into a user, which in turn has numerous advantages. For example, accurately detecting or approximating an implantation time for analyte sensor 10 can better enable a factory calibrated system. By way of example, a signal processing algorithm implemented using, e.g., processor 535 of analyte sensor system 308 (referencing FIG. 5 by way of example), may use one or more techniques in the conversion of an analyte sensor signal to an estimated analyte value. During different periods of an analyte sensor 10 lifecycle (e.g., less than one hour after implantation, less than 4 hours after implantation, more than 4 hours after implantation, etc.), these conversion techniques may provide different levels of accuracy with respect to the conversion. In embodiments, some of these techniques may rely on predetermined signal profiles that are time dependent. Therefore, recording and/or estimating a more accurate implantation time of analyte sensor 10 may be beneficial for selecting a signal processing algorithm and addressing variations in a processing technique that may occur as a function of time. An analyte sensor system 8 that uses such techniques/means may thus have improved overall accuracy as well as improved performance upon implantation of analyte sensor 10 (e.g., as performance upon implantation may be impacted, including by errors that may be induced from not accurately assessing/detecting a time at which analyte sensor 10 is implanted). For example, inaccuracies may be introduced due to the slope of a sensitivity of analyte sensor 10 following implantation, or due to background signal changes that may occur following implantation of analyte sensor 10.

Accurate detection of implantation time can also enable faster startup of analyte sensor system 8 in terms of providing analyte information to a user. For example, a more accurate implantation time may be useful for an analyte calculation algorithm implemented in analyte sensor system 8 to determine an appropriate time point to begin displaying analyte information to a user (e.g., a confidence level between signal and analyte conversion). Due to the slope of analyte related signal changes within a first interval of time (e.g., 2 hours, etc.) after implantation of analyte sensor 10, implantation timing errors may result in inappropriate predictions to the signal response and analyte signal. Recognizing the time point in the characteristic signal decay curve may enable analyte sensor system 8 and/or devices operating in conjunction therewith to display or provide analyte information (e.g., on a display devices 110, 120, 130, 140, to server system 134, and/or to partner device(s) 136, with reference by way of example to FIG. 1) relatively sooner than if the implantation time of analyte sensor 10 was less accurately determined (e.g., within 2 hours, 1 hour, 30 minutes, 15 minutes, or less).

Additionally, accurate detection of the implantation time of analyte sensor 10 can assist in preventing reuse of analyte sensor 10. Detection of sensor implantation time by electronics module 12 can enable a higher reliability metric versus a reliance on the user providing notification of insertion/implantation time. For example, disconnection and/or implantation characteristics can distinguish a newly inserted analyte sensor 10 from an attempt of the user to restart an expired analyte sensor 10.

As an additional example, accurate detection/estimation of analyte sensor 10 implantation time may enable faster connectivity establishment between analyte sensor electronics module 12 and devices connectable thereto (see, e.g., FIG. 1). With a more accurate detection and/or estimation of analyte sensor 10 implantation time, analyte sensor system 8 may be placed in a state to establish and enter into communication with multiple devices based on being near to or at the time of implantation. For example, analyte sensor system 8 may be able to enter a pairing state within a relatively short time of implantation (e.g., less than 10 to 15 minutes) such that display devices (e.g., display devices 110, 120, 130, 140, partner device(s) 136, etc., referencing FIG. 1 by way of example) may be able to wirelessly connect to analyte sensor system 8. A more accurate detection of analyte sensor 10 implantation time may also be used to trigger alternative connection profiles to encourage faster connection, for example, pairing, encryption, advertisement characteristics, etc. That is, for example, a more definitive wakeup event can be used to facilitate a more aggressive connection model as between analyte sensor system 8 and a device connectable thereto (e.g., sending advertisement packets at a faster rate or the like). This may enable faster connection establishment and may also provide the user with near real time feedback that analyte sensor system 8 is receiving a signal and is connected to the display device.

An additional example of an advantage associated with accurate estimation of analyte sensor 10 implantation time that can be enabled by more robust wakeup techniques for analyte sensor 8 is improving error detection. Knowing the predicted profile and monitoring the signal measured using analyte sensor 10 from the time of implantation can enable recognition of deviations from expected characteristics of implantation in the signal profile. This can be enabled by knowledge of the implantation time of analyte sensor 10 as well as the ability to analyze the analyte signal at the time of implantation (for example, a signal that is associated with implantation is less likely to be missed due to analyte sensor system 8 being in a lower power state). The ability to recognize such deviations can trigger system safety or accuracy errors that may be hazardous for a user of analyte sensor system 8. For example, analyte sensors 10 that are physically damaged (e.g., membrane breaches, tears, manufacturing errors, etc.) may have different characteristic signals after implantation.

Yet another example of an advantage associated with accurate estimation of analyte sensor 10 implantation time is faster wakeup time for analyte sensor system 8, which may also enable improved error detection abilities. Risks of user variation in analyte sensor 10 implantation time may be reduced by using analyte sensor system 8 that is pre-connected and by detecting implantation time for analyte sensor 10 automatically or semi-automatically. Analyte sensor 10 that has been inserted into the incorrect tissue location (for example, not under the skin, or into muscle/fascia rather than a desired tissue layer) may have different characteristic signals than expected following insertion. Faster wakeup time may enable such issues to be detected more quickly following implantation, thus improving overall error detection performance associated with analyte sensor system 8.

Figure 3A:
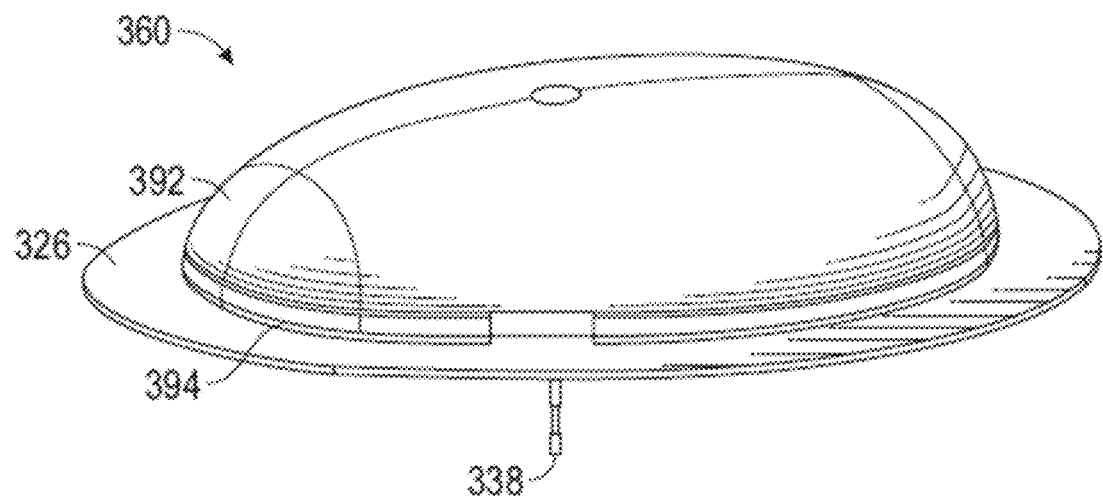
FIG. 3A is an example analyte sensor system, in accordance with some embodiments.

FIG. 3A illustrates a perspective view of an on-skin sensor assembly 360 that may be used in connection with a pre-connected analyte sensor system 8, in accordance with some embodiments. For example, on-skin analyte sensor assembly 360 may include analyte sensor system 8, with reference by way of example to FIG. 1. On-skin sensor assembly 360 may include an outer housing with a first, top portion 392 and a second, lower portion 394. In embodiments, the outer housing may include a clamshell design. On-skin sensor assembly 360 may include, for example, similar components as analyte sensor electronics module 140 described above in connection with FIG. 1, for example, a potentiostat, a power source for providing power to analyte sensor 10, signal processing components, data storage components, and a communication module (e.g., a telemetry module) for one-way or two-way data communication, a printed circuit board (PCB), an integrated circuit (IC), an Application-Specific Integrated Circuit (ASIC), a microcontroller, and/or a processor.

As shown in FIG. 3A, the outer housing may feature a generally oblong shape. The outer housing may further include aperture 396 disposed substantially through a center portion of outer housing and adapted for sensor 338 and needle insertion through a bottom of on-skin sensor assembly 360. In embodiments, aperture 396 may be a channel or elongated slot. On-skin sensor assembly 360 may further include an adhesive patch 326 configured to secure on-skin sensor assembly 360 to skin of the host. In embodiments, adhesive patch 326 may include an adhesive suitable for skin adhesion, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated. As shown, adhesive patch 396 may feature an aperture 398 aligned with aperture 396 such that sensor 338 may pass through a bottom of on-skin sensor assembly 360 and through adhesive patch 396.

Figure 3B:
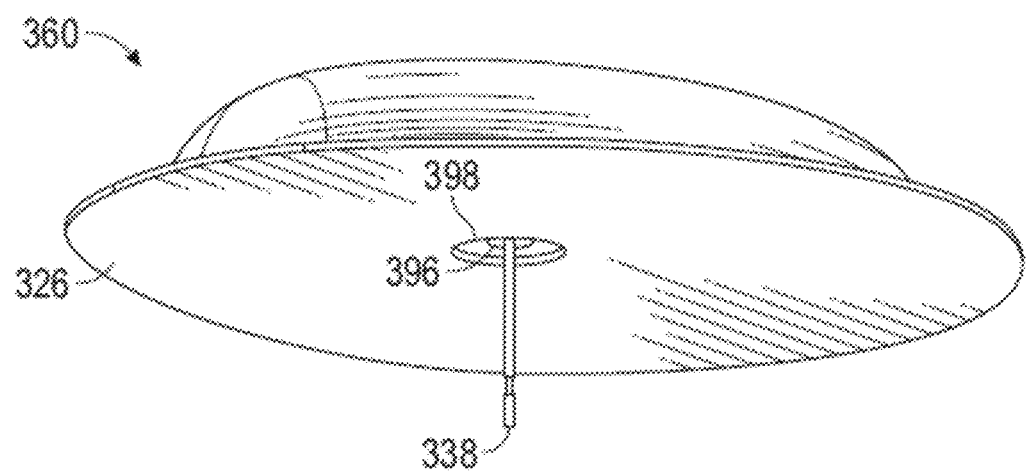
FIG. 3B is an example analyte sensor system, in accordance with some embodiments.

FIG. 3B illustrates a bottom perspective view of on-skin sensor assembly 360 of FIG. 3A. FIG. 3B further illustrates aperture 396 disposed substantially in a center portion of a bottom of on-skin sensor assembly 360, and aperture 398, both adapted for sensor 338 and needle insertion.

Figure 4:
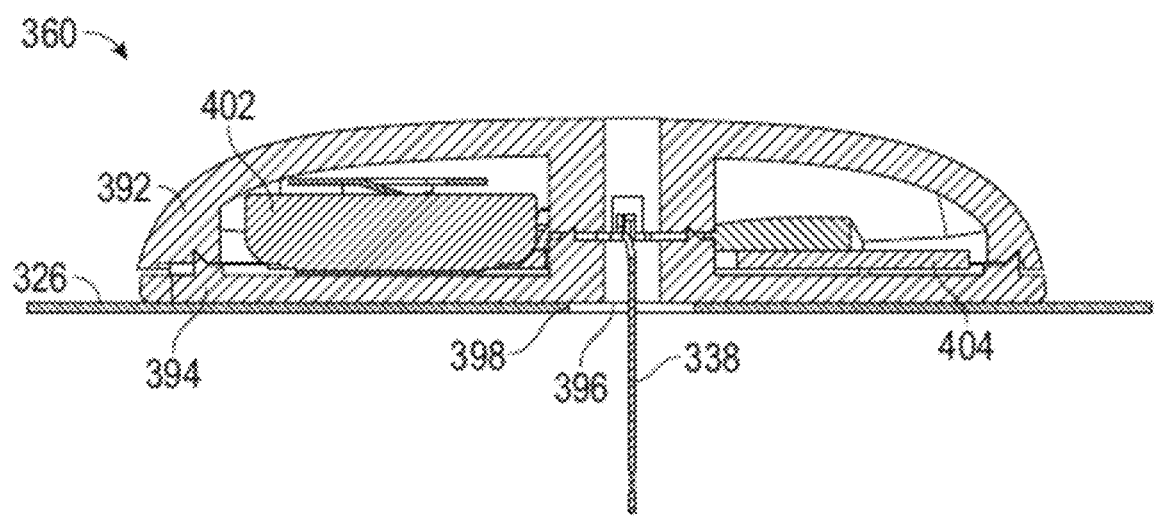
FIG. 4 illustrates aspects of an example analyte sensor system, in accordance with some embodiments.

FIG. 4 illustrates a cross-sectional view of on-skin sensor assembly 360 of FIGS. 3A and 3B. FIG. 4 illustrates first, top portion 392 and second, bottom portion 394 of the outer housing, adhesive patch 326, aperture 396 in the center portion of on-skin sensor assembly 360, aperture 398 in the center portion of adhesive patch 326, and sensor 338 passing through aperture 396. The electronics unit, previously described in connection with FIG. 3A, may further include circuit board 404 and battery 402 configured to provide power to at least circuit board 404.

Figure 5:
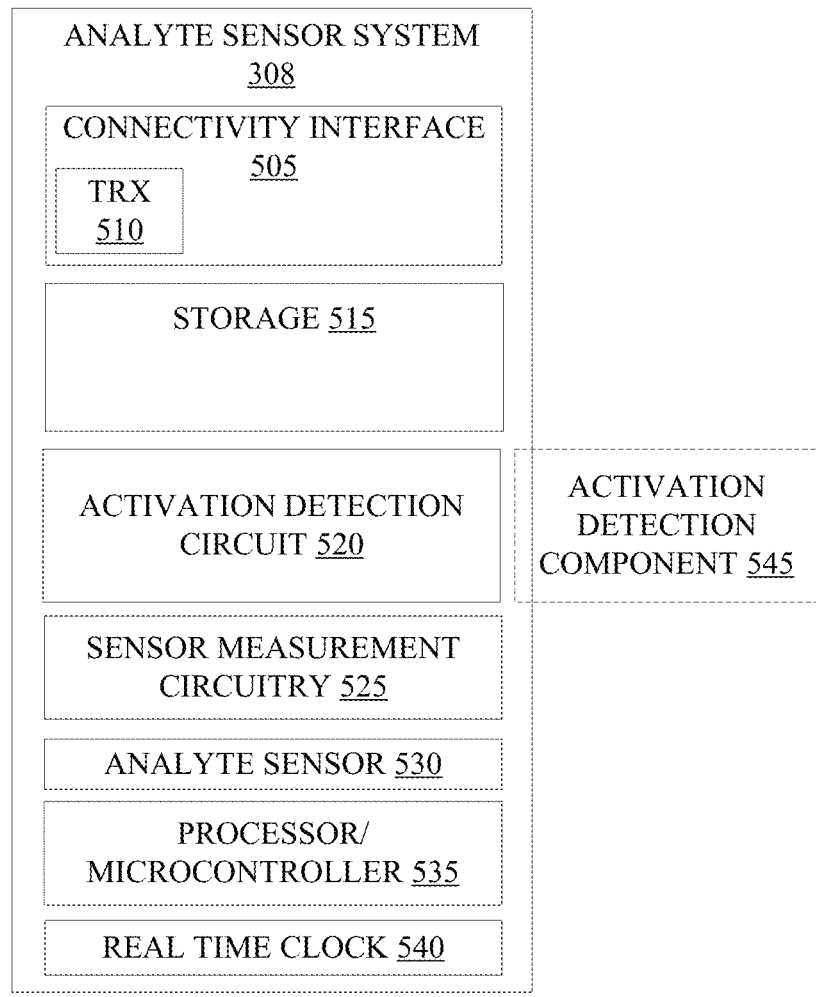
FIG. 5 illustrates aspects of an example analyte sensor system, in accordance with some embodiments.

Turning now to FIG. 5, a more detailed functional block diagram of analyte sensor system 308 (discussed above, for example, in connection with FIGS. 1 and 2) is provided. As shown in FIG. 5, analyte sensor system 308 may include analyte sensor 530 (e.g., which may also be designated with the numeral 10 in FIG. 1) coupled to analyte sensor measurement circuitry 525 for processing and managing sensor data. Sensor measurement circuitry 525 may be coupled to processor/microprocessor 535 (e.g., which may be part of item 12 in FIG. 1). In some embodiments, processor 535 may perform part or all of the functions of sensor measurement circuitry 525 for obtaining and processing sensor measurement values from analyte sensor 530.

Processor 535 may be further coupled to a radio unit or transceiver 510 (e.g., which may be part of item 12 in FIG. 1) for sending sensor and other data and receiving requests and commands and other signaling from an external device, such as display device 310 (referencing FIG. 2 by way of example). Display device 310 may be used to display or otherwise provide the sensor data (or analyte data) or data derived therefrom to a user, server system 334, and/or partner device 315. Partner device 315 may utilize sensor data or a derivative data derived therefrom in the administration of medicaments (e.g., insulin) and/or diabetes management guidance to the user. As used herein, the terms "radio unit" and "transceiver" may be used interchangeably and generally refer to a device that can wirelessly transmit and receive data. Analyte sensor system 308 may further include storage 515 (e.g., which may be part of item 12 in FIG. 1) and real time clock (RTC) 540 (e.g., which may be part of item 12 in FIG. 1), for storing and tracking sensor and other data.

Analyte sensor system 308 may also include activation detection circuit 520. Activation detection circuit 520 may optionally operate in conjunction with activation detection component 545. Activation detection component 545 may be integral to analyte sensor system 308, may be a component attachable thereto, and/or may be external thereto. Examples of activation detection circuit 520 may include one or more of (1) measurement circuitry that measures electrical characteristics associated with analyte sensor 10, such as capacitance or impedance, etc.; (2) proximity detection circuitry, which may use, for example, capacitive sensing, inductive sensing, magnetic detection, sonic detection, etc.; (3) temperature measurement circuitry; (4) accelerometer circuitry; (5) radio and/or antenna circuitry for NFC/RFID; (6) air pressure detection circuitry; (7) audio circuitry; (8) optical detection circuitry; (9) conductivity measurement circuitry; (10) switch detection circuitry; (11) strain detection circuitry; and so on. Activation detection circuitry 520 and/or activation detection component 545 may also use or include logic circuitry adapted to execute stored instructions or computer code to perform functionalities as described herein with respect to detecting activation events/triggers and otherwise enabling activation of analyte sensor system 8 based upon triggering events/conditions and/or measurement of analyte values/characteristics/profiles. Additional details regarding activation detection circuit 520 and activation detection component 545 are discussed further elsewhere herein.

Analyte sensor system 308 in example implementations gathers analyte data using sensor 530 and transmits the same or a derivative thereof to display device 310, partner device 315, and/or server system 334. Data points regarding analyte values may be gathered and transmitted over the life of sensor 530. New measurements and/or related information may be transmitted often enough for a remote device/individual to adequately monitor analyte (e.g., glucose) levels.

It is to be appreciated that some details of the processing, gathering, and exchanging data by analyte sensor system 308, partner devices 315, and/or display device 310 etc. are provided elsewhere herein. It will be appreciated upon studying the present disclosure that analyte sensor system 308 may contain several like components that are described with respect to FIG. 1 or 2, at least for some embodiments herein. The details and uses of such like components may therefore be understood vis-à-vis analyte sensor system 308 even if not expressly described here with reference to FIG. 5.

Exiting a Low Power State

As discussed above, embodiments of the present disclosure concern the timing for activating analyte sensor system 308 or causing the same to exit a lower power mode, particularly where analyte sensor system 308 is a pre-connected system. For example, in such a pre-connected system, analyte sensor 10 may be mechanically and electrically coupled to analyte sensor electronics module 12 before analyte sensor 10 is implanted into a host. There are several different time periods at which analyte sensor system 308 may exit a lower power mode, with each time period typically having associated trade-offs.

One time period at which analyte sensor system 308 may exit a lower power state is upon a user opening a package containing analyte sensor system 308 or upon a user removing analyte sensor system 308 from such a package. For example, using a switch, magnet, or other means described herein, the analyte sensor system 308 could be caused to exit the lower power state in response to the opening of a shipping box or sterile pack for analyte sensor system 308, in response to the removal of a cap/lid for the system, and/or in response to peeling foil/Tyvek packaging for the system. However, exiting a lower power state at this time period may have a higher probability of not immediately preceding insertion of analyte sensor 10 into a user, therefore potentially increasing the power usage requirement of analyte sensor system 308. For example, if multiple analyte sensor systems 308 are typically delivered to the user in a single package (e.g., a four-pack), all delivered analyte sensor systems 308 may be activated in this scenario even though only one of the analyte sensor systems 308 may likely be used in the near term. In another example, after the user removes a packaging lid for analyte sensor system 308, thus triggering analyte sensor 10 to be biased, the user may delay implantation of analyte sensor 10 until after analyte sensor 10 is biased or after other secondary verification means are employed, thus wasting any power used to employ such secondary verification means (e.g., NFC, accelerometer, impedance measurement, etc., as described in detail herein) and potentially decreasing the accuracy of analyte sensor 10 due to calibration drift that may result from applying bias.

Another example time period at which analyte sensor system 308 may exit a lower power state is when analyte sensor system 308 is in an applicator but has not yet been deployed. Example techniques that may be employed for exiting the lower power state at this time period include mechanical means (e.g., a bridge, etc.) and electrical or other nonmechanical means (e.g., NFC, magnetic, sonic detection, etc.), as will be discussed in further detail below. In certain situations, this time period may be preferred because it may be easier to detect activation events, for example, because typically detectable events that may occur (such as analyte sensor system 308 changing positions relative to the applicator) during this time period may occur over a longer period of time, relative to, e.g., detectable events that may be associated with analyte sensor system 308 deployment. This time period may also be preferred for detecting activation related indicators because it is usually closer in time to implantation of analyte sensor 10, thus helping reduce user-created false wakeups, such as, for example, that may occur when the user unboxes analyte sensor system 308 but then chooses not to implant analyte sensor 10. Thus, events that may occur in the applicator for analyte sensor system 308 may serve as more effective markers for estimating implantation time and/or activating analyte sensor system 308 or causing the same to exit a lower power state.

Yet another time period at which analyte sensor system 308 can be caused to exit a lower power state is during the deployment of analyte sensor system 308 (e.g., the translation of analyte sensor 10 from the proximal position to the distal position into the tissue of a host). Here again, either electrical or electro-mechanical means, or both, may be used to trigger an activation of analyte sensor system 308. One potential issue with using deployment-related events for activation purposes, however, may be that deployment usually occurs over a shorter time period relative to activation related indicators that occur in association with the applicator, for example (as described above), so the signal or event may be easier to miss or harder to detect relative to applicator-related events.

Another time period that may be used for causing analyte sensor system 308 to exit a lower power state may be after the implantation of analyte sensor 10. Mechanical, electrical, and/or electromechanical (or other nonmechanical) means may be employed for triggering an activation of analyte sensor system 308. Additionally, or alternatively, analyte sensor 10 itself may be used for triggering analyte sensor system 308 to wake up or exit a lower power state. By way of example, a measured capacitance of analyte sensor 10 and/or a measured value for a membrane impedance of the sensor and/or a measured value of a user's skin impedance may be compared to a known condition (e.g., a threshold value) such that the comparison can be used to indicate implantation of analyte sensor 10. However, after the insertion of analyte sensor 10, any delay in detecting insertion of analyte sensor 10 can impact the accuracy of an analyte processing algorithm used to calculate analyte values. Furthermore, such delay can impact analyte sensor system 308 from executing other operations that it is capable of performing, such as, pairing with display devices 310, partner devices 315, etc., communicating analyte values to display devices 310, partner devices 315, etc., and the like.

Using Signals from the Analyte Sensor to Exit Lower Power State

As referenced above, embodiments of the present disclosure involve detecting implantation of analyte sensor 10 into a user, including, for example, where implantation is detected using analyte sensor 10, and causing analyte sensor system 308 to activate and/or exit a lower power state, in an accurate and power-efficient manner. In example embodiments, an analyte signal from analyte sensor 10 is used for activation purposes. For example, activation detection circuit 520 may use one or more signals from a potentiostat to generate the analyte signal and/or for example, to detect/measure current flow through analyte sensor 10 (or analyte sensor 530, referencing FIG. 5, though it should be appreciated that these components may be referred to interchangeably in some cases) over time. Such signals may be quantified in units such as pA (current flow), pW (power), or counts (digital values converted from an analog value such as a voltage, a current, a power and/or a time), and these values can be used for purposes of triggering analyte sensor system 308 to exit a lower power state. For example, a benchmark threshold of current units may be used for triggering a wake-up or activation of analyte sensor system 308. However, basing such triggering on a predetermined current unit (e.g., counts) threshold can sometimes result in false wakeups or missed wakeups. For example, if the predetermined threshold is satisfied even though analyte sensor 10 has not been properly implanted into a host (e.g., via electrostatic discharge that may occur prior to deployment, for example while analyte sensor 10 is in packaging), then analyte sensor system 308 may be caused to wake up or enter an operational mode in situations when it should remain in lower power state or storage mode.

Thus, embodiments of analyte sensor system 308 use a benchmark threshold for current measurements for analyte sensor 10 (e.g., of approximately X counts, where X may be, for example, 9,000 counts) that may generally be measured over a certain amount of time in units of seconds or minutes (e.g., 300 seconds or 5 minutes). In certain embodiments, the benchmarked threshold can be monitored in the context of a persistent condition, where the benchmarked threshold may be configured to be met or exceeded for a predetermined amount of time before an activation is triggered, thus helping ensure that analyte sensor system 308 should indeed wake up. For example, the persistent condition can include consistent-frequency current measurements (e.g., including digital counts in some cases) over a subset of a time duration used for measuring current for activation purposes. For example, this can ensure that the benchmark threshold is not reached based on an undesired anomaly, such as a short duration spike of current (or, e.g., digital counts) within the time period for monitoring current through analyte sensor 10 for purposes of activating analyte sensor system 308.

The measured current (e.g., number of received counts) for analyte sensor 10 may be compared with a benchmark threshold (e.g., X counts, which can be approximately 9000 counts). Upon a determination that the measured current (e.g., number of received counts) meets or exceeds the benchmark threshold (e.g., X counts), processor 535, which may be part of or operation in conjunction with activation detection circuit 520, can initiate an operational mode of analyte sensor system 308. For example, analyte sensor system 308 may begin receiving/obtaining sensor information from analyte sensor 530. In some embodiments, for example, estimated analyte value data is then transmitted to one or more display devices 110, etc. That is, processor 535 can stay active and forward/communicate and/or process the sensor information (e.g., current, digital counts, or the like) to transceiver 510 for communication to one or more display devices 110, partner devices 136, etc. However, if the determination was that the measured current (e.g., number of received digital counts, etc.) did not meet or exceed the benchmark threshold (e.g., X counts), analyte sensor system 308 may remain in a lower power state and/or storage mode. Optionally, in some cases, and subsequent to the determination that the measured current (e.g., number of received counts, or the like) meets or exceeds the benchmark threshold (e.g., count-related threshold), another determination can be made to determine whether the measured value (e.g., number of received counts, etc.) meets or exceeds a second benchmark (e.g., count threshold (U)) for a second period of time (V). This may result in a system that is more robust to false wakeups that might result from anomalies associated with the analyte sensor signal.

Figure 7A:
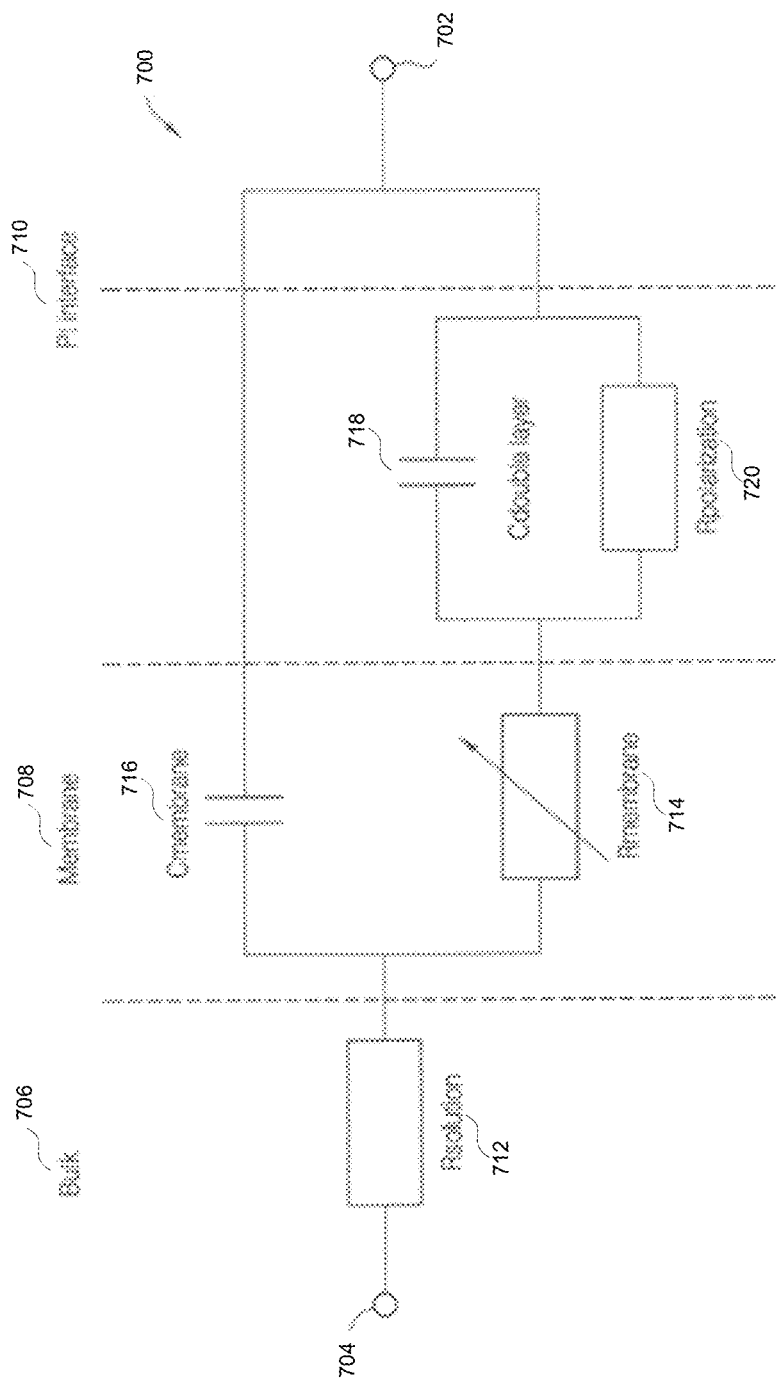
FIG. 7A illustrates an example circuit diagram of an analyte sensor, in accordance with some embodiments.

FIG. 7A is a schematic diagram of equivalent circuit model 700 for analyte sensor 10, in accordance with embodiments of the present disclosure. Sensor circuit model 700 can represent electrical properties of analyte sensor 10, such as an embodiment of a continuous glucose sensor. Circuit 700 includes first terminal 704 (e.g., which may be a working electrode) and second terminal 702 (e.g., which may be a reference electrode). Operatively connected in serial to second terminal 702 is Rsolution 712, representative of a resistance of bulk 706 between first and second terminals 704 and 702. Bulk 706 can be a liquid (e.g., interstitial fluid) or other medium in which analyte sensor 10 is placed, such as a buffer solution in the example of a bench laboratory study, or, in the example of the use as a subcutaneously placed analyte sensor 10, bulk 706 can be representative of the subcutaneous tissue environment between first and second terminals 704 and 702.

Operatively connected to Rsolution 712 is Cmembrane 716, representative of a capacitance of membrane 708 of analyte sensor 10, and Rmembrane 714, representative of a resistance of membrane 708 of analyte sensor 10. A parallel network of Cdouble layer 718 and Rpolarization 720 are operatively connected to Rmembrane 714. The parallel network of Cdouble layer 718 and Rpolarization 720 is representative of the reactions occurring at the surface of a platinum interface of first terminal 704. In particular, Cdouble layer 718 is representative of the charge that is built up when a working electrode (e.g., platinum) is in bulk 706 and Rpolarization 720 is the polarization resistance of the electrochemical reactions that may occur at working electrode interface 710.

In example embodiments, a non-analyte signal is generated using analyte sensor 10 and used for purposes of activating analyte sensor system 308 and/or causing analyte sensor system 308 to exit a lower power mode. One such non-analyte signal includes a signal that may represent certain electrical, physical, or other properties of analyte sensor 10. For example, a stimulus signal may be used to determine certain properties of analyte sensor 10.

According to embodiments, a capacitance of analyte sensor 10 may be detected and used to trigger analyte sensor system 308 to activate and/or exit a lower power state. For example, the capacitance of analyte sensor 10 may change when analyte sensor 10 membrane is hydrated or placed within an environment having a higher or lower humidity. Activation detection circuit 520 may include a circuit that responds to analyte sensor 10 capacitance and drives a time varying signal (e.g., a square wave, voltage step, alternating current signal, or the like) through analyte sensor 10, detecting how that signal may be affected by analyte sensor 10 capacitance. How analyte sensor 10 responds to the driving signal can be indicative of a capacitance associated with analyte sensor 10. For example, a minimum level of capacitance for analyte sensor 10 could be required to detect a threshold response to the driving signal. Accordingly, analyte sensor system 308 can use activation detection circuit 520 to measure a metric indicative of capacitance for analyte sensor 10 and, based on that capacitance metric, a determination can be made as to whether or not analyte sensor 10 has been implanted in a host. It should be appreciated that the measured capacitance can include one or more of Cmembrane 716, Cdouble layer 718 (referencing FIG. 7A by way of example), and other capacitances that may be associated with analyte sensor 10. For example, a driving signal could be passed through analyte sensor 10 between first and second terminals 702 and 704, where the driving signal may then be affected by Cmembrane 716, Cdouble layer 718, and other capacitances that may be associated with analyte sensor 10 and used to approximate those capacitances and/or a total amount of capacitance that may load analyte sensor 10.

Figure 7B:
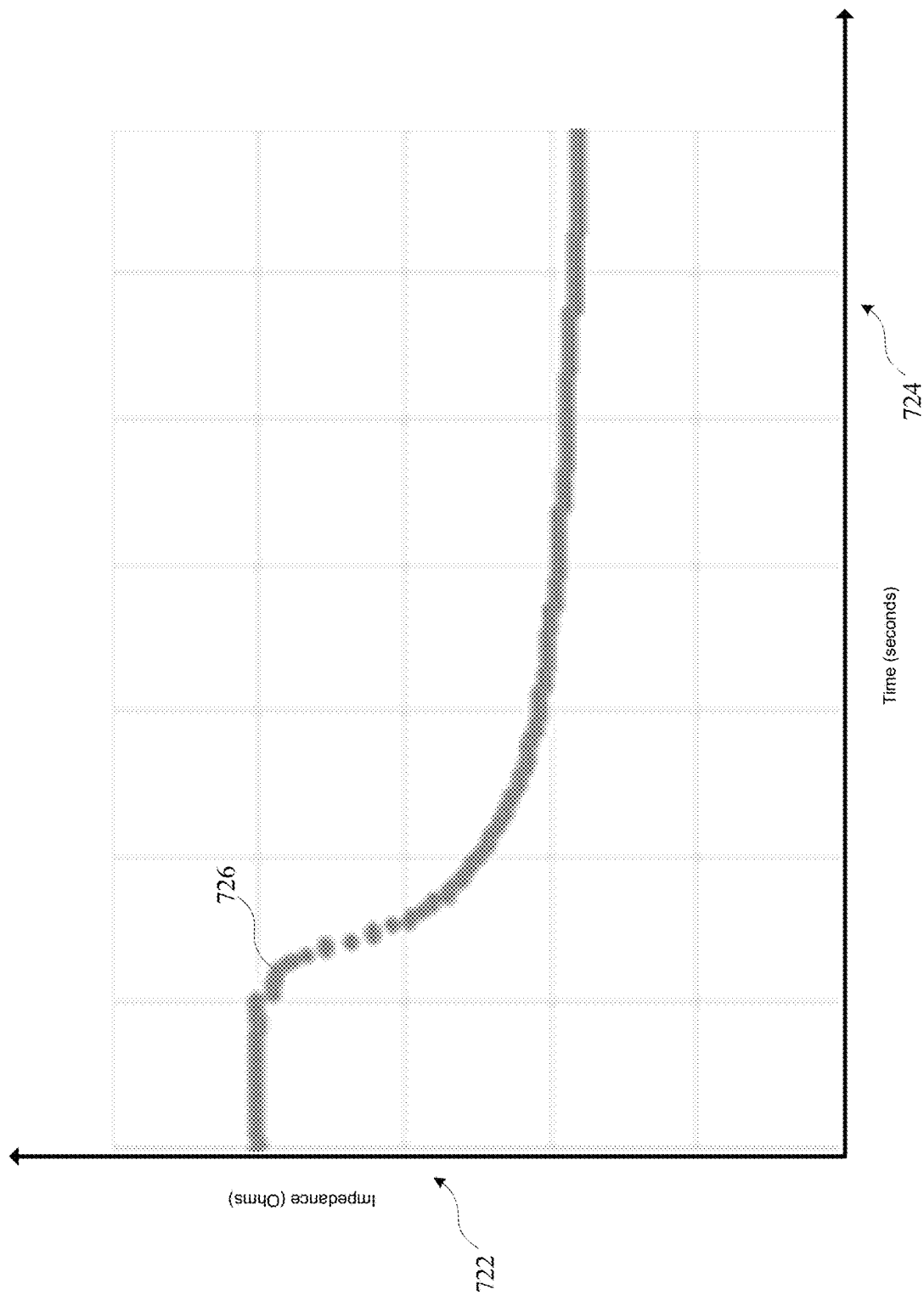
FIG. 7B illustrates an example plot of analyte sensor impedance as a function of time, in accordance with some embodiments.

Impedance is another characteristic of analyte sensor 10 that may be detected and used to trigger analyte sensor system 308 to activate and/or exit a lower power state. FIG. 7B illustrates example plot 726 of analyte sensor 10 impedance value (e.g., in units of Ohms) 722 versus time from implantation 724 (e.g., in units of seconds). As shown, impedance value 722 of analyte sensor 10, after a certain amount of time following implantation (e.g., 30 seconds), may begin to decrease. As further shown, after an initial decay in impedance value 722, impedance value 722 largely stabilizes following a certain amount of time after implantation of analyte sensor 10. The change (e.g., decrease in impedance value 722, or a rate of change of the impedance value, or the like) that may result from implantation of analyte sensor 10 can be used for detecting/triggering activation.

Figure 7C:
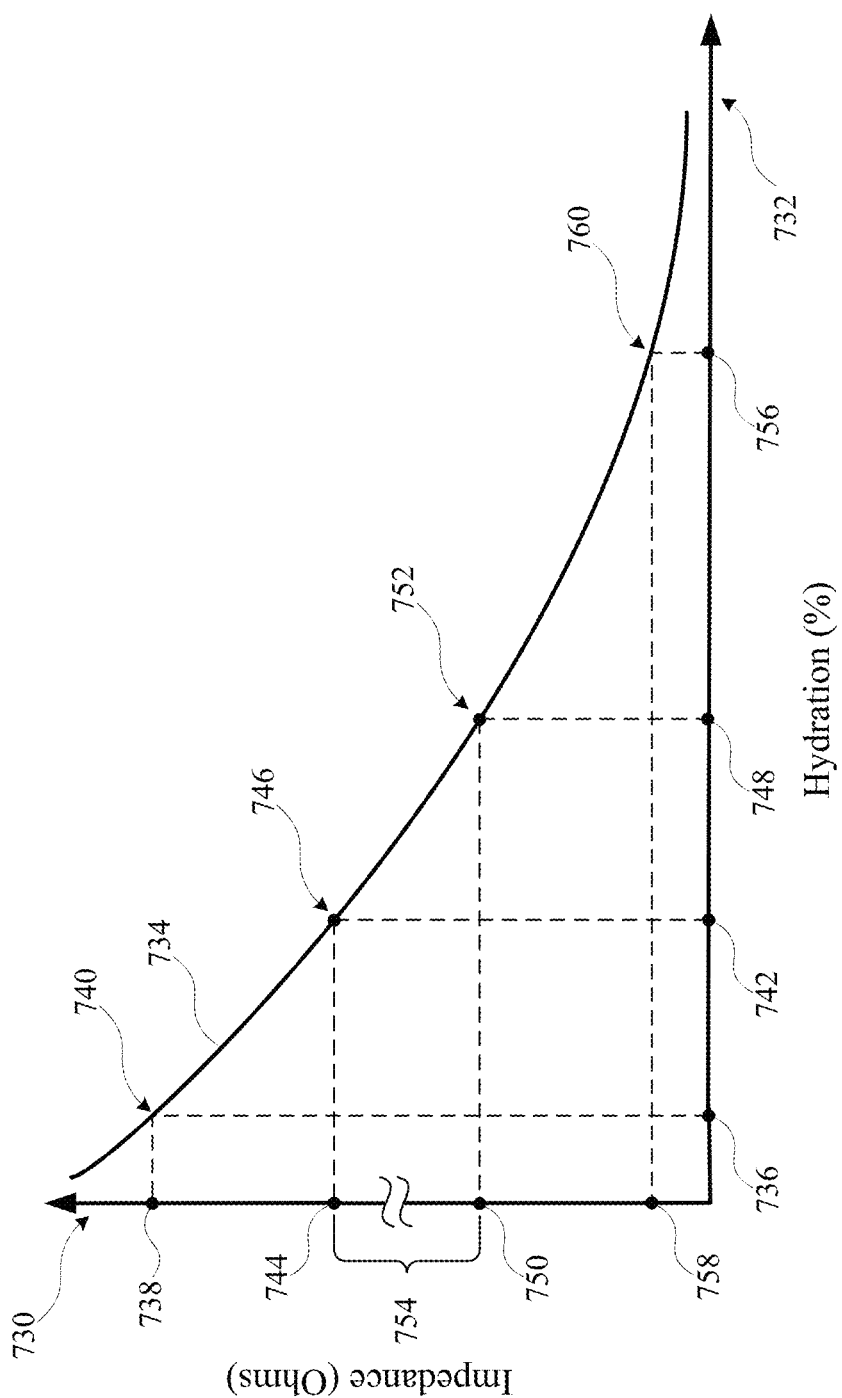
FIG. 7C illustrates an example plot of analyte sensor impedance as a function of time, in accordance with some embodiments.

FIG. 7C shows another example plot 734 of impedance value 730 (e.g., in units of Ohms). FIG. 7C provides a plot of impedance value 730 versus hydration 732 (e.g., in units of %), which may be a hydration associated with a membrane of analyte sensor 10. Generally, humidity outside the human body can cause a membrane hydration level that may be lower than the hydration level that may typically be associated with the membrane when analyte sensor 10 is inside the human body. Accordingly, moisture in an environment, and the hydration levels that may result (e.g. of a membrane of analyte sensor 10), may be used to indicate that analyte sensor 10 has or has not been implanted into the body of a host. Additionally, in some cases, certain environmental conditions (e.g., humidity) may cause activation of analyte sensor system 308 even if analyte sensor 10 has not been inserted into a host's body.

Additionally, measurable electrical characteristics associated with analyte sensor 10 may vary as a function of environmental humidity, moisture, and/or membrane hydration. The variation of such measurable electrical characteristics (e.g., impedance, capacitance, etc.) as a function of humidity, moisture, and/or hydration may in some cases be such that the measurable electrical characteristics can serve as a more reliable indicator for activating analyte sensor system 308 or causing analyte sensor system 308 to exit a lower power state than, for example, directly using humidity, hydration, and/or moisture level. For example, in some cases, humidity, moisture, and/or membrane hydration may increase for reasons other than analyte sensor 10 being inserted into a host (e.g. high moisture levels within packaging for analyte sensor system 308) and may thus trigger a false wakeup of analyte sensor system 308. The relationship between humidity/moisture and certain measurable electrical characteristics of analyte sensor 10 (e.g. impedance, capacitance, etc.) may thus be exploited to more accurately detect analyte sensor 10 insertion events and, in response, activate analyte sensor system 308.

For example, under lower humidity conditions (e.g., 90% RH) impedance may be relatively high (e.g., 10 MΩ). Upon analyte sensor 10 being implanted, however, impedance can decrease, in some cases relatively quickly (e.g., to several hundred kΩ). Accordingly, in embodiments, a change, rate of change, and/or threshold impedance value (e.g., of approximately 300 to 500 kΩ by way of specific but non-limiting illustration) can be used to distinguish between high humidity conditions that may occur in a non-insertion environment outside a host's body, on the one hand, and moisture conditions that may occur in relation to analyte sensor 10 being implanted within the host's body, on the other hand. This may help to prevent (or resist) environmental conditions from triggering analyte sensor system 308 to activate or exit a lower power state when doing so is not desired. The desired level for the impedance threshold can be based on the time that may be allotted for the wakeup trigger time window for analyte sensor system 308 after insertion of analyte sensor 10, which may be a trade-off made against state robustness to false wakeup from, for example, noise, signal magnitude, circuit measurement inaccuracies, etc. Examples of feasible wake up trigger times include but are not limited to approximately 30 seconds or less to approximately 60 seconds or more.

As shown in FIG. 7C, at hydration 736 (e.g., in units of %) prior to implantation of analyte sensor system 10, point 740 of plot 734 corresponds to impedance value 738 (e.g., in 11). Additionally, at hydration 756 following implantation of analyte sensor 10, point 760 corresponds to impedance value 758. In embodiments, impedance value 758 may be distinctly lower than impedance value 738, such that a range of impedance values between impedance value 744 and impedance value 750, corresponding respectively to points 746 and 752 on plot 734, may be used as thresholds for detecting implantation of analyte sensor 10 and may thus be used to trigger analyte sensor system 308 to activate and/or exit a lower power state. In additional or other examples, a gradient or derivative of impedance value as a function of hydration can be monitored to detect analyte sensor 10 implantation. Thus, for example, the impedance of analyte sensor 10 can be monitored, and when the impedance crosses a threshold value for impedance (e.g., or meets a threshold derivative, gradient, or other condition), activation or a change of state of analyte sensor system 308 can be triggered. In a specific example, analyte sensor 10 may have an impedance associated therewith of approximately 10 MΩ before insertion of analyte sensor 10, at a relatively lower hydration value (e.g., within a range of values typical for environmental humidity outside a host's body or in a certain environment). Then, the impedance value of analyte sensor 10 may drop to approximately 100 kΩ as hydration increases after analyte sensor 10 is inserted into a user's body.

The impedance associated with analyte sensor 10 may be measured using various techniques, including, for example, using a voltage or current step or other function, etc., using electro chemical impedance spectroscopy (e.g., as described in U.S. Pat. No. 9,801,575, the contents of which are hereby incorporated by reference in their entirety), or using any other known method. By way of example, activation detection circuit 520 may include a driver circuit (e.g., function generator, oscillator, or the like) operation to generate the step function or other function or signal that may be used for measuring analyte sensor 10 impedance. For example, as the voltage associated with the step function or other signal is applied to analyte sensor 10, a resulting current between terminals of analyte sensor 10 can be detected using activation detection circuit 520. In example implementations, the relationship between the applied voltage and resulting current can then be used to calculate an impedance for analyte sensor 10.

Generally, to reduce/minimize battery power usage and avoid sending more current through analyte sensor 10 than is necessary or appropriate, any impedance measurement done for activation purposes should use a relatively low amplitude waveform (e.g., less than approximately 50 mV) and preferably zero net current (e.g., centered around 0 V of electrode voltage bias). In embodiments, as mentioned above, measurements indicative of impedance can be characterized using activation detection circuit 520 through applying a voltage (e.g., step function) to analyte sensor 10. The magnitude of the resulting current flow (which, e.g., may include a current spike) may be inversely related to an impedance of the membrane of analyte sensor 10. Thus, using Ohm's law, for example and not limitation, the impedance may be determined by monitoring voltages, currents, and/or digital counts of either or both.

Activation detection circuit 520 may include circuitry to detect whether the impedance is above or below a set level. Such circuitry will be discussed in further detail below in connection with at least FIGS. 8A and 12-14. Regarding FIG. 8A, at a high level, the circuitry can capture positive current spikes using a switch that may be driven using a voltage source that may apply, for example, a square wave or other waveform to analyte sensor 10. The positive currents may then be used to charge a capacitor. The voltage that may develop over the capacitor may represent a measure of the impedance of analyte sensor 10 (e.g., as measured based on a voltage divider that may be arranged between an impedance of analyte sensor 10 and a known impedance). By using a voltage comparator circuit set at a desired level, insertion of analyte sensor 10 can be determined and used to trigger analyte sensor system 308 to exit a lower power state. Such circuits may be designed and integrated into a chip that can be operated at very low power (e.g., less than 1 uA during lower power state). Upon detecting implantation of analyte sensor 10, the chip and/or circuit can then send a control signal to processor 535 to cause analyte sensor system 308 to exit the lower power state.

In embodiments, voltage to current amplifiers and additional switches may be used to decouple analyte sensor 10 from a detection circuit after analyte sensor system 308 exits the lower power state. It should also be noted that at high humidity conditions (e.g., such as may occur during storage), the net current through analyte sensor 10 may be limited. This can provide an advantage over techniques for activation of analyte sensor system 308 that apply a fixed bias to analyte sensor 10 (e.g., a voltage, such as 0.6 V). When such techniques are used, under high humidity conditions, current that flows through analyte sensor 10 as a result of the application of the fixed bias may consume an undesirable amount of power and/or may impact the performance of analyte sensor 10.

Figure 8A:
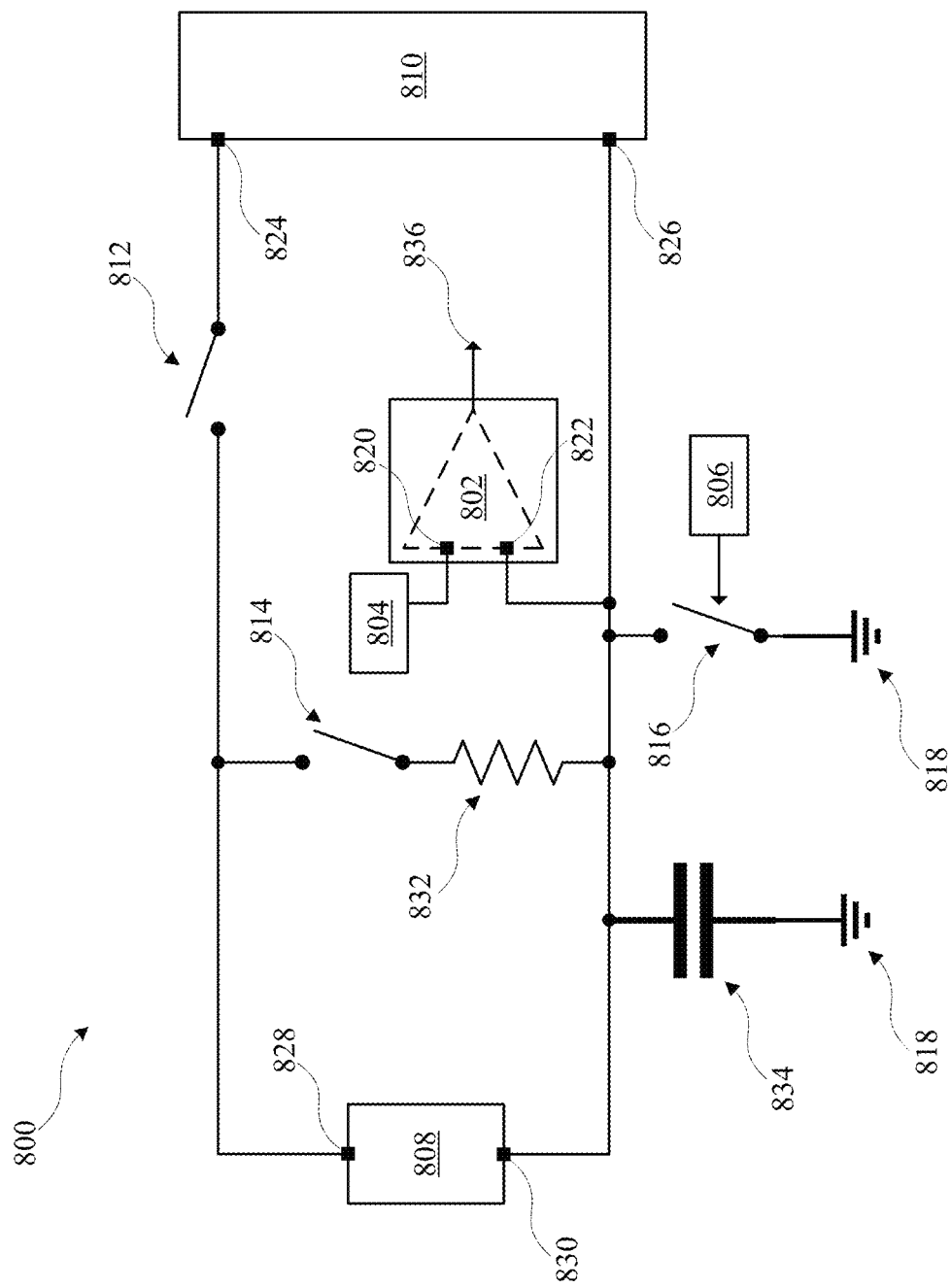
FIG. 8A illustrates aspects of an example activation detection circuit, in accordance with some embodiments.

Turning now to FIG. 8A, an example activation detection circuit 800 is shown, in accordance with embodiments of the present disclosure. Circuit 800 may be used, for example, to detect current in a lower power wakeup circuit that can be used for activating analyte sensor system 308. At a high level, and with reference to FIG. 5 by way of example and context for certain embodiments, circuit 800 can use an inrush (e.g., charging) current through a capacitance of analyte sensor 530 to generate voltage pulses. The voltage pulses may be monitored by a detection circuit and, if the pulses satisfy one or more conditions, analyte sensor system 308 may be triggered to exit a lower power state. By way of example, in certain embodiments, a predetermined number of pulses exceeding a voltage threshold may trigger activation of analyte sensor system 308. Additional examples are described below.

Components such as one or more switches and one or more current limiting resistors may be used in circuit 800 to provide a more accurately detectable analyte sensor 530 implantation event and thus more robust control for activating analyte sensor system 308 or causing analyte sensor system 308 to exit a lower power mode. For example, at a first time, a switch can be used to couple a first terminal of analyte sensor 530 to a potentiostat or other measurement device or circuit. A detection circuit may in certain examples include an amplifying element (such as, e.g., a comparator, low-noise amplifier, other amplifier, or the like) and/or other circuitry. The detection circuit can be used to detect whether a voltage generated using circuit 800, for example, based on (e.g., charging) current that may flow through capacitance of analyte sensor 530, exceeds a threshold or otherwise meets one or more conditions. If the voltage exceeds or otherwise meets the condition(s), activation of analyte sensor system 308 can be triggered. For example, such a voltage can be generated using a current-to-voltage conversion effect of components that may be included in or used by circuit 800, such as capacitor 834, switch element 818, and/or driver circuit 806.

And, for example, at a second time, the switch that may be used to couple the first terminal of analyte sensor 530 to the measurement device (e.g., potentiostat) can be opened or put in a high impedance state, to decouple the first terminal of analyte sensor 530 from the measurement device/potentiostat, while a second switch can couple the first and second terminals of analyte sensor 530 together, for example, through a current limiting resistor, to at least substantially discharge analyte sensor 530 capacitance. In this manner the voltage potential that may be present across analyte sensor 530 can be set, reset, and/or zeroed out. This can effectively reset the circuit so that the charging current inrush event through analyte sensor 530 capacitance can be repeated, thus enabling another detectable event and providing a more robust activation detection mechanism for analyte sensor system 308. In some instances, this activation detection mechanism can more reliably distinguish between multiple electrical characteristics that may be measured for analyte sensor 530, where some such electrical characteristics may be indicative of a hydration state of analyte sensor 530 and other such characteristics may merely indicate a high humidity environment, and activate analyte sensor system 308 more appropriately, reliably, or accurately.

More specifically, FIG. 8A shows that circuit 800 may include analyte sensor 808 and measurement device 810 (e.g., a potentiostat). It will be appreciated by one of skill upon studying the present disclosure that in certain embodiments analyte sensor 808 may be similar, substantially similar, or the same as, for example, analyte sensor 530 referenced in connection with FIG. 5. In certain embodiments, analyte sensor 808 may be at least partially different than analyte sensor 530, depending upon the contexts and/or applications in which analyte sensors 530 and/or 808 may be used. Measurement device 810 may be used to apply a bias to analyte sensor 808 and/or to gather information from analyte sensor 808 that can be used to calculate a level of an analyte in a host into whom analyte sensor 808 has been implanted.

In addition, circuit 800 may include capacitive element 834, and optionally includes resistive element 832. Circuit 800 may also include detection circuit 802, which may in some cases be, use, or include an amplifying element (e.g., a comparator), for example. Additionally, circuit 800 may include one or more of reference voltage 804, reference voltage 818, and driver circuit 806, which may be, for example, a clock-based driver. It should be appreciated that one or more of reference voltages 804 and 818 may be substituted for other reference signals. It should also be appreciated that driver circuit 806 may be driven by signals other than clock signals.

In embodiments, current based activation techniques for analyte sensor system 308 may be performed using a circuit similar to circuit 800 shown in FIG. 8A. However, certain modifications may be made in connection with some such embodiments. For example, switch element 812 may not be present in circuit 800, or may be bypassed or short circuited, for example. Switch element 814 may also not be present or may be effectively removed from circuit 800, and/or may be placed in a high impedance or open circuit state. In such cases, resistive element 832 may also be effectively removed from circuit 800. It should be appreciated that other means may be employed to effectively remove and/or bypass resistive element 832. In embodiments, implantation of analyte sensor 808 may still be determined/monitored based upon detecting certain (e.g., sufficient) current flow(s) between first and second terminals 828 and 830 of analyte sensor 808.

Example features of such a modified or similar version of circuit 800 are now provided, as follows. Measurement device 810 may apply a potential across terminals 828 and 830 of analyte sensor 830 (e.g., a substantially continual voltage). For example, terminal 828 may be placed at a higher potential than terminal 830, such that current flow through analyte sensor 808 may be sourced through terminal 824 of measurement device 810 (e.g., a potentiostat in some cases). Additionally, for example, terminal 826 of measurement device 810 and terminal 830 of analyte sensor 808 may be coupled to one another and/or to current-to-voltage conversion circuitry.

In embodiments, the current-to-voltage conversion circuitry may include capacitive element 834 that may be coupled at a first end to terminals 826 and 830, and at a second end to reference voltage 818 (e.g., ground). The first end of capacitive element may also be coupled to switching element 816. Switching element 816 may be driven by driving circuit 806, which may be, include, and/or use a clock-based or other signal type driver. Switching element 816 may in this manner cause terminals 826 and 830 to be alternatively coupled to and decoupled from reference voltage 818. Terminals 826 and 830 may be coupled to and decoupled from reference voltage 818 periodically according to a configurable, programmable, adaptable, and/or variable interval/frequency (e.g., 10 Hz). In some cases, driver circuit 806 may cause the coupling/decoupling of terminals 826 and 830 to/from reference voltage 818 to be aperiodic, asynchronous, and/or event-driven.

In one example, when switch element 816 is placed in a higher impedance state or is open, for example at a first time, terminals 826 and 830 may be disconnected or decoupled from reference voltage 818 (e.g., may be floating). Thus, current flowing through a capacitance of analyte sensor 808 may effectively be delivered to capacitive element 834 as charging current. The charging current in turn may cause a voltage potential to develop across capacitive element 834. When switch element 816 is placed in a lower impedance or conductive state or is closed, for example at a second time, terminals 826 and 830 may be connected or coupled, in some cases directly, to reference voltage 818 (e.g., ground). In this configuration, the charge that may be stored in capacitive element 834 may be at least substantially discharged (e.g., to ground), such that the voltage potential that may have developed across capacitive element 834 may be returned/reset to at least close to the potential of reference voltage 818 (e.g., ground or 0 V). Accordingly, in this example, when current flows through capacitance of analyte sensor 808, due to the action of switch element 816, the resultant voltage signal waveform that may be present at terminals 826 and 830 may represent a series of voltage pulses (e.g., voltages across capacitive element 834 as a function of time), where such pulses may be proportional to a magnitude of current flow through the capacitance of analyte sensor 808.

Continuing the example, in circuit 800, input 822 of detection circuit 802 (e.g., a voltage detection circuit, which may be implemented as an amplifying element, comparator, other circuitry, or the like) may be coupled to terminals 826 and 830. In embodiments, detection circuit 802 is operable to compare the voltage across capacitive element 834 to reference voltage 804, which may be configurable, programmable, variable, adaptable, etc. Detection circuit 802 may be further operable to produce output 836 that may be used to trigger activation of, e.g., analyte sensor system 308, if certain condition(s) are met (e.g., if the voltage across capacitive element 834 is above, below, or within a range of reference voltage 804, or is exhibiting a particular trend, etc.). It should be noted that reference voltage 804 can be configured based on calibration, can be set according to a predetermined value/characteristic, and/or can be configured on the fly or based on environmental conditions experienced by analyte sensor system 308 in the field. Moreover, detection circuit 802 may include and/or use configurable digital logic circuitry (not shown in FIG. 8A) operable to count and/or otherwise characterize or measure a number of sequential voltage pulses that may satisfy (e.g., meet or exceed) a threshold. For example, if the number and/or characterization of measured/monitored pulses satisfies a configurable condition (e.g., threshold number/magnitude), output 836 may indicate that analyte sensor system 308 should be activated or caused or triggered to exit a lower power state.

In certain cases, however, the above-described example may be more particularly suited for use in conjunction with certain electrical models of analyte sensor 808. For example, the above-described example circuit may be more suited to implementations where analyte sensor 808 is modeled as a substantially or purely resistive load between terminals 828 and 830 of analyte sensor 808. But, for certain examples, this substantially resistive load may not be an approximate representation of analyte sensor 808. By way of illustration, in the case of a substantially or purely resistive load, the voltage pulses that may develop across capacitive element 834 as a result of charging current may be of a substantially constant amplitude for a given substantially constant current. Therefore, the amplitude of the voltage pulses may increase proportionally with increasing current.

Figure 8B:
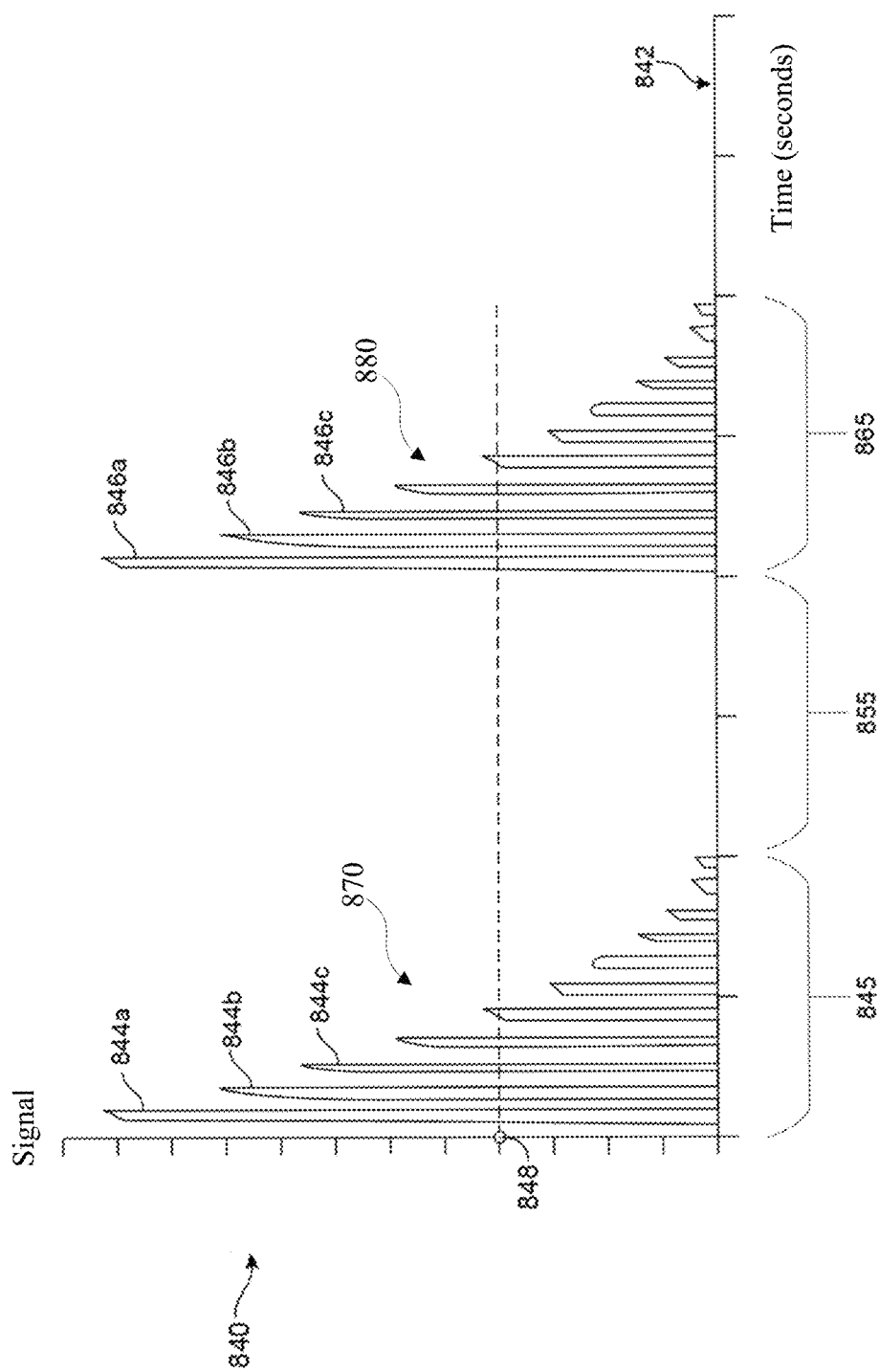
FIG. 8B illustrates an example plot of an analyte sensor signal, in accordance with some embodiments.

As described above in connection with FIG. 7A, however, in embodiments, the electrical behavior of analyte sensor 808 may not be as accurately modeled by a substantially or purely resistive load. Instead, it may be more accurate to electrically model analyte sensor 808 using a more complex passive circuit model, for example, as is shown in FIG. 7A, that includes both capacitors and resistors and that may include other elements. For example, when the relatively larger capacitance Cdouble layer 718 of analyte sensor 808 is included in the electrical model that may be employed, circuit 800 may operate in a different fashion when terminals 828 and 830 of analyte sensor 808 are first connected within circuit 800. In some cases, the difference may be significant or appreciable. By way of illustration, instead of a constant amplitude voltage pulse sequence or train that may result when the resistive model/load is employed (e.g., as describe in connection with the above example), the waveform characteristic for the voltage across capacitive element 834 may be substantially affected (and in some cases dominated) by the initial inrush of charging current that may flow through the capacitance of analyte sensor 808. This may result in (e.g., a series) of voltage pulses that initially have a larger amplitude and then subsequently have a decreasing amplitude. The amplitude may decrease rapidly in some cases, and may decrease substantially, for example, according to an exponential decay that may be associated with a resistive/capacitive (RC) characteristic of the electrical equivalent model for analyte sensor 808 illustrated by way of example in FIG. 7A. Here, reference is made by way of example to FIG. 8B, which is discussed in further detail below. As shown in FIG. 8B, for example, the pulses that may be included in waveform 870 exhibit an exponential decay during time period 845. It should be appreciated, however, that if the resistive model is used for analyte sensor 808, this decay may not be present, and instead, the pulses of waveform 870 may be relatively constant in amplitude.

Furthermore, once the capacitance of analyte sensor 808 is charged and the currently flow is primarily due to steady state current, the operation of the current-to-voltage circuit may remain significantly affected by the presence of the charged capacitor. For example, if a more complex electrical model is used, the amplitude of the residual voltage pulses that may be measurable across capacitive element 834 for a given steady state current may be meaningfully lower than the equivalent steady state current that would be present under the resistive load electrical model for analyte sensor 808. Moreover, the proportional difference in magnitude of the corresponding voltage waveforms for the two different currents may no longer be sufficiently differentiated by detection circuit 802 under normal circumstances. For example, detection circuit 802 may not be capable of as accurately detecting threshold crossings etc., due to the relatively small or diminished difference in the steady state voltage pulse amplitude that may result when the electrical model of FIG. 7A is employed.

Accordingly, in view of the above, it should be appreciated that the example configuration of circuit 800 described above may produce steady state currents that may not result in voltage pulse waveforms of sufficient magnitude for detection or differentiation by detection circuit 802. This example configuration of circuit 800 may thus not be as conducive to accurate and robust activation of analyte sensor system 308. For example, there may be only a single or small number of opportunities to generate a sufficient voltage waveform that can be more easily/accurately/reliably detected by detection circuit 802. For instance, the initial relatively large voltage pulse that may result from initial inrush of charging current may provide only a single detection event. And if this initial relatively large pulse or pulses are not detected by detection circuit 802 or analyte sensor system 308 is not activated as a result of the initial pulse(s) (e.g., because analyte sensor 808 may not be sufficiently hydrated at time of connection to circuit 800), circuit 800 may not have another sufficiently detectable opportunity to detect/assess implantation of analyte sensor 808.

Accordingly, embodiments of the present disclosure include a configuration of circuit 800 that is resettable by virtue of circuit components such as switches and other elements. For example, referring further to FIG. 8A, circuit 800 may include switch elements 812 and 814. Switch elements 812, 814, and 816 may be implemented using electrical components, including discrete or integrated components, such as transistors or other passive/active devices (e.g., FET switches, etc.). As will be discussed below in further detail, switch elements 812 and 814 may be complementary, such that when one switch element is closed, the other may be open and vice versa. Switch elements 812 and 814 may be controlled using a clock or other signal driver, and in some cases this clock may be derived from the clock or other source/driving signal used for driver circuit 806. In embodiments, switch elements 812 and 814 may be controlled by a clock or other source with a lower frequency than the clock or other source that may be used for driver circuit 806. For example, the (e.g., clock) frequency for switch elements 812 and 814 may be a fraction of the (e.g., clock) frequency for switching element 816, where the value of the fraction that may be used can be configurable, programmable, adaptable, and/or variable. Examples/options for the fraction may include, in some cases, ⅒, 1/20, 1/40, 1/80 etc. Thus, per these examples/options, switch elements 812 and 814 may change state every 10, 20, 40, or 80 cycles of the clock for switch element 816. Other ratios and relationships that can be set up with respect to driver circuit 806 and the control of switch elements 812 and 814 will be appreciated upon studying the present disclosure.

Output 836 of detection circuit 802 may be coupled to, for example, processor 535 of analyte sensor system 308, such that output 836 may be used for activation or triggering of analyte sensor system 308. Circuit 800 may be implemented within or in conjunction with activation detection circuit 520. When circuit 800 is implemented as or as part of activation detection circuit 520, output 836 may be coupled to processor 535, such that when signaled to do so, processor 535 may be used to cause or trigger analyte sensor system 308 to wake up or exit a lower power state. As alluded to above, analyte sensor 808 may include first and second terminals 828 and 830. Detection circuit 802 may include reference terminal 820 and input terminal 822. Measurement device 810 may include first terminal 824 and second terminal 826.

As mentioned, circuit 800 may be used to control activation of analyte sensor system 308. Detection circuit 802 may indicate whether a signal at input terminal 822 meets one or more conditions. For example, the condition may be or include one or more threshold voltages that may be set using reference voltage(s) 804 applied to reference terminal(s) 820 of detection circuit 802. The voltage(s) at input terminal(s) 822 may be indicative of a current that may flow between first and second terminals 828 and 830 of analyte sensor 808 (e.g., as described above, circuit elements of circuit 800, including capacitive element 834, may be used to effectively convert current through analyte sensor 808 to a voltage). For example, the condition(s) may be, use, and/or include a threshold that is programmable, adaptable, variable, and/or configurable, etc.

In certain instances, the condition(s) can be configured such that the condition(s) may be met when the voltage(s) of one or more signals provided at input terminal 822 is (are) indicative of current that may flow between first and second terminals 828 and 830 of analyte sensor 808 when analyte sensor 808 is implanted in a host or under other conditions. In such cases, output(s) 836 of detection circuit 802 may be used to trigger analyte sensor system 308 to exit a lower power state by indicating that this signal(s) at input terminal 822 satisfies(y) the condition(s) (e.g., depending on the level(s) of the output signal(s) 836). For example, in some cases, output(s) 836 of detection circuit 802 may include binary levels, multiple discrete levels, and/or continuous or substantially continuous or analog values that may be used to trigger activation of analyte sensor system 308 into one or more triggered or active states. In some cases, the state that analyte sensor system 308 enters may depend upon characteristics (e.g., levels, trends, etc.) of output 836. In embodiments, the condition(s) may be configured to be met when a certain number of voltage pulses satisfy (e.g., meet or exceed) the threshold(s), or when a certain number of sets of voltage pulses exceed the threshold(s), as will be discussed further in connection with FIG. 8B.

Switch element 812 may be used to couple or decouple first terminal 828 of analyte sensor 808 to/from first terminal 824 of measurement device 810 (e.g., a potentiostat). Switch element 814 may be used to couple or decouple first terminal 828 of analyte sensor 808 to/from input terminal 822 of detection circuit 802 (optionally through resistive element 832). Input terminal 822 of detection circuit 802 may be coupled to second terminal 830 of analyte sensor 808 and to second terminal 826 of measurement device 810.

At a first time, switch element 812 may be closed or placed in a conductive state, coupling first terminal 828 of analyte sensor 808 to first terminal 824 of measurement device 810. Switch element 814 may be open or placed in a high impedance state at this time, decoupling input terminal 822 of detection circuit 802 from first terminal 828 of analyte sensor 808. Thus, at the first time, measurement device 810 may be used in connection with gathering information that may be used to calculate the level of the analyte in the host. Furthermore, a voltage waveform generated using circuit 800 (e.g., as alluded to above), and specifically using charging current that may flow through a capacitance of analyte sensor 808, may be fed to the terminal 822 and monitored and compared to reference voltage 804 using detection circuit 802 (e.g., which may be or include an amplifying element and/or a comparator or other circuit).

At a second time, switch element 812 may be open or set to a high impedance state, thus decoupling first terminal 828 of analyte sensor 808 from first terminal 824 of measurement device 810. Switch element 814 may be closed or set to a low impedance or conductive state at this time, thus coupling second terminal 830 of analyte sensor 808 to first terminal 828 of analyte sensor 808 (optionally through resistive element 832 in some cases). This may reduce or possibly eliminate the voltage potential present across analyte sensor 808 and at least substantially discharge the stored charge of a capacitance of analyte sensor 808 (see, e.g., FIG. 7A) using a switching action of driver 806 and switch element 816 to create a conductive path to reference voltage 818. As mentioned, resistive element 832 may optionally be used to limit current that may flow through switch elements 814 and/or 816 when switch elements 814 and/or 816 is/are closed or placed in a conductive or low impedance state.

Capacitive element 834 may be coupled between input terminal 822 of detection circuit 802 (which is shown in this example as being coupled to second terminal 830 of analyte sensor 808) and voltage reference 818 (e.g., ground). Switch element 816 may be driven by, or otherwise obtain as an input, a signal from driver circuit 806 (e.g., a clock or other signal), such that switch element 816 may periodically couple input terminal 822 of detection circuit 802 to reference 818. Where, for example, voltage reference 818 is ground, this may at least substantially discharge capacitive element 834, as further referenced/discussed in connection with FIG. 8B. As mentioned, capacitive element 834 in conjunction with driver circuit 806 and/or switch element 816 may be used to implement a current-to-voltage circuit. The current-to-voltage circuit may be operable to convert current that may flow through analyte sensor 808 into a voltage (e.g., waveform) that can be measured or otherwise characterized using detection circuit 802 in connection with determining whether a threshold/condition has been met or satisfied, as referenced above, and further in connection with activating and/or triggering analyte sensor system 308 to change states.

In embodiments, switch elements 812 and 814 may be driven by a common signal that may be inverted for one of either switch element 812 or switch element 814. Alternatively, switch elements 812 and 814 may be driven by a common signal but the devices used for switches 812 and 814 may have opposite polarities. For example, in embodiments, switch elements 812 and 814 may be driven such that they are configured to be in opposite (e.g., impedance) states at a given time. Thus, switch elements 812 and 814 may be configured such that in large part, when switch element 812 is closed, switch element 814 will be open, and vice versa. Configured in this manner, switch elements 812 and 814 can be used to at least substantially discharge a capacitance associated with analyte sensor 808. As such, the initial inrush of current through the capacitance of analyte sensor 808 that may typically be associated with implantation of analyte sensor 808 into a host's body can be largely recreated and used to generate additional voltage pulses that may be monitored for purposes of activating analyte sensor system 308 and/or causing the same to exit a lower power state. Thus, in the situation when the current rush resulting from implantation of analyte sensor 808 does not trigger activation, switch elements 812 and 814 can be used to effectively reset circuit 800 so that another monitorable current rush may occur and be used to trigger activation of analyte sensor system 308.

Additionally/alternatively, to allow for flexibility, tuning, configuration, and/or optimization, the timing for controlling switch elements 812 and 814 to be in different states may predetermined, programmable, adaptable, variable, and/or configurable, such that switch elements 812 and/or 814 may be placed in particular states/modes in accordance with various durations/intervals/frequencies/etc. and/or a duty cycles and the like. Such timing control may be implemented using and/or derived from driver circuit 806, such that, for example, every given number of cycles of driver circuit 806, the state of switch elements 812 and 814 can change and/or be maintained for a selectable/controllable duration.

FIG. 8B illustrates an example plot of an analyte sensor 808 signal (e.g., voltage, current, etc.) according to embodiments of the disclosure. Waveforms 870 and 880 may represent signals (e.g., voltages, current, etc.) 840 as a function of time 842 (e.g., in seconds), where such signals may be those present on or fed to input terminal 822 of detection circuit 802 in circuit 800 (referencing FIG. 8A by way of example). Reference voltage 848 may be set such that when a voltage or other signal present on input terminal 822 of detection circuit 802 meets, exceeds, or crosses reference voltage 848, output 836 of detection circuit 802 can be used to trigger activation of analyte sensor system 308, as mentioned above. As shown in FIG. 8B, during the time between the end of waveform 870 and the beginning of waveform 880, the signal (e.g., voltage) on input terminal 822 of detection circuit 802 may have been at least substantially discharged or reset by, among other things, switch element 814 and/or switch element 816 being closed. Resetting the voltage across analyte sensor 808 can enable circuit 800 to monitor additional detection events in which the voltage on input terminal 822 may cross, meet, or exceed reference voltage 848.

As shown in FIG. 8B, waveform 870 may include pulses 844a, 844b, and 844c, and as shown can include additional pulses (including pulses not explicitly illustrated). By way of non-limiting example, driver circuit 806 may provide a clock (e.g., square wave, sine wave, etc.) or other signal for driving switch element 816. The period of the clock signal may be thought of as the spacing between each of pulses 844a, 844b, and 844c. In certain examples, driver circuit 806 may provide an aperiodic, asynchronous, and/or event-driven signal for controlling the operation of switch element 816.

By way of non-limiting example, waveform 870 may have a duration of a certain time period 845, which may in some cases be approximately one second, and the period of the clock signal from driver circuit 806 may be approximately 100 msec. As further illustrated, after the initial current rush and corresponding (e.g., voltage) pulse 844a of waveform 870 that may result in connection with implantation of analyte sensor 808 into a host, each successive pulse 844b, 844c, etc. may decrease in amplitude, for example, according to a decay profile that may be associated with an effective time constant (e.g., RC time constant, as described above) of analyte sensor 808. Hence, as described above, switch elements 812 and 814 may be used to largely recreate the initial current rush used to form a pulse with a certain magnitude (e.g., pulse 844a). This is shown for example by waveform 880, which may include pulses 846a, 846b, 846c, etc.

When switch elements 812 and 814 are set in the fashion described above, waveform 870 may drop to or near ground or another reference voltage, as represented at time period 855. In embodiments, time period 855 may be approximately one second (e.g., or any other amount of time that is approximately and/or sufficiently long enough to substantially and/or fully discharge the capacitance of analyte sensor 808), after which waveform 880 and pulse 846a can be measured according to the states of switch elements 812 and 814. Waveform 880 may then be monitored in the above-described manner for activating analyte sensor system 308.

With respect to the one or more conditions that may be used for activating analyte sensor system 308 in connection with circuit 800, many variations are contemplated in connection with the present disclosure. For example, a single pulse, such as pulse 844*a*, meeting, exceeding, and/or crossing threshold 848 or otherwise satisfying a condition may trigger activation of analyte sensor system 308. In embodiments, a predefined number of pulses 844*a*, 844*b*, 844*c* meeting, exceeding, and/or crossing threshold 848 or otherwise satisfying a condition may trigger activation. In some cases, a certain number of pulses from more than one waveform (e.g., waveform 870, 880, etc.), or different respective numbers of pulses (e.g., 844*a*, 844*b*, etc., and 846*a*, 846*b*, etc.) for each waveform 870, 880 may be used for triggering activation. In certain examples, if the number of pulses from waveform 870 that meet a condition does not result in activation, one or more pulses from waveform 880 may be monitored for activation purposes. In some cases, a certain number of pulses exceeding threshold 848 by a certain amount may trigger activation of analyte sensor system 308. In embodiments, if a first condition is not met in connection with detection circuit measuring pulses of waveform 870, a second (e.g., modified) condition may be used for monitoring pulses of waveform 880.

In embodiments, if analyte sensor system 308 is activated and/or triggered to exit a lower power state in response to waveform 870, waveform 880 may in certain cases not need to be generated. In other cases, more than one waveform 870, 880, etc. may be used for activations purposes, and subsequent waveforms other than waveforms 870, 880 (not shown in FIG. 8B) may not need to be generated. In some cases, if analyte sensor 308 is not activated in response to at least one of waveforms 870, 880, etc., additional waveforms may continually be generated. In embodiments, after a configurable number of waveforms have been generated without analyte sensor system 308 being activated, waveform generation may be at least temporarily suspended, including in some cases for a predetermined, configurable, and/or event-based amount of time. Accordingly, in certain embodiments, the ability to essentially reset circuit 800 can enable more robust activation detection schemes as discussed above/herein.

Additionally, with further reference to FIG. 8B, in certain embodiments, the respective durations of time periods 845, 855, and 865 may be varied together or independently. For example, time periods 845 and 865 may be thought of as an active (e.g., default) state, and time period 855 may be thought of as a reset or inactive state with respect to the generation of pulses. In examples, the duration or duty cycle of the active state (e.g., during time periods 845 and/or 865) and the reset state (e.g., during time period 855) may be configurable, including on the fly. In some cases, the duty cycle may be configured to be offset, such that circuit 800 may remain in the reset state longer than in the active state or vice versa.

For example, it may be beneficial in some circumstances to increase the duration of the reset cycle relative to the active state. This may better provide the capacitance of analyte sensor 808 sufficient time to more fully discharge between two successive active cycles (e.g., between the end of time period 845 and the beginning of time period 865). This may facilitate a more consistent, repeatable, and/or accurately detectable initial charging current response and corresponding voltage pulse waveform. Here, it should be noted that any number of waveforms 870, 880 may be repeated in the context of FIG. 8B. The length of reset states between various such waveforms may be varied, for example, as between two sets waveforms associated with active states. In some cases, the length of the reset state(s) may be configurable, variable, adaptable, and/or programmable, for example, the length may be changed in response to detection circuit 802 not triggering activation of analyte sensor system 308 after a certain amount of time has passed and/or under the presence of other conditions that may be monitored using analyte sensor system 308 as described herein (e.g., accelerometer or hydration related conditions). Additionally, the length of the active (or reset) states may be varied from active state to active state (or reset state to reset state), or on any other basis.

In one example, when switch element 812 is closed and switch element 814 is open, circuit 800 may be in the active state. When switch element 814 is closed and switch element 812 is open, circuit 800 may be in the reset state. In the reset state, in this example, analyte sensor 808 may be disconnected/decoupled from terminal 824. As such, there may be no power applied to analyte sensor 808. At the same time, switch element 814, upon being closed, may connect/couple terminals 828 and 830 to one another, optionally via resistive element 832 (e.g., which may act as a current limiter). In this manner, the charge that may be stored in the capacitance of analyte sensor 808 may be at least substantially discharged by the path that may be created by switch element 814 and optionally resistive element 832 in conjunction with the continued/ongoing toggling of switch element 816 that can be used to coupled terminal 828 to reference voltage 818 (e.g., ground) through this path. The charge that may be stored in capacitive element 834 can also be at least substantially discharged under these conditions (e.g., during this time period) because, where terminal 824 of measurement device 810 has been decoupled from the remaining elements of circuit 800, there is no new source of charging current for capacitive element 834.

Advantageously, circuit 800 when employed in conjunction with the circuit model shown in FIG. 7A or the like may result in a repeatable/consistent and/or controllable/configurable opportunity to generate voltage waveform(s) (e.g., waveforms 870 and 880, referencing FIG. 8B) that are sufficiently, reliably, and/or accurately detectable using detection circuit 802. If the initial current rush is not detected by analyte system 308 using circuit 800, due to any number of circumstances that may be present (e.g., analyte sensor 808 is not sufficiently hydrated, etc.), circuit 800 may enable additional attempts/chances for detection circuit 802 to detect analyte sensor 808 during subsequent active cycles following the reset cycle(s) that may be affected in the above-described manner.

Figure 8C:
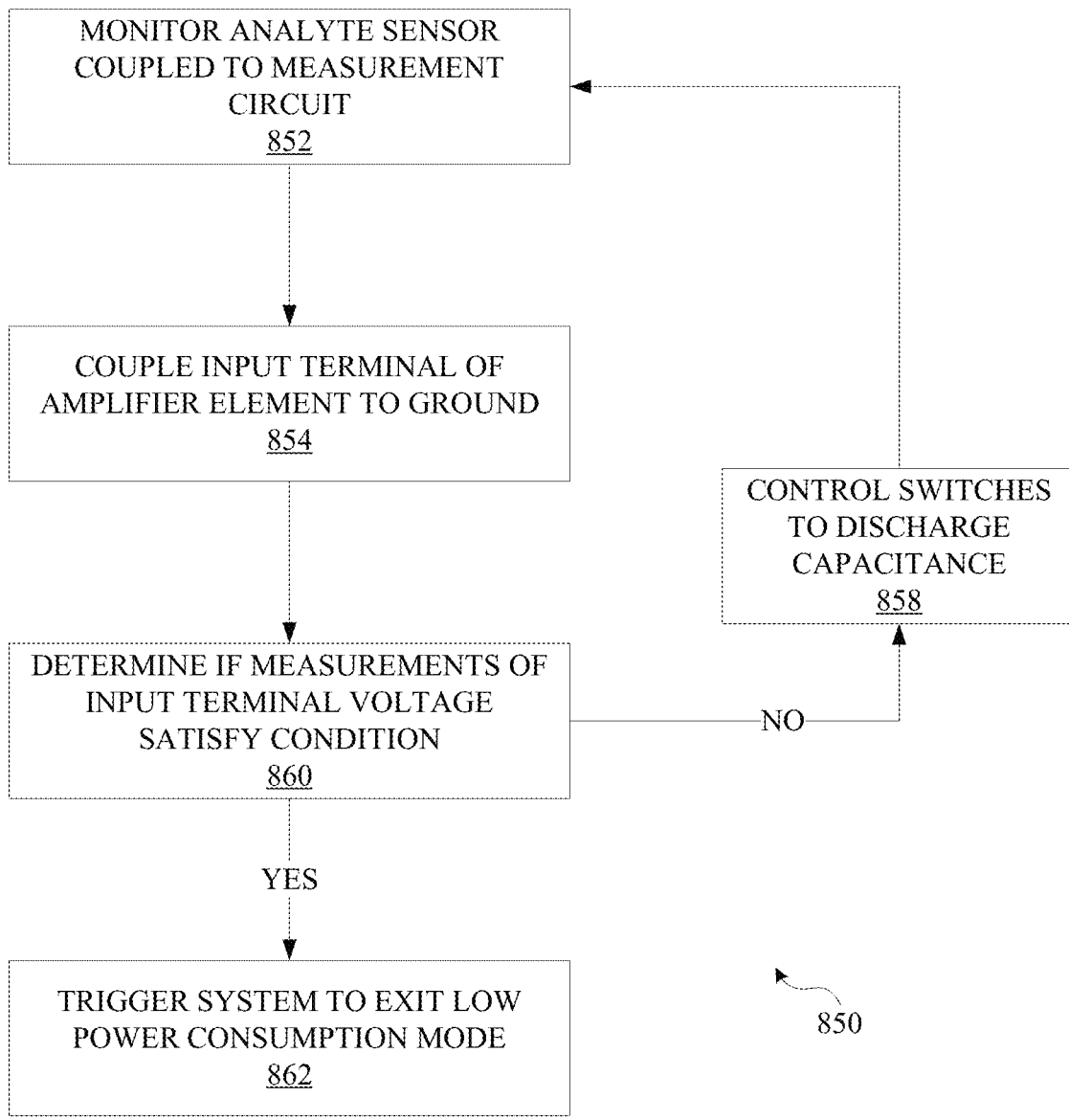
FIG. 8C is an operational flow diagram illustrating various operations that may be performed, in accordance with some embodiments.

FIG. 8C is an operational flow diagram illustrating method 850 for controlling activation of analyte sensor system 308 in accordance with embodiments of the disclosure. Method 850 is described below with reference to certain circuit diagram elements illustrated and discussed in connection with FIG. 8A, but method 850 should not be understood to necessarily be limited to such configurations/elements. Operations of method 850 may be employed in connection with a robust activation scheme for analyte sensor system 308.

At operation 852, method 850 may involve detection circuit 802 monitoring analyte sensor 808, for example, monitoring a voltage present on input terminal 822 of detection unit 802, where input terminal 822 may be coupled to second terminal 830 of analyte sensor 808. Analyte sensor 808 may be coupled to measurement device 810 (e.g., a potentiostat or other measurement circuit) for monitoring electrical properties of analyte sensor 808. Method 850 may optionally include, at operation 854, using switch element 816 to couple input terminal 822 of detection circuit 802 to reference voltage 818 (e.g., ground). Switch element 816 may be controlled and/or driven using one or more signals from driver circuit 806 (e.g., a clock or other signal driver).

At operation 860, method 850 may involve determining if the measurements of input terminal 822 of detection circuit 802 satisfy one or more conditions. For example, such conditions may include whether input terminal 822 of detection circuit 802 meets, exceeds, or crosses a threshold voltage (e.g., threshold 848, with reference to FIG. 8B, by way of example) or meets another characteristic, such as satisfying threshold 848 a number of times, or multiple times across multiple different time periods (e.g., as described above in connection with FIG. 8B). In embodiments, the condition/characteristic may include a consistent frequency of positive determinations that input terminal 822 of detection circuit 802 presents a voltage that meets, exceeds, or crosses a threshold voltage or meets another condition over a duration of time, thus helping ensure that the condition is not reached based on an anomaly.

By way of illustration, operation 860 may entail a voltage at input terminal 822 of detection circuit being compared to a threshold value (e.g., reference voltage 804, referencing FIG. 8A by way of example). For example, the voltage at input terminal 822 of detection circuit 802 may be indicative of a current that may flow between first and second terminals 828 and 830 of analyte sensor 808. As discussed above, in certain examples, detection circuit 802 may be, use, and/or include an amplifying element, comparator, and/or the like that can be used to detect whether the measured voltage across terminals 828 and 830 of analyte sensor 808 may meet or satisfy a characteristic (e.g., exceeds a threshold value). In embodiments, the characteristic (e.g., threshold voltage) may be set using reference voltage 804 that may be applied to reference terminal 820 of detection circuit 802.

If the one or more conditions are satisfied, method 850 may further include, at operation 862, analyte sensor system 308 being triggered to exit a lower power state. For example, analyte sensor system 308 may be triggered to exit the lower power state as a result of the one or more conditions being satisfied, as determined using circuit 800 and indicated by output 836 (referencing FIG. 8A by way of example). If the one or more conditions are not satisfied, however, method 850 may include operation 858, which entails controlling switch elements 812 and 814 (e.g., as described above in connection with FIGS. 8A and 8B) to at least substantially discharge a capacitance associated with analyte sensor 808. Method 850 may then entail returning to operation 852, while analyte sensor system 308 remains in the lower power state.

Thus, operation 858 may involve causing switch elements 812 and 814 to periodically at least substantially discharge a capacitance of analyte sensor 808, where, at a first time, switch 812 can be effectively closed or put into a low impedance state and thus be used to couple first terminal 828 of analyte sensor 808 to measurement device 810. And at a second time, switch element 812 may effectively be opened or put into a high impedance state in order to largely decouple first terminal 828 of analyte sensor 808 from measurement device 810, while switch element 814 can couple first terminal 828 and second terminal 830 of analyte sensor 808 together (e.g., in some cases through resistive element 834 that may be used as a current limiter) to at least substantially discharge analyte sensor 808 and/or circuit 800 capacitance. As discussed above, operation 858 can effectively reset circuit 800 to a measurement state so that a current that may flow through a capacitance of analyte sensor 808 can be largely repeated, thus enabling another detectable event and providing a more robust activation detection mechanism for analyte sensor system 308.

With further reference to FIG. 5, another technique that may be used for purposes of activating analyte sensor system 308 is voltage generation. In embodiments, a transcutaneous portion of analyte sensor 530 may be used to electrochemically generate a small voltage. That is, the body of the host into which analyte sensor 530 is inserted may be used as the electrolytic medium to enable a chemical reaction that produces electrical energy, as in a battery. For example, electrolytes within the body can be used to transfer electrons in a chemical reaction and develop a detectable voltage that can be monitored and used to trigger analyte sensor system 308 to exit the lower power state.

Using Other Signals to Exit the Lower Power State

According to embodiments, additional aspects of the present disclosure involve using secondary sensors or means other than analyte sensor 530 (with reference to FIG. 5, by way of example) for activation purposes in a pre-connected analyte sensor system 308. Various events may be detectable by analyte sensor system 308, where such events are indicative of implantation of analyte sensor 530. Examples include analyte sensor system 308 separating from an applicator, analyte sensor system 308 separating from packaging, and detecting the proximity of analyte sensor system 308 to the host or user. These events or phase changes may be detected using a multitude of various sensor types, as described below.

A first category of sensor types that may be used for detecting implantation related events involves activation detection circuit 520 using one or more signals generated by components that are included in analyte sensor system 308 without using additional components. This category of sensor types may be advantageous because such sensors can be self-contained within analyte sensor system 308, and hence may be lower in cost and complexity, and they typically do not require user interaction.

One example of a technique in the first category of sensor types uses a proximity sensor for purposes of activating analyte sensor system 308. Such a sensor can detect or approximate a distance and/or change in distance between analyte sensor system 308 and a reference point, where the reference point may be the host, an applicator for analyte sensor system 308, packaging for analyte sensor system 308, or another object. Referencing FIG. 5, a proximity sensor may be implemented using one or more of activation detection circuit 520 and activation detection component 545.

In embodiments, a proximity sensor may be implemented using capacitive sensing. For example, activation detection circuit 520 may include capacitive coupling circuitry that can detect and/or measure conductive objects or other objects that have a dielectric constant different than air. In this connection, two capacitive sensing types may be employed.

The first type of capacitive sensing may involve detecting a mutual capacitance between capacitive coupling circuitry and another object. The other object, such as, for example, the finger of the host or user, the skin of the host or user, the baseplate of an applicator, or any other object, may alter the mutual coupling between electrodes that may be included in activation detection component 545. Activation detection component 545 may communicate this alteration or change in the mutual coupling to activation detection circuit 520, to trigger an activation event, which may cause analyte sensor system 308 to exit a lower power state. It should be noted that in embodiments, monitoring of the capacitive coupling is done while analyte sensor system 308 is in the lower power state.

The second type of capacitive sensing may involve self-capacitance or absolute capacitance. Here for example, an object such as the user's finger or skin, or the baseplate of an applicator (see, e.g., FIGS. 6A and 6B described in detail below), can increase the parasitic capacitance of the capacitance sensor to ground, thus increasing the capacitive loading on a capacitance sensor of activation detection component 545. This capacitive loading event can be communicated to activation detection circuit 520, to trigger an activation event.

In embodiments, the proximity sensor may be implemented using inductive sensing. Inductive sensing can be employed to implement a non-contact electronic proximity sensor. The sensor may be used for positioning and detection of metal and other conductive objects that may be located in one or more portions of activation detection component 545 within the applicator for analyte sensor system 308. Here, reference is made to FIGS. 6A and 6B by way of example. The inductive sensing-based proximity sensor of activation detection component 545 may include an induction loop. Electric current usually generates a magnetic field. When the magnetic field changes, the changing field may generate a current. The inductance of the loop may change according to the proximity of a metal object altering the current flowing through the loop. The change in inductance can be detected using sensing circuitry that may be included in activation detection circuit 520 and/or activation detection component 545, the change can be used to trigger analyte sensor system 308 to exit the lower power state.

Another approach for implementing a proximity sensor is to employ a magnetic detector and/or sensor. Accordingly, embodiments of activation detection component 545 include a magnet that may be placed within packaging of analyte sensor system 308, within an applicator of analyte sensor system 308 (see, for example, FIGS. 6A and 6B), or on or within a display device utilized to interact with and/or display analyte values for a user. The proximity sensor can be configured to trigger an activation of analyte sensor 308 based on the presence or absence of a detected magnetic field (for example, a Hall effect sensor, Reed switch, or the like). The presence or absence of the detected magnetic field can then be used to trigger analyte sensor system 308 to exit the lower power state. More specifically, in some embodiments, a magnetic-based sensor may use a Hall effect, Reed switch, or other magnetic means for activation purposes. For example, a component within the applicator of analyte sensor system 308 (e.g., a needle hub, spring, needle, or the body of the applicator) or on a display device configured to allow a user to interact with and/or view information related to analyte sensor system 308 may be magnetized or may contain a magnet. The motion caused by deployment of analyte sensor system 308, removal of the same from the applicator, or motion of such a display device with respect to analyte sensor system 308 may trigger the magnetic-based sensor.

For instance, a conductive, flexible puck may be designed to make contact with a corresponding split connector within analyte sensor system 308 when analyte sensor system 308 is deployed. Once the flexible puck contacts the split connector, a short-circuit may be formed, causing analyte sensor system 308 to activate after detecting the short-circuit through an impedance measurement or through a resulting connection to power (e.g., battery). For example, a pull-up/pulldown circuit may be triggered using the puck. In another example, processor 535 can monitor for an interrupt signal from a Reed or Hall-effect switch or the like, which interrupt signal may be generated when the switch is no longer in sufficient proximity to a magnet that may be placed within the applicator of analyte sensor system 308 or within packaging for the same.

Figure 6A:
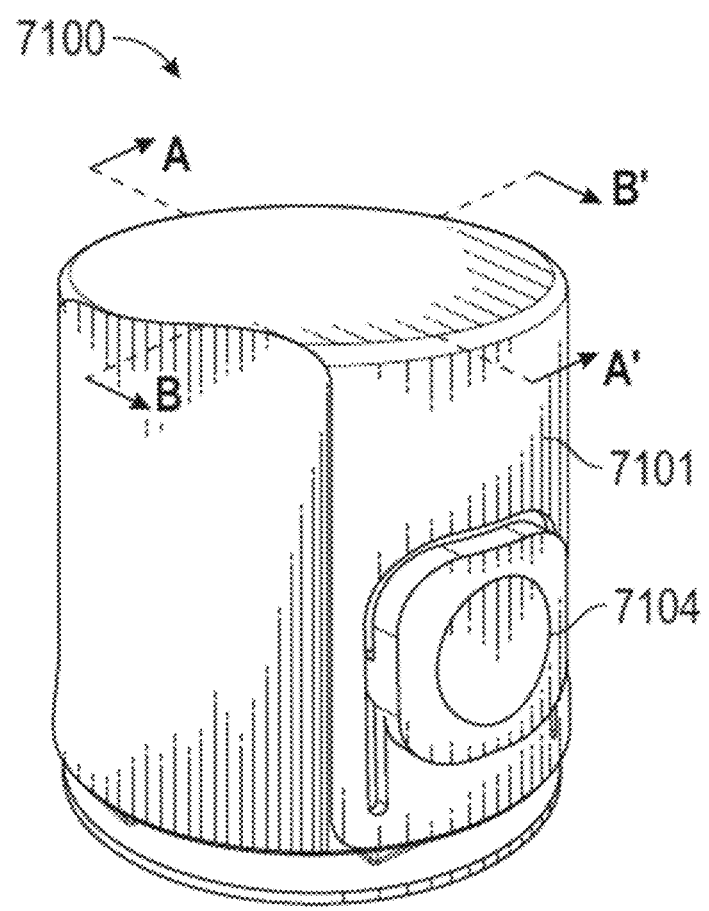
FIG. 6A illustrates aspects of an example application apparatus, in accordance with some embodiments.
Figure 6B:
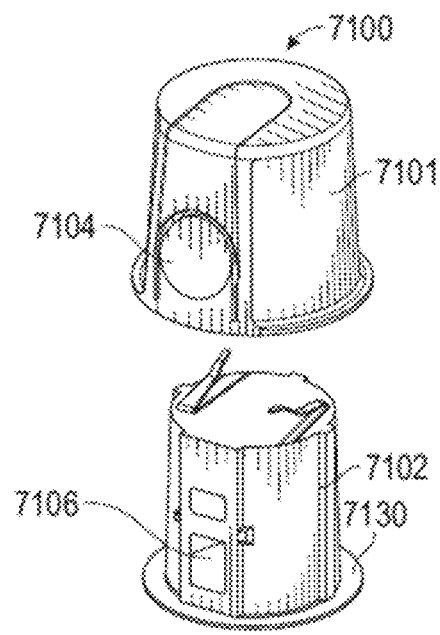
FIG. 6B illustrates another view of an example application apparatus, in accordance with some embodiments.
Figure 6B:
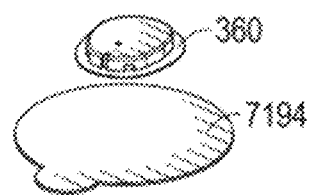
Figure 6C:
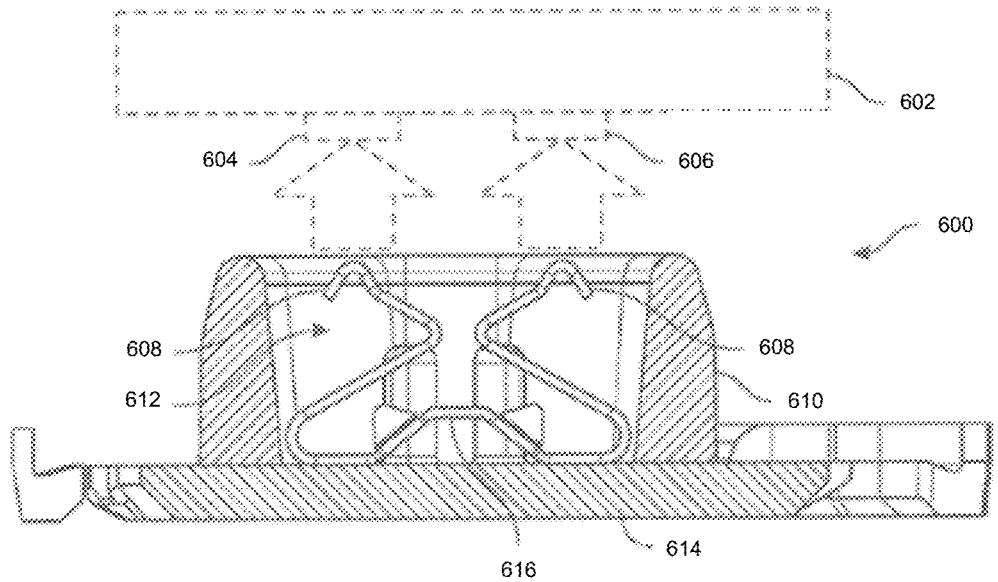
FIG. 6C illustrates aspects of an example activation detection component, in accordance with some embodiments.
Figure 6D:
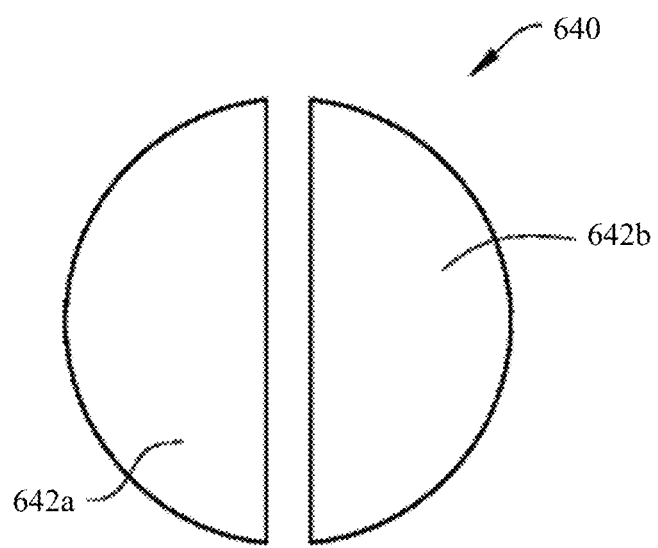
FIG. 6D illustrates aspects of a top view of an example connector, in accordance with some embodiments.
Figure 6E:
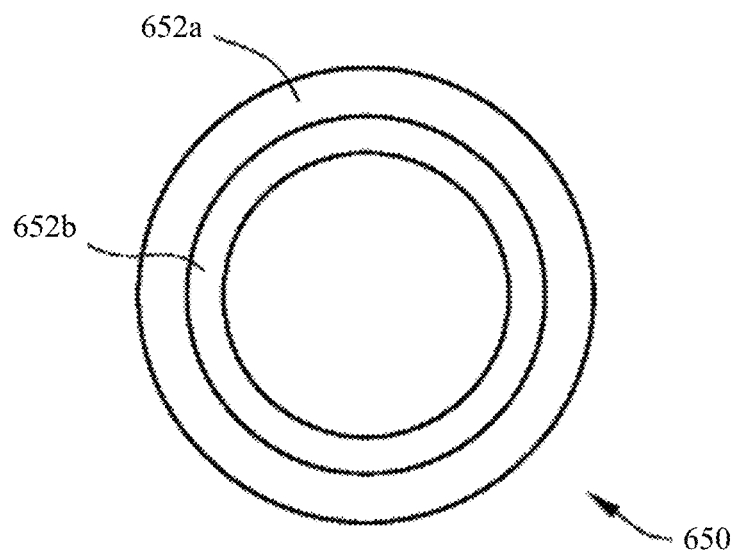
FIG. 6E illustrates aspects of a top view of another example connector, in accordance with some embodiments.

FIGS. 6D and 6E illustrate top views of respective example embodiments of split connectors 640, 650 of analyte sensor electronics module 12 that may be included in activation detection component 545. FIG. 6D illustrates an embodiment of an example split connector 640 having a generally axial symmetric layout, where connector 640 is split into two semicircular partial contacts 642a and 642b. FIG. 6E illustrates a top view of an embodiment of an example split connector 650 having a generally concentric (co-axial) design, where a first partial contact 652a is encircled by a second partial contact 652b. A space may be provided between contacts 652a and 652b to insulate contacts 652a and 652b from one another.

In some embodiments, while in a lower power mode, analyte sensor system 308 may monitor for an interrupt signal from a Reed switch. In embodiments, an interrupt signal is sent from a Reed switch when the switch is put in a second state (e.g., open state), which may occur when a magnet is no longer in sufficient proximity to the Reed switch to keep the Reed switch in the first state. For example, a magnet can be placed near to activation detection component 545 during manufacturing to keep analyte sensor system 308 in the lower power mode while analyte sensor system 308 is in packaging or a container thereof and/or in an applicator therefor. When it is desired to use analyte sensor system 308 and implant analyte sensor 530 into the user/host, analyte sensor system 308 can be removed from the container and/or packaging and the magnet may correspondingly be moved from being in proximity of activation detection component 545, thus causing analyte sensor system 308 to trigger activation. For example, a Reed switch, hall-effect switch, or the like can reside in analyte sensor system 308 to cause activation detection component 545 to trigger analyte sensor system 308 to exit the lower power state. Activation may occur, for example, when analyte sensor system 308 is removed from its product packaging. The switch can also be activated when analyte sensor system 308 is moved from being in proximity to the applicator.

In some embodiments, an interrupt signal is generated by and sent from a magnetic sensor, e.g., a Reed switch, when a magnet is brought into sufficient proximity to cause the magnetic sensor to change states. For example, a magnet (e.g., a thin, 10-30 mil self-adhesive magnet or magnetic sticker) can be affixed to, e.g., any of display devices 110, 120, 130, and 140 shown in FIG. 1. In some implementations, when a user wishes to wake analyte sensor system 308, for example to obtain one or more analyte concentration values (e.g., glucose concentration values) on demand, a user can touch analyte sensor system 308 with the magnet, affixed to the display device, or bring the magnet sufficiently close to analyte sensor system 308 for the magnetic sensor to change states. In some embodiments, the magnetic sensor can be configured to differentiate between different relative motions, spatial orientations and/or alignments of the magnet and/or its magnetic field with respect to the magnetic sensor. For example, the magnet can comprise a multi-pole magnet and/or the magnetic sensor may be configured to initiate or otherwise trigger a wakeup signal in response to a specific, predetermined relative motion and/or spatial orientation of the magnet or its magnetic field and the magnetic sensor and/or display device 110, 120, 130, 140.

Responsive to the state change of the magnetic sensor, a wakeup signal configured to cause analyte sensor system 308 to wake from a lower power consumption mode can be triggered. Upon waking from the lower power consumption mode, analyte sensor system 308 can be configured to initiate a wireless communication protocol (e.g., BLE) and/or power up an associated chip. Transceiver 510 can be configured to begin advertising for example by transmitting one or more advertising packets. In some embodiments, the advertising packets can comprise one or more codes and/or patterns unique to the particular wakeup protocol. The display device 110, 120, 130, 140 can receive the advertising packets and transmit a request for an analyte concentration value to transceiver 510. Analyte sensor system 308 can be configured to transmit one or more analyte concentration values to display device 110, 120, 130, 140. Upon transmitting the one or more analyte concentration values, analyte sensor system 308 can be configured to discontinue transmitting advertising messages and revert to the lower power consumption mode. In response to receiving the one or more analyte concentration values, display device 110, 120, 130, 140 can be configured to play a short audio clip or sound indicating to the user that the analyte concentration value(s) has/have been received by display device 110, 120, 130, 140. Such embodiments may be advantageous for a number of reasons, including but not limited to very low cost of implementation, low impact on battery life, compatibility with any type of display device, even those without certain communication protocols, and provision of a solution that minimally affects aesthetics of display device 110, 120, 130, 140.

In embodiments, sonic and/or audio detection can be used to sense proximity between analyte sensor system 308 and a reference point. For example, activation detection circuit 520 and/or activation detection component 545 can include an ultrasonic or audio-based proximity sensor and one or more microphones and/or speakers that can use, for example, a Doppler effect to detect relative movement between an object, such as the applicator or packing, and analyte sensor system 308. The detected movement can then be used to trigger analyte sensor system 308 to exit the lower power state. By way of example, a shift in frequency of an ultrasonic or audio signal may be detected using sonic/audio detection that analyte sensor system 308 is moving away from the applicator or packaging in a fashion that indicates implantation is occurring or is about to occur. In some embodiments, frequency shift may not be required for detection/activation purposes. Rather, the presence or absence of audio/sonic signaling may be used to trigger activation of analyte sensor system 308, or the presence of audio/sonic signaling of a certain amplitude or character can be used for activation purposes.

Temperature-based detection approaches may be utilized in addition to or in alternative to proximity-based techniques as another example of an electromechanical technique in the first category of sensor types (e.g., that do not use components external to analyte sensor system 308). Here, one or more temperature sensors can be coupled to a printed circuit board, chip, etc. For example, activation detection component 545 may include such temperature sensors that may employ a thermistor, thermocouple, or the like. The temperature sensor of activation detection component 545 may be implemented within analyte sensor system 308 and/or external thereto.

Temperature sensors can be configured to detect a temperature at a single location (for example, a change in temperature or comparison of the temperature to a threshold) or multiple locations to detect a temperature gradient (for example, multiple temperature sensors can be utilized at different locations with a known distance of separation). In some cases, temperature can be used to infer contact and/or proximity with the user's body. For example, the temperature being closer to the typical temperature of the human body may be indicative of proximity to the user. The gradient measurement may be used to infer heating or cooling from a known direction, and hence, for example, may be used to infer direction of movement of analyte sensor system 308 or another object emitting heat (e.g., body of the host, etc.) or of orientation that is closer to or further from the human body. Accordingly, a detected temperature or temperature profile can be used to trigger analyte sensor system 308 to exit the lower power state.

In embodiments, activation detection circuit 520 and/or activation detection component 545 may include one or more accelerometers or gyroscopes that may be used to monitor motion and orientation of analyte sensor system 308 and detect one or more events indicative of implantation of analyte sensor 530. One such event may involve a relatively sudden increase in acceleration of analyte sensor system 308 that may result, for example, from a spring activated applicator mechanism that may be used in connection with implantation of analyte sensor 530 (here, reference is made for example to FIGS. 6A and 6B). Another such event may involve deceleration from analyte sensor system 308 impacting a user's skin surface (e.g., hitting the user during implantation). In embodiments, both acceleration and deceleration events can be used for increasing robustness, detecting motion-related events, and/or triggering activation of analyte sensor system 308.

One potential concern in accelerometer and other deployment-based activation methods is power usage. For example, power usage involved in monitoring an accelerometer signal may be proportional to the sampling frequency used for the monitoring. Because analyte sensor 10 insertion/implantation typically occurs over a relatively short time period (e.g., 30 milliseconds), a relatively high sampling frequency (e.g., 5 milliseconds) may be necessary in order to reliably detect implantation. Such a relatively high sampling frequency may correspond to higher power consumption. Accordingly, embodiments of the present disclosure are directed to accurately capturing acceleration/deceleration and other motion-related events using an accelerometer while maintaining power efficiency.

In example embodiments, the sampling frequency used to monitor signals from an accelerometer or other means for detecting deployment of analyte sensor system 308 can be varied. For example, a lower sampling frequency can be used for monitoring the accelerometer signal in a power efficient manner in response to an event indicative of an upcoming deployment of analyte sensor system 308. Such an event may include, for example, a user un-boxing of analyte sensor system 308, the user opening packaging associated with analyte sensor system 308, and/or the user's presence in a location/time that is typically associated with installation/deployment/implantation of analyte sensor system 308 (e.g., in a hospital, clinic, user's home or other such location, as may be determined using location services such as GPS etc., and/or at a certain time of day and/or date when the user prefers to or typically deploys analyte sensor system 308).

An additional event that may be used to indicate an upcoming deployment of analyte sensor system 308 may be or include: (1) removal of the applicator safety mechanism, such as the applicator's safety card (e.g., a plastic component removed from the applicator to enable triggering) or frangible portion (e.g., a breakable portion on the trigger of the applicator that must be removed to enable triggering); (2) push/force applied to the applicator (e.g., an applicator must be placed on a surface (e.g., skin surface) with a minimum force to enable triggering); (3) the breaking of a frangible member (e.g., similar to a safety ring of a plastic soda bottle); (4) the partial rotation of a threaded safety ring; (5) applying pressure to an integrated side trigger button; and/or (6) various other safety lock mechanisms. Another approach to changing a sampling frequency that may be used for accelerometer monitoring may involve haptic input obtained directly or indirectly from a user that may be detected using an accelerometer (e.g., a user may tap analyte sensor system 308 to transition to a higher sampling frequency). This is discussed in further detail below.

Although the safety lock mechanism may be configured to be energized/triggered by a user, in some embodiments, a pre-energized system can also employ a safety lock mechanism, for example to prevent premature triggering or activation of an already energized spring.

These triggering events for the accelerometer or other activation detection means may cause a transition in the sampling frequency used by analyte sensor system 308 to monitor the output signal of the accelerometer or other activation means from a relatively lower sampling frequency to one or more relatively higher sampling frequencies, where the one or more higher sampling frequencies are able to more reliably detect/capture a motion trigger or other event that occurs over a relatively short time period, such as implantation of analyte sensor 530. By varying the sampling frequency, a lower amount of power may be used while still maintaining accurate event detection using an accelerometer-based or other technique such as described herein.

While the use of positive/affirmative motion-related events is described above, it should be appreciated that negative motion-related events may also be used for triggering an activation of analyte sensor system 308 and/or for changing a sampling frequency or frequencies that may be used to monitor an accelerometer. That is, the lack of motion, orientation, or a specific location or type of location, may be used to trigger a lower sampling frequency or frequencies. By way of example, if analyte sensor system 308 has been relatively immobile for a prolonged period or has been in the same position/orientation for relatively prolonged period, a lower sampling frequency may be employed. As an additional example, if analyte sensor system 308 is determined (e.g., based on GPS, A-GPS, location detection, user check-in, or using other location services) to be located in a storage facility, a lower sampling frequency may be employed. This may enable power savings without sacrificing the accuracy of implantation detection, where the conditions indicate that implantation is unlikely to occur.

Figure 9:
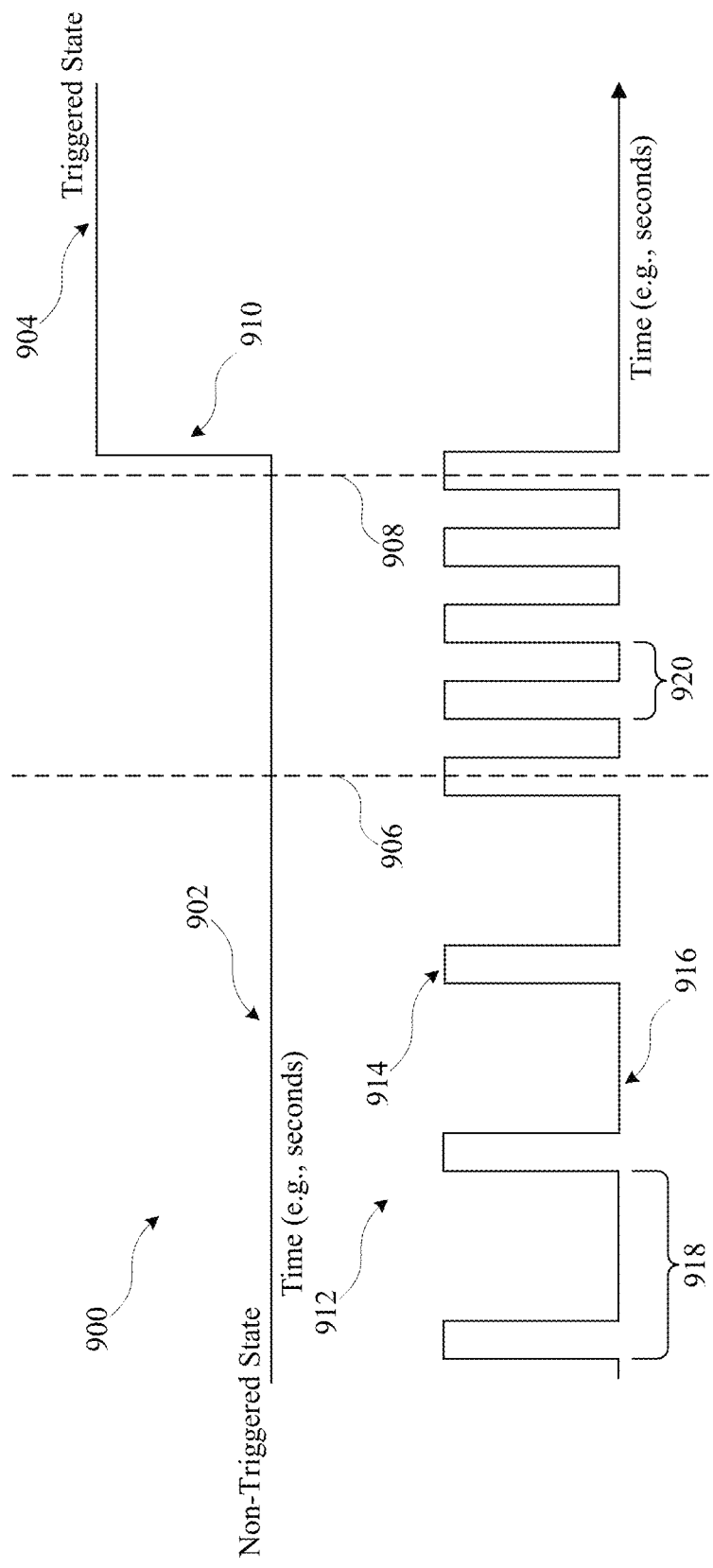
FIG. 9 illustrates example plots illustrating the operation of an example analyte sensor system, in accordance with some embodiments.

FIG. 9 provides example plots illustrating the operation of analyte sensor system 308 in connection with an accelerometer-based or other detection scheme that employs a variable sampling frequency in order to reduce power consumption and/or accurately detect implantation of analyte sensor 530, while also maintaining the ability to reliably activate analyte sensor system 308 and avoid false wakeups (e.g., to more reliable calculation of analyte values, etc.). For example, the accelerometer signal may be used in a power efficient sampling frequency (e.g., 1 s, 2 s, 5 s, 30 s, 1 min, greater than 1 min, depending upon the application) to detect an event, such as but not limited to: motion associated with unboxing or opening packaging, locating an installation area, applicator safety removal, and/or applicator triggering. Once detected, such an event can be used to cause the accelerometer to be sampled more frequently (e.g., less than 1000 ms, 500 ms, 250 ms, 100 ms, 50 ms, 10 ms, etc.), where the higher frequency can enable more reliably capturing a motion trigger event. Alternatively, or additionally, events may be detected that involve a relative lack of motion or an orientation, and such events may be used to trigger a lower sampling frequency in certain instances.

Plot 900 represents one or more operational states of analyte sensor system 308, as plotted against time (e.g., seconds). For example, the one or more operational states may include a non-triggered state and a triggered state of analyte sensor system 308. The non-triggered state may in various cases include or be an inactive or substantially inactive state, a lower-power state, a sleep mode, and/or the like. At point 902 of plot 900, a measurement device (e.g., a potentiostat) that may be used in connection with analyte sensor system 308 detecting an analyte in a host may be responsive to certain input events. For example, when analyte sensor system 308 is in the non-triggered state, one or more electrodes of analyte sensor 530 may be voltage biased and/or used to measure the analyte or gather information related thereto. It should also be appreciated that in certain embodiments, during the non-triggered state, the one or more electrodes of analyte sensor 530 may not be biased. For example, biasing of the electrodes may in some cases be largely reduced or avoided during the non-triggered state. This may be based on monitored environmental or other conditions as described herein, predetermined variables or settings, etc.

At point 904, analyte sensor system 308 is shown in the triggered state. The triggered state may in various cases be thought of as analyte sensor system 308 being in an active or substantially active state. In example implementations of the triggered state of analyte sensor system 308, analyte sensor 530 may be voltage biased using the measurement device or may otherwise be caused to measure/characterize the analyte. Furthermore, in the triggered state of analyte sensor system 308, other components of analyte sensor system 308 may be operated, for example, connectivity interface 505 may receive/transmit data, processor 535 may execute various operations, etc. Region 910 of plot 900 represents an example of a transition between the non-triggered state and the triggered state of analyte sensor system 308.

As further illustrated in FIG. 9, plot 912 may represent an example of a signal that may be used in connection with changing an operational status/state of analyte sensor system 308 vs. time (e.g., seconds). The signal can be monitored (e.g., over time) and used to change or otherwise control the operational status/state of analyte sensor system 308, one or more components thereof, and/or circuitry within activation detection circuit 520 of analyte sensor system 308. For example, such components and/or circuitry can be used to monitor an output signal from an accelerometer or other activation detection means that may be used in connection with activation detection component 545.

At time region 916, for example, the signal may be at or relatively near a first value (e.g., a relatively lower value is shown in FIG. 9, though it should be appreciated that the first value could be a relatively higher value). Additionally, or alternatively, the signal could be, include, and/or be used to convey an otherwise different value, a trend, a frequency, a slope, a gradient, and/or the like, etc. that may be observed/detected. For example, the first value etc. could be compared/measured on an absolute or self-relative basis and/or vis-à-vis other values/characteristics for the signal that may occur at different time regions, such as those shown in plot 912. The first value etc. of the signal can be used to indicate that analyte sensor system 308, components thereof, and/or monitoring circuitry may be maintained in the non-triggered state.

And, for example, at time region 914, the signal may be at or relatively near a second value (e.g., a relatively higher value is shown in FIG. 9, though it should be appreciated that the second value could be a relatively lower value). Additionally, or alternatively, the signal could be, include, and/or be used to convey an otherwise different value, a trend, a frequency, a slope, a gradient, and/or the like, etc. that may be observed/detected. For example, the second value etc. could be compared/measured on an absolute or self-relative basis and/or vis-à-vis other values/characteristics for the signal that may occur at different time regions, such as those sown in plot 912 in FIG. 9. The second value etc. can alone or, for example, in combination with the first value and/or other variables/conditions, be used to indicate that analyte sensor system 308, one or more components thereof, and/or monitoring circuitry may, for example, maintain analyte sensor system 308, components thereof, and/or the monitoring circuitry in the non-triggered state, but may more actively monitor an output signal from the accelerometer and/or other activation detection means that may be used in connection with activation detection component 545.

FIG. 9 also shows that plot 912 may include sampling period 918 that may be employed before the occurrence of trigger 906. In response to trigger 906, sampling period 920, which may be shorter than sampling period 918 (e.g., thus representing a higher sampling frequency), may be employed. By way of example, trigger 906 may be an acceleration/deceleration event associated with un-boxing analyte sensor system 308, or any other triggering event described herein. Using shorter sampling period 920, the monitoring circuit may be enabled to detect a motion-based and/or other event associated with upcoming, currently occurring, or past implantation of analyte sensor 530, which is represented here by way of example by trigger 908. In response to trigger 908, analyte sensor system 308, components thereof, the measurement device, and/or monitoring circuitry transitioned from the non-triggered state 902 through transition region 910 into the triggered state 904. Trigger 908 may initiate a transition of analyte sensor system 308 from a lower power state to a more active state, for example.

In embodiments, a wireless/antenna-based technique may be used for purposes of activating analyte sensor system 308. For example, activation detection component 545, portions of which may be internal to analyte sensor system 308 and/or portions of which may be external to analyte sensor system 308, may include a component such as an NFC or RFID tag that may be placed in proximity to analyte sensor system 308. By way of example, such a tag may be located within an applicator for analyte sensor system 308 or within packaging for analyte sensor system 308 (see FIGS. 6A and 6B, for example). Analyte sensor system 308 may, at a regular interval, interrogate the tag to establish a proximity relationship. For example, analyte sensor system 308 may use a transmitter that may be part of the transceiver 510 to send/receive a ping or other message/signal to/from the tag. If analyte sensor system 308 does not receive a response to the ping or other message/signal, the lack of response may be used to indicate deployment of analyte sensor system 308 (e.g., insertion of analyte sensor 530) and therefor trigger exiting a lower power mode. In embodiments where analyte sensor system 308 continues to send ping messages after deployment, analyte sensor system 308 can receive input indicating that deployment has occurred (e.g., via a GUI of a connected display device 310), and as a result cease sending the ping messages. In some cases, the tag may be an active component that pings analyte sensor system 308 or the activation detection component. In such cases, if analyte sensor system 308 stops receiving pings from the tag, the lack of ping messages being received may be used to indicate deployment of analyte sensor system 308.

In example embodiments, during deployment of analyte sensor system 308 or removal of the same from packaging, NFC or RFID may be used to detect an alteration in the proximity relationship between analyte sensor system 308 and a reference point such as the packaging, and the alteration may be used to trigger analyte sensor system 308 to exit a lower power state. Alterations of the proximity relationship may also be detected using measurements that may be made, for example, by transceiver 510, such as RSSI or other channel measurements that may indicate proximity from a reference point. These measurements (e.g., RSSI) may be used to trigger analyte sensor system 308 to exit the lower power state when the estimated distance between the reference location and analyte sensor system 308 satisfies a condition such as specific threshold distance for example. Additionally, in certain embodiments, NFC can be used to provide a wakeup command (e.g., from one or more display devices) to analyte sensor system 308 to activate the analyte sensor system 308. Alternatively, the lack of an NFC ping, or the NFC ping dropping below a certain power level, can be used to indicate a lack of proximity and hence trigger activation of analyte sensor system 308.

In other examples, analyte sensor system 308 may utilize a radio frequency echo to trigger analyte sensor system 308 to exit a lower power state. For example, analyte sensor system 308 may use transceiver 510 to intermittently emit an RF signal and monitor the echo of the same for parameters that may be known (e.g., well characterized) for a given environment (e.g., within packaging or an applicator). Such parameters may include signal strength, Doppler, distance, density, and material, by way of example. If subsequent emissions and resulting echoes change, this may indicate a change in environment that may be used to trigger activation. Accordingly, embodiments involve detecting environmental changes using radio waves to determine range, angle, or velocity of objects surrounding analyte sensor system 308 using bounce-back of transmitted signals to characterize (e.g., changes) in the surrounding environment. For example, phase angle and the like can be measured to characterize the surrounding environment. One example of an RF emission may involve BLE (Bluetooth Low Energy). In one example, one or more wireless sources may broadcast wireless signals from one or more specific locations. The wireless source(s) may be localized to one or more facilities or other locations where analyte sensor system(s) 308 may be stored, or to a manufacturing location associated with analyte sensor system(s) 308. In some examples, the wireless source(s) may be BLE sources or RF sources as described herein. In embodiments, the analyte sensor system 308 (e.g., while located in the storage facility) may be configured to monitor or listen to the broadcasted wireless signals or signal characteristics and determine whether the received broadcasted signal characteristic (e.g., signal strength or other aspects) is above, below, or near a threshold. Based on the determination, analyte sensor system 308 may or may not transition from a lower-power/sleep mode to an active mode. For example, if the received signal characteristic is above a threshold (e.g., which may indicate that analyte sensor system 308 is still within the storage facility), analyte sensor system 308 may remain in the lower-power or sleep/shelf mode. In another example, when analyte sensor system 308 is moved to another location (e.g., a patient's home or a doctor's office or further away from the storage facility) analyte sensor system 308 may determine that the monitored signal characteristic is below the threshold. As such, analyte sensor system 308 may then transition to an active or operational mode from the lower-power mode.

Activation detection component 545, in embodiments, includes an air pressure sensor that may be used in connection with activating analyte sensor system 308. For example, activation detection component 545 may include an air pressure sensor that may be configured to detect changes in air pressure. The air pressure sensor may be, along with analyte sensor system 308, stored in packaging pressurized above (e.g., greater than 1 atm) or below normal (e.g., vacuum) typical barometric pressure conditions. The act of breaching (e.g., opening, piercing, etc.) the packaging associated with analyte sensor system 308 may then result in a change in pressure. A pressure transition event may then be used as a detectable event for triggering activation of analyte sensor system 308 when the packaging is breached and the pressure changes. Analyte sensor system 308 may be configured to have a flexible portion (e.g., diaphragm) that may allow pressure changes outside of a moisture protected volume (e.g., a sensor measurement electronics housing) within analyte sensor system 308 to be detected within the moisture protected volume. Where analyte sensor system 308 is delivered in a multipack configuration, each analyte sensor system 308 in the multipack may have individual pressurized chambers within the packaging, such that each analyte sensor system 308 may exit the lower power state individually based on pressure changes.

In embodiments, activation detection component 545 includes a microphone (e.g., passive or active device) that may be located within analyte sensor system 308 and used to detect an audio signal or signature indicative of deployment of analyte sensor system 308. For example, the audio signal/signature may be associated with the applicator deploying analyte sensor system 308 (e.g., applicator trigger, mechanism, impact with user). Such audio signal/ signatures may be specific to deployment events such that they may be used to trigger analyte sensor system 308 to exit a lower power state.

In some embodiments, activation or waking of analyte sensor system 308 may be triggered based, at least in part, on successful deployment of analyte sensor system 308 as determined based, at least in part, on detection of a sound or acoustic signature indicative of successful deployment by a display device configured to provide information regarding analyte sensor system 308 to a user. Such embodiments can provide early deployment failure detection and/or a successful deployment detection. For example, certain spring-based applicators can make sounds or have an acoustic signature during deployment operation from which timing of moving parts can be inferred without opening or inspection of the applicator. Accordingly, an application running on any of, e.g., display devices 110, 120, 130, 140 can be configured to, once open and running, differentiate unsuccessful analyte sensor system 308 deployment from successful deployment and, in some cases, further infer the specific cause of an unsuccessful deployment by analyzing a sound made by the applicator during deployment. Such embodiments would not only allow another, in some cases supplementary, method of verifying successful deployment for proper wakeup of analyte sensor system 308, but also allow for troubleshooting the cause of particular deployment failures in the field in near real-time, without a need for returning a defective applicator and/or analyte sensor system 308 to the manufacturer for investigation into the cause of failure. Such information can be valuable at least in that it can allow for review of issues mapped to particular applicator lots, it can allow further innovations in future applicator and analyte sensor system design and can reduce the costs associated with returning and investigating failed applicators.

In some embodiments, a microphone of display device 110, 120, 130, 140 can be configured to generate a recording of one or more audio waveforms and/or spectrograms of a sound made by the applicator and/or analyte sensor system 308 during deployment. The application running on display device 110, 120, 130, 140 can be configured to analyze the one or more recorded waveforms and/or spectrograms and differentiate successful deployments from unsuccessful deployments based on the analysis. For example, the application can be configured to record an audio waveform and/or spectrogram at a predetermined sampling rate (e.g., 96 kHz) such that a desired granularity in the time course of deployment can be obtained (e.g., capability to differentiate between aspects of sounds and/or audio signatures at 1 ms±0.025 ms). In some embodiments, the application can be configured to isolate, correlate and/or identify portions of the recorded waveforms and/or spectrograms indicative of specific parts of the applicator and/or analyte sensor system 308 performing known movements as a part of the deployment process and identify if and/or when such specific parts are performing such known movements within a timeframe, at a certain speed and/or at an appropriate time with respect to one or more other movements or sounds related to the deployment sufficient to infer a successful, or alternatively unsuccessful, deployment. Examples of such isolated sounds can include but are not limited to one or more clicks indicative of a part latching and/or releasing from another part, and/or one or more bangs or sound peaks indicative of a drive wheel or booster moving, rotating and/or stopping. In some embodiments, upon determination of an unsuccessful deployment, the application can provide one or more notifications to the user, e.g., "Remove sensor," indicating an unsuccessful deployment, or alternatively one or more notifications to the user indicating a successful deployment. In some embodiments, upon determination of a successful deployment, the application can provide one or more notifications to the user indicating the successful deployment.

Activation detection component 545 may include an optical-based sensor that can be used to cause analyte sensor system 308 to exit the lower power state. By way of illustration, such an optical-based sensor may be photovoltaic. A voltage may be generated based on exposure of the optical sensor to photons. The generated voltage may then be compared to a threshold in the result of the comparison may be used to trigger activation of analyte sensor system 308. The optical-base sensor may thus use exposure to light for activation purposes. The sensor may be external to analyte sensor system 308, or, for example, may be located within analyte sensor system 308 and covered by an optically transparent portion of the housing of analyte sensor system 308 such that light may still reach the optical-based sensor. In embodiments, the optical-based sensor may include a CMOS device, CCD device, a photodiode, photoresistor, and/or phototransistors that may be triggered by exposure to normal daylight conditions or when the light exposure satisfies a threshold condition. Such optical-based sensors may be considered to be part of activation detection component 545 that is separate from activation detection circuit 520 or may be encompassed within activation detection circuit 520. In one example, the user equipment (UE) devices (e.g., display device 310) may provide the light signal that may be used to activate analyte sensor system 308 (e.g., an LED light source from the UE device may be used). In another example, exposure to light may occur when a sticker or other element that covers the detector is automatically removed when analyte sensor system 308 is removed from the applicator or packing thereof.

Activation detection circuit 520 and/or activation detection component 545 may include a conductivity-based sensor that may be used to trigger analyte sensor system 308 to exit a lower power state. Such a sensor may utilize resistance measured through a user's skin when analyte sensor system 308 has been deployed. For example, a conductivity-based sensor may measure a large (e.g., open circuit) resistance before analyte sensor system 308 has been deployed and analyte sensor 10 has been implanted in the user. However, once analyte sensor system 308 is deployed and analyte sensor 10 implanted, the resistance measured by the conductivity-based sensor may decrease via a conductive path through the user's skin. The conductive path may be measured between two electrodes of activation detection circuit 520 and/or activation detection component 545. For example, a first conductive probe may contact the surface of the user's skin during deployment, and resistance may be measured from the first conductive probe to an electrode of analyte sensor 10, where the measured resistance is detectably lower during deployment than before deployment. Alternatively, or in addition, two or more conductive probes may contact the surface of the user's skin in different locations separated by a distance (e.g., several millimeters) and, relative to the resistance measured between the probes before deployment, a lower resistance may be measured between these (e.g., two) conductive probes after deployment of analyte sensor system 308. The change in the measured resistance before and after deployment may be used to trigger analyte sensor system 308 to exit the lower power state.

In some cases, one or more electromechanical or mechanical-based switches or sensors may be used for activation purposes. In embodiments, activation detection component 545 includes a switch-based sensor. For example, a mechanical switch may be located on analyte sensor system 308. The switch can be sealed (e.g., using a gasket) such that the external and internal portions of analyte sensor system 308 may be isolated from one another. The switch-based sensor may use a momentary or latching switch and may be used to connect circuits of analyte sensor system 308 to a power source (e.g., a battery of analyte sensor system 308) in order to trigger circuit wakeup (e.g., by forming a connection through a wakeup pin). The switch may be triggered by analyte sensor system 308 being unboxed/unpackaged, by the applicator during deployment, and/or by analyte sensor system 308 hitting/impacting the user during deployment. The switch may be mechanically triggered and may release when analyte sensor system 308 is deployed.

In embodiments, activation detection circuit 520 and/or activation detection component 545 may include two or more exposed contacts configured in an open circuit that may be used to cause analyte sensor system 308 to exit a lower power state. By way of example, electrical contacts external to analyte sensor system 308 may be part of an open circuit that is internal to analyte sensor system 308. Bridging (e.g., using an electrical jumper) two such electrical contacts, such that the electrical contacts form an electrical connection with one another (e.g., using another conductive material to form the bridge), may trigger activation of analyte sensor system 308. Alternatively, two such electrical contacts may already be electrically connected to one another, and the act of breaking this connection may trigger activation of analyte sensor system 308. For example, bridging or un-bridging/disconnecting the electrical contacts may pull a node up or down to trigger activation of analyte sensor system 308, and/or form a connection to a battery of analyte sensor system 308 as a means of triggering activation. Aspects of this are described further with reference to FIG. 6C.

The above-described bridge may be located in or may be part of the applicator of analyte sensor system 308, such that the bridge may be used to trigger activation when analyte sensor system 308 exits the applicator (e.g., the bridge may be broken or formed). The bridge may be located in a baseplate of analyte sensor system 308 and may be used to trigger activation during assembly of analyte sensor system 308 (e.g., the bridge may be broken or formed). For example, during assembly of pre-connected analyte sensor system 308, two mechanically separate/connectable pieces may be joined by the user or the applicator, and this joining may form or disrupt the bridge, triggering activation.

The bridge described above may be used to connect power (e.g., from a battery of analyte sensor system 308) or to trigger circuit wakeup (e.g., using a wakeup pin). The bridge can be used to facilitate automatic wakeup of pre-connected analyte sensor system 308 via needle retraction, where the needle serves as a bridge (e.g., jumper) between two sets of contacts on a circuit board using a multilayer gasket with an insulating layer in the middle separating two conductive layers. While the needle is bridging the gasket, the circuit may be bridged/closed. And once the needle is retracted (e.g., during deployment of analyte sensor system 308), the circuit may be broken/opened/unbridged, triggering activation. One benefit of using a gasket through the needle pathway is the reduction in the size of the opening through the assembly of analyte sensor system 308, which could help with potential concerns regarding ingress of debris and blood visibility to the user. This can help prevent debris and excess moisture from reaching the wound site and hide blood from the user.

FIG. 6A illustrates applicator 7100 for an on-skin sensor assembly of analyte sensor system 308, according to embodiments of the disclosure. Applicator 7100 may include activation element 7104 disposed on a side of applicator 7100, for example, on a side of outer housing 7101 of applicator 7100. In some embodiments, activation element 7104 may be a button, a switch, a toggle, a slide, a trigger, a knob, a rotating member, a portion of applicator 7100 that deforms and/or flexes, or any other suitable mechanism for activating an insertion of analyte sensor 530 and/or retraction assembly of applicator 7100. In some embodiments, activation element 7104 may be disposed in any location, e.g., a top, upper side, lower side, or any other location of applicator 7100. Applicator 7100 may be large enough for a host to grasp with a hand and push, or otherwise activate, activation element 7104 with, for example, a thumb, or with an index finger and/or a middle finger. Applicator 7100 may be sized appropriately to house analyte sensor system 308, as well as one or more components of activation detection component 545 described above.

Applicator 7100 may be configured with one or more safety features such that applicator 7100 can be prevented from activating until the safety feature is deactivated. In one example, the one or more safety features may prevent applicator 7100 from activating unless applicator 7100 is pressed against the skin of a host with sufficient force. Moreover, applicator 7100 may be further configured such that one or more components therein retract based at least in part on the one or more components pushing against the skin of the host with a force exceeding a predetermined threshold, rather than based on the one or more components translating beyond a predetermined and static distal position. In other words, applicator 7100 may implement force-based retraction triggering rather than being limited to displacement-based retraction triggering.

FIG. 6B illustrates an exploded perspective view of applicator 7100 of FIG. 6A, according to some embodiments. As shown, applicator 7100 may include outer applicator housing 7101 that may include activation element 7104. Outer applicator housing 7101 may be configured to translate in a distal direction by a force applied by a host to applicator 7100, specifically to inner housing 7102, thereby aligning activation element 7104 in a position that allows applicator 7100 to fire.

Applicator 7100 can further include inner housing 7102, configured to house at least one or more mechanisms utilized to apply analyte sensor assembly 360 (for example, as referenced above in connection with FIG. 3A) to the skin of a host. As mentioned above, analyte sensor assembly 360 may include or house analyte sensor system 308. A distal surface 7130 of a bottom opening of inner housing 7102 may define a bottom surface of applicator 7100. In some embodiments, upon applicator 7100 being pressed against the skin of a host, the skin may deform in a substantially convex shape at distal surface 7130 such that at least a portion of a surface of the skin is disposed at the bottom opening of applicator housing 7102 extends into the bottom opening of inner housing 7102 beyond a plane defined by distal surface 7130 in a proximal direction. One or more components of activation detection component 545 described above may be included in or on inner housing 7102, such as, for example, NFC components, magnets, etc., or any other of the components describe above that may be external to analyte sensor system 308. In some embodiments, barrier layer 7194 may be disposed over the bottom opening of inner housing 7102.

Activation of applicator 7100 may include a host pressing applicator 7100 against the skin with sufficient force to translate outer housing 7101 in a distal direction toward and with respect to inner housing 7102 until activation element 7104 is aligned with aperture 7106 of inner housing 7102. Once such an alignment is achieved, a host may initiate (e.g., pushing) activation element 7104. In some other embodiments, applicator 7100 may be configured such that activation element 7104 may be activated first, but that actual insertion is not triggered until outer housing 7101 is translated sufficiently in the distal direction toward and with respect to inner housing 7102. In yet other embodiments, activation element 7104 may be biased toward a center of applicator 7100 such that activation element 7104 need not be explicitly activated by the host but, instead, activation element 7104 may be configured to automatically initiate insertion upon outer housing 7101 being translated sufficiently in the distal direction toward and with respect to inner housing 7102.

By way of example, FIG. 6C illustrates a bridge-based sensor or switch that may be used in connection with activation of analyte sensor system 308. FIG. 6C shows portions of analyte sensor electronics module 600 that is connectable to analyte sensor 602 using first and second contacts 604 and 606. For example, analyte sensor electronics module 600 may be connected to analyte sensor 602 before analyte sensor 602 is implanted in the user. Analyte sensor electronics module 600 may include conductive bridge 612 (e.g., a jumper), which may be configured to electrically couple first and second contacts 604 and 606 to one another to form a bridge during deployment/application of analyte sensor system 308. Conductive jumper 612 can be located at least partially between two electrical connections of analyte sensor system 308. Conductive jumper 612 can include two springs 608 coupled by conductive link 616, where conductive jumper 612 and springs 608 are supported by housing 614 of analyte sensor system 308. During deployment/application of analyte sensor system 308, springs 608 may be deflected such that springs 608 electrically connect to one another through physical contact, thus forming a bridge that may be used to trigger activation of analyte sensor system 308.

Referring back to FIG. 5, and with reference being made to FIG. 6C by way of example, activation detection circuit 520 and/or activation detection component 545 may include a non-conductive separation tab-based sensor or switch that may be used to cause analyte sensor system 308 to exit a lower power state in various embodiments. For example, a non-conductive material may be placed between spring-loaded electrical contacts. The removal of the nonconductive material may then cause the spring-loaded electrical contacts to form a physical/electrical connection, electrically coupling the contacts. The connection of these spring-loaded electrical contacts may be used to connect power (e.g., from a battery of analyte sensor system 308) and/or to trigger circuit wakeup (e.g., as a wakeup pin) and cause analyte sensor system 308 to exit a lower power state.

In embodiments, activation detection circuit 520 and/or activation detection component 545 may include a strain/force-based sensor that may be used to cause analyte sensor system 308 to exit a lower power mode. One or more sensors may be included in analyte sensor system 308 that may be capable of detecting a strain (e.g., total deformation divided by initial dimension of the body) or a force placed on a housing/body of analyte sensor system 308. Such strain or force may be applied, for example, by an applicator gripping analyte sensor system 308. In some examples, a strain gauge may be used on the interior of the housing of analyte sensor system 308, where the strain gauge may be electrically coupled to activation detection circuit 520, for example, through routing on a printed circuit board, etc. The strain gauge may be placed on our coupled to a Wheatstone bridge. The strain gauge may vary a resistance value which can be monitored using the Wheatstone bridge. Various types of strain gauge configurations may be used in connection with the Wheatstone bridge, for example, quarter-, half-, and full-bridges may be used depending upon the orientation of the strain gauges and type of strain being measured. The strain/force measurement may also be used to detect a momentary action such as the forces of acceleration during deployment of analyte sensor system 308 and/or the impact of analyte sensor system 308 on the user's body. For example, the strain/force measurement may be used to effect triggers 906 and/or 910, with reference to FIG. 9.

In certain embodiments, activation detection circuit 520 and/or activation detection component 545 may include additional components that may be added internally to or externally from analyte sensor system 308 specifically for creating detectable events that may be used to trigger activation of analyte sensor system 308 without user intervention. In one example, a current generating component may be used in conjunction with analyte sensor system 308 for activation purposes. For instance, magnetizing or adding a magnetic element to the applicator needle or needle hub may be used for activation purposes. As analyte sensor system 308 is deployed, the magnetic needle or auxiliary magnetic rod can be retracted in relation to analyte sensor system 308. Activation detection component 545 may include induction coils or an NFC antenna, for example on the perimeter of analyte sensor system 308, that may be used to generate current (e.g., or other electrical signal) via electromagnetic response. The motion of the applicator withdrawing the needle, rod, or other magnetic element can create relative motion between the same and the coil/antenna of analyte sensor system 308. This current or other electrical signal can then be used to trigger activation of analyte sensor system 308. In some cases, analyte sensor system 308 may already include an NFC antenna, and thus this feature may not require the addition of components to analyte sensor system 308.

In another example, a piezoelectric component can be used, where the piezoelectric component generates a voltage in response to a force (e.g., impact force) that may occur during deployment of analyte sensor system 308. For example, a quartz crystal may be included in activation detection circuit 520 and/or activation detection component 545, where a voltage generated by the crystal spikes or increases when analyte sensor system 308 experiences impact from the deployment, thus triggering analyte sensor system 308 to exit the lower power state.

Exiting the Lower Power State in Response to User-Based Input

In certain embodiments, switches/sensor/mechanisms/techniques can be employed to detect a user step and trigger activation of analyte sensor system 308 using the same, either alone or in combination with other activation detection techniques/means described herein. Such switches/sensors/mechanisms/techniques may typically rely upon user intervention/action. In some examples, a detection switch/element/sensor can be placed on analyte sensor system 308 and used to trigger activation or exit from a lower power state. By way of example, at least part of activation detection component 545 may include a detection element/component that is external to analyte sensor system 308, such as a removable sticker on a surface of analyte sensor system 308. In response to the user peeling/removing the sticker, analyte sensor system 308 may be triggered to exit the lower power state. As another example, the detection element may be a feature of the applicator, packaging, box, or a tray associated with the delivery of analyte sensor system 308. Here, reference is made to FIGS. 6A and 6B, for example. In some cases, the detection element may be a component placed in the packaging near analyte sensor system 308.

The detection element may contain a conductive material (e.g., metal, graphite, etc.), and, in embodiments, a sensor (e.g., that uses capacitive, inductive magnetic, RF, or other type of sensing, for example as described herein) may detect the removal of the conductive material when the detection element is removed by the user. In certain embodiments, the detection element may include a tag device (e.g., RFID sticker or the like) that may be placed on a surface of analyte sensor system 308 during manufacturing/assembly of the same. A reader (e.g., NFC, RFID, etc.) may then detect the removal of the tag and trigger activation. For example, ping messages may be exchanged when the tag device is in place but the exchange may stop occurring once the tag device is removed, thus triggering activation.

In some cases, the detection element may be optically opaque such that removing the detection element may expose a photosensor to light, thus triggering activation. For example, a photosensor may be exposed to the light by a sticker being pulled off to uncover the photosensor. Alternatively, the detection element may be optically tinted (e.g., green or another color). As such removal of the detection element may result in a shift in wavelength that can be detected using a photosensor. By way of example the shift in color may go from green to white or the like, and the change in color may be used to trigger activation.

Certain of the above-described electromechanical detection techniques may be employed in connection with embodiments that utilize a user step for purposes or activating analyte sensor system 308. For example, the user may push a button, pull a tab, take a step that forms or breaks a bridge, etc. to trigger activation of analyte sensor system 308. The user can be instructed to take such a step before or after analyte sensor 10 implantation, or within a certain time window thereof.

In embodiments, a signal from an external device or a signal generated based on user input may be used to trigger activation of analyte sensor system 308. By way of example, the display of an electronic device (e.g., smartphone, proprietary analyte display device, or smartwatch, referencing FIG. 1) can be used to direct light (e.g., from a flash or screen of the device, as mentioned above), audio (e.g., frequency), or vibration to analyte sensor system 308. Activation detection circuit 520 and/or activation detection component 545 can then be used to detect such external stimuli via, for example, a photodiode, microphone, or piezoelectric sensor, and in response thereto to trigger activation. In one example, a user may tap a pattern on analyte sensor 308 that can be detected using a microphone and/or an accelerometer and used to trigger activation. An accelerometer of analyte sensor system 308 may also use pattern detection, for example, of the human gait/walk, for activation purposes. That is, if analyte sensor system 308 detects that it is moving in accordance with the human gait, it can be inferred that implantation of analyte sensor 530 has occurred.

It should be appreciated that each of the above-described techniques can be used alone or in combination with any of the other above-described techniques for purposes of causing analyte sensor system 308 to exit a lower power state. The technique(s) employed may depend upon system design considerations, for example, including considerations regarding power consumption, weight, size, and level of user interactivity, among other considerations.

Utilizing a State-Machine for Exiting the Lower Power State

One or more embodiments as disclosed herein may utilize impedance measurements and/or current counts indicative of a current flowing through an analyte sensor (e.g., analyte sensor 530 of FIG. 5) to determine when the analyte sensor has been deployed into a skin of a host and, therefore, when at least a portion of sensor electronics (e.g., analyte sensor system 308 of FIG. 5 by way of example and not limitation) should exit a lower power "storage" or "sleep" mode and "wake up" to begin processing one or more samples of a sensor signal and/or sensor data. Additionally, or alternatively, such current counts and/or impedance measurements may be utilized once such analyte sensor system 308 sensor electronics has entered a powered "run" mode to periodically or randomly calibrate or recalibrate analyte sensor 530 and/or to monitor a sensitivity of analyte sensor 530.

Some embodiments can utilize a clocked processor-based controller (e.g., processor/microcontroller 535 of FIG. 5) to provide one or more pulsed voltages across the terminals of analyte sensor 530, perform consecutive current count and/or impedance measurements or determinations of analyte sensor 530 based on a response to the pulsed voltages, average and analyze the current count and/or impedance measurements. Such pulsed voltages may have durations on the order of milliseconds and accurate estimation of an average current flowing through analyte sensor 530 and/or an impedance of analyte sensor 530 can require many current count samples (e.g., 125) to be averaged over an extended period of time (e.g., 10-12 seconds). While such controller-based solutions have been shown to work, constantly powering clocked processor-based controller 535 during the sample acquisition process requires a significant amount of power and can cause on-board batteries to last for only a fraction of their rated capacities.

One solution, as will be described in more detail below in connection with at least FIGS. 12-15, is to offload such a controller-based method for measuring and/or determining current counts indicative of a current flowing through analyte sensor 530 to a hardware-based state machine (e.g., state machine 1430 of FIG. 14), which consumes considerably less power than clocked processor-based controller 535. In such solutions, clocked processor-based controller 535 can set up one or more parameters of state machine 1430 and then enter a lower power "sleep" state, rather than performing all actions by itself, staying "awake," and undesirably draining the battery. In some embodiments, state machine 1430 can be implemented utilizing one or more registers (e.g., parameter register 1436 of FIG. 14), one or more counters (e.g., counter 1434 of FIG. 14) and/or one or more memories (e.g., a portion of storage 515 of FIG. 5).

While controller 535 is in the lower power "sleep" state, state machine 1430 can be tasked with controlling the application of one or more pulsed voltages across the terminals of analyte sensor 530, controlling the measurement of a current induced in analyte sensor 530 by the one or more pulsed voltages, and storing one or more data samples (e.g., digital counts) based on the current response. Controller 535 may then wake up, responsive to an interrupt or wake signal from state machine 1430, to process the one or more stored data samples, the number of which may be variable based on the particular implementation. Such a solution can reduce the overall power consumption of analyte sensor system 308, in some cases by 50-60% or more, compared to the above-described data acquisition process utilizing only clocked processor-based controller 535.

State machine 1430 can be utilized to capture, at least partly process, and/or store current counts corresponding to a current flowing through the analyte sensor during a "storage" mode, when the controller is largely "sleeping," or during a "run" mode when continuous analyte (e.g., glucose) measurements are being measured, determined, estimated and/or otherwise processed.

During such a "storage" mode, an analog front end (AFE) of the analyte sensor system (e.g., at least a portion of sensor measurement circuitry 525 of FIG. 5) can wake periodically (e.g., every 64 seconds) and perform one or more current count measurements indicative of a current flowing through analyte sensor 530 to determine whether analyte sensor 530 has been inserted into the skin of the host, indicating that a transition from "storage" mode to a "run" mode or "wake" state is appropriate. This process can also be utilized to differentiate current count values indicative of analyte sensor 530 being properly inserted into the skin from current count values indicative of analyte sensor 530 being subjected to environmental conditions (e.g., high relative humidity) that may falsely indicate sensor insertion into the skin of the host. Accordingly, this process can help to avoid false wakeup of controller 535 due to, e.g., high relative humidity conditions, as detailed below. For example, when analyte sensor 530 is inserted into the skin of the host, a relatively moderate to lower impedance (e.g., several hundred kΩ) of analyte sensor 530 will result in a certain observed current flow through analyte sensor 530. However, when a relative humidity is sufficiently high (e.g., >90%) but analyte sensor 530 is not inserted into the skin of the host, a relatively high, but not open-circuit, impedance (e.g., 1.6 MΩ) of analyte sensor 530 will result in a different observed current flow through analyte sensor 530, where the higher the relative humidity, the greater the observed current flow through analyte sensor 530 will be (see, e.g., FIG. 7C). State-machine 1430 described herein can allow differentiation between these two states such that these environmental conditions (e.g., sufficiently high relative humidity) do not inadvertently trigger a false wakeup of controller 535, thereby further reducing power consumption due to unnecessary and inappropriate waking of controller 535.

Figure 12:
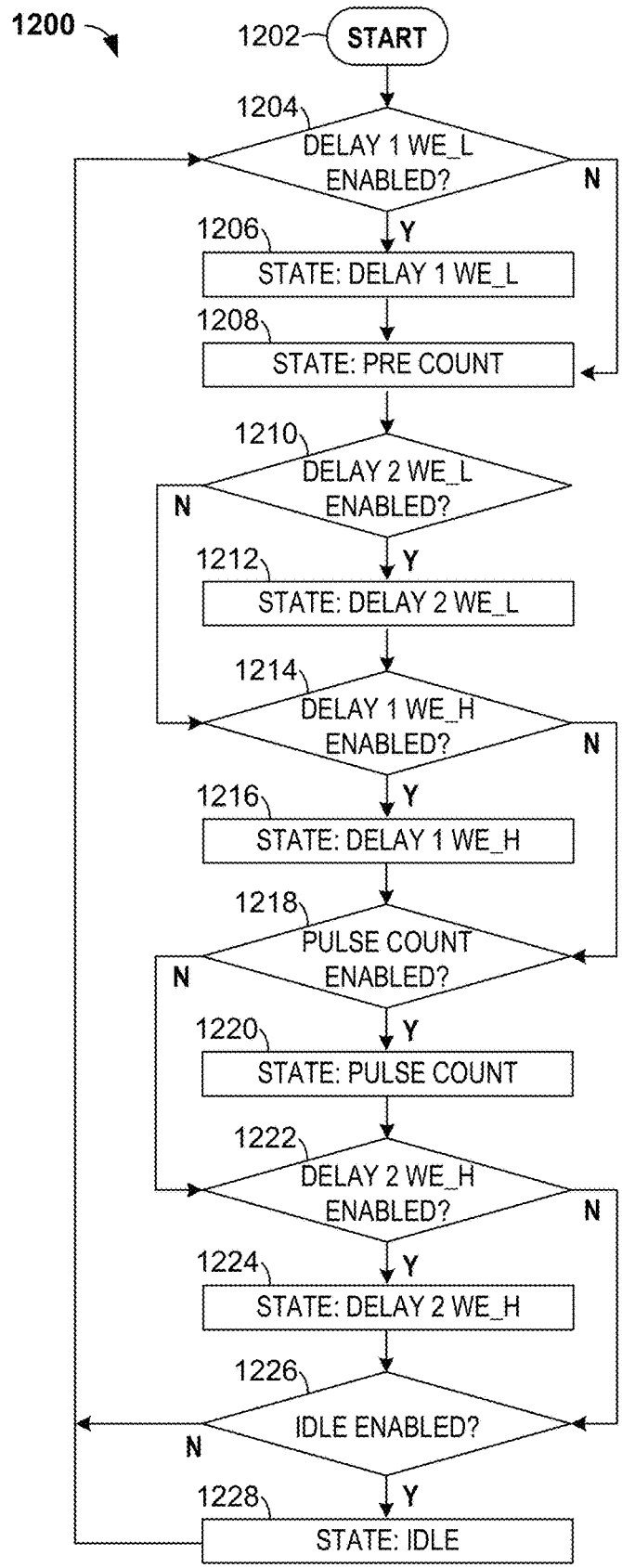
FIG. 12 illustrates a timing diagram related to a state-machine for ultimately determining an impedance of an analyte sensor, in accordance with some embodiments.
Figure 13:
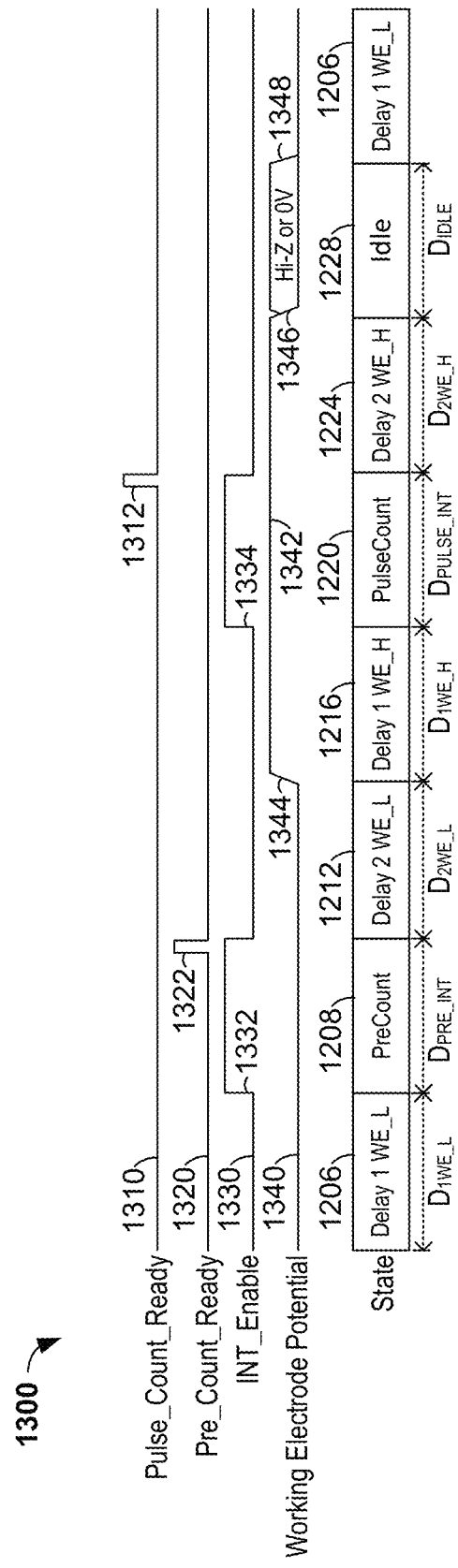
FIG. 13 illustrates a state diagram related to a state-machine for ultimately determining an impedance of an analyte sensor, in accordance with some embodiments.
Figure 14:
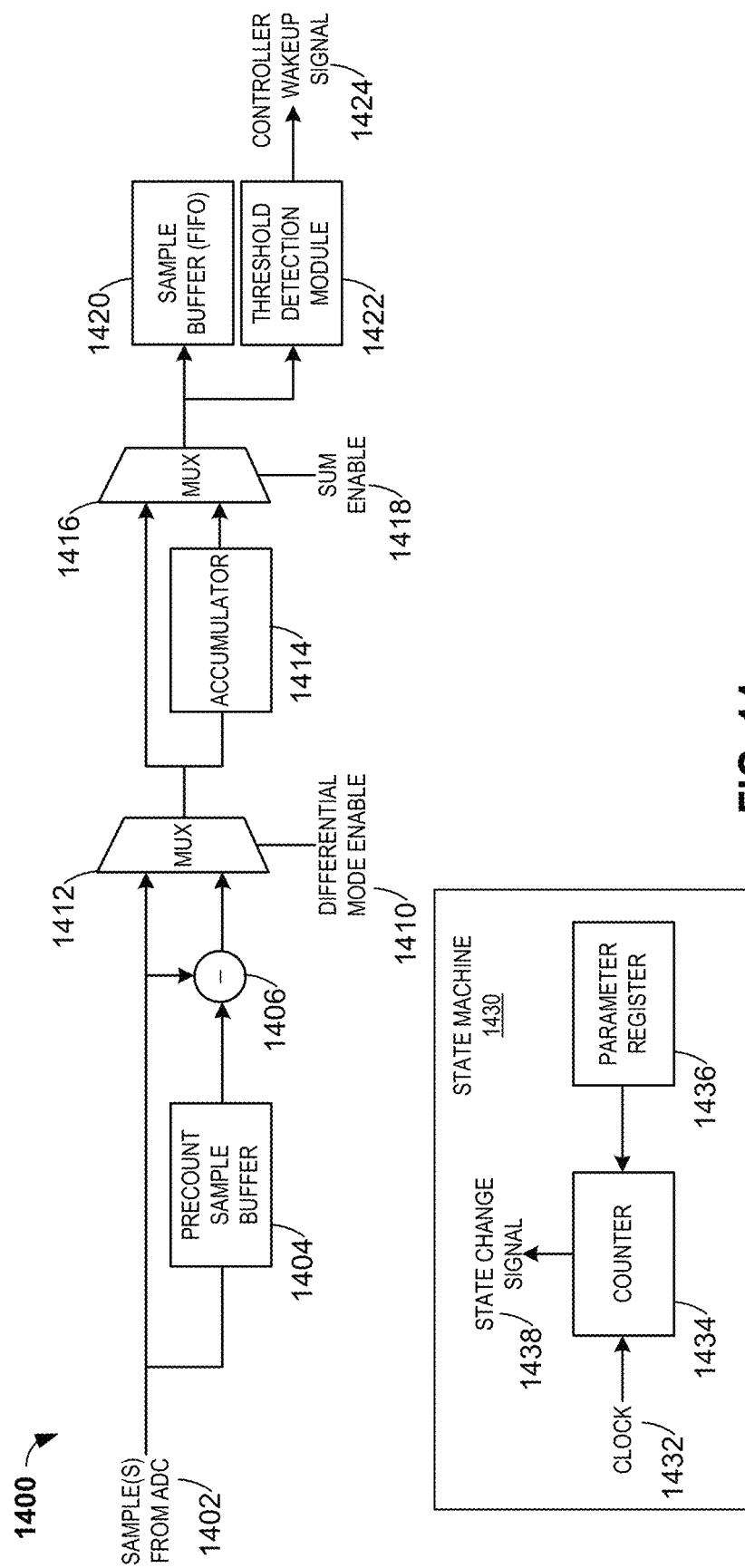
FIG. 14 illustrates a functional block diagram related to a state-machine for ultimately determining an impedance of an analyte sensor, in accordance with some embodiments.

FIG. 12 illustrates a state diagram 1200 related to, e.g., state machine 1430 of FIG. 14, at least for determining one or more current counts indicative of a current flowing through analyte sensor 530, in accordance with some embodiments. State diagram 1200 illustrates 7 potential states: 5 potential delay states (e.g., delay 1 WE_L state 1206, delay 2 WE_L state 1212, delay 1 WE_H state 1216, delay 2 WE_H state 1224, and idle state 1228) and two potential sampling states (e.g., pre-count sampling state 1208 and pulse count sampling state 1220). While operation of state machine 1430 is described in more detail below in connection with FIGS. 13-15, a brief overview here can be helpful in understanding the function and utility of the different states.

In order to ultimately determine an impedance of analyte sensor 530, a known voltage may be applied across the terminals of analyte sensor 530 and Ohm's Law can be used to determine the impedance based on the current generated by that known voltage. However, the current generated by the known voltage can have components that are not necessarily directly attributable to, e.g., a membrane impedance of analyte sensor 530, but to other environmental factors. Accordingly, an impedance determined based on a single current or current count measured in response to application of the known voltage across the sensor terminals may not accurately reflect the actual membrane impedance of analyte sensor 530 and, therefore, may not be a reliable indicator for changing a state of analyte sensor system 308, e.g., from a "sleep" or "storage" state to a "wake" or "run" state. Accordingly, it can be desirable to utilize a plurality of current or current count measurements for making such a state change determination.

Accordingly, a first current count value may be determined while a working electrode of analyte sensor 530 is held at a first potential. This first current count may be considered a baseline value. The working electrode of analyte sensor 530 can then be held at a second potential greater than the first potential and a second current count value may be determined. This second current count value may be considered a pulse value. If the interval between measurement of the first and second current count values is sufficiently small, subtracting the first current count value from the second current count value can reliably remove much of the effect of environmental factors from the measurements and an accurate membrane impedance value for analyte sensor 530 can be obtained therefrom based on an understanding that such impedance would be inversely related to the difference between the first and second current counts, since with such sufficiently small intervals between measurements, the effects of such environmental factors can be assumed to have a similar effect on both the first and the second current counts.

However, when the first and second potentials are applied across the terminals of analyte sensor 530, the initial instantaneous currents induced through analyte sensor 530 will not be indicative of the sensor's steady-state impedance, as determined according to Ohm's Law, due to the RC characteristics of analyte sensor 530, for example as previously described in connection with FIG. 7A. Accordingly, implementing one or more delay states 1206, 1212, 1216, 1224 can ensure that current counts measured during sampling states 1208, 1220 are not substantially affected by the initial dynamics of the RC characteristics of analyte sensor 530.

As illustrated in FIG. 12, the order of states 1206, 1208, 1212, 1216, 1220, 1224 and 1228 are always the same, but all states except pre-count sampling state 1208 can be bypassed according to a pre-configuration of state machine 1430 (see FIG. 14) and/or an associated parameter register 1436 (see FIG. 14) by controller 535. Each state in FIG. 12 can also have a pre-configured duration. A counter (e.g., counter 1434 of FIG. 14) can count continuously during each enabled state until a configurable absolute value is reached, triggering a change to the next enabled state and a reset of counter 1434 for timing the next enabled state. In some embodiments, this process allows a single counter 1430 to time all enabled states of state machine 1430, thereby simplifying analyte sensor system design and reducing associated fabrication costs.

State diagram 1200 starts at start block 1202 and advances to block 1204, which determines whether a first delay state 1206 (e.g., delay 1 WE_L) is enabled. If first delay state 1206 is disabled, state diagram 1200 advances from block 1204 directly to a first sampling state 1208. If first delay state 1206 is enabled, state diagram 1200 advances to first delay state 1206, which can last for a configurable duration, e.g., ~1-2 milliseconds or any other suitable duration. At initiation of first delay state 1206, state machine 1430 can apply or control application of a first voltage potential to a working electrode of analyte sensor 530. No current count measurements are captured by state machine 1430 and/or by supporting hardware or software as shown in at least FIG. 14 during first delay state 1206.

Upon expiration of first delay state 1206, state diagram 1200 advances to first sampling state 1208, during which the first voltage is maintained at the working electrode of analyte sensor 530 and one or more samples (e.g., digital counts) corresponding to the current induced in analyte sensor 530 by the first voltage potential are captured and/or processed by state machine 1430 and/or supporting hardware or software as shown in at least FIG. 14. First sampling state 1208 can last for a configurable duration, e.g., ~2 s to 300 seconds, depending on the application.

Upon expiration of first sampling state 1208, state diagram 1200 advances to block 1210, which determines whether a second delay state 1212 (e.g., delay 2 WE_L) is enabled. If second delay state 1212 is disabled, state diagram 1200 advances from block 1210 directly to block 1214. If second delay state 1212 is enabled, state diagram 1200 advances to second delay state 1212, which can last for a configurable duration, e.g., ~1-2 milliseconds or any other suitable duration. State machine 1430 can maintain or control the maintenance of the first voltage potential at the working electrode of analyte sensor 530 for the duration of second delay state 1212. No current count measurements are captured by state machine 1430 and/or by supporting hardware or software as shown in at least FIG. 14 during second delay state 1212.

Upon expiration of second delay state 1212, state diagram 1200 advances to block 1214, which determines whether a third delay state 1216 (e.g., delay 1 WE_H) is enabled. If third delay state 1216 is disabled, state diagram 1200 advances from block 1214 directly to block 1218. If third delay state 1216 is enabled, state diagram 1200 advances to third delay state 1216, which can last for a configurable duration, e.g., ~1-2 milliseconds or any other suitable duration. At initiation of third delay state 1216, state machine 1430 can apply or control application of a second voltage potential greater than the first voltage potential to the working electrode of analyte sensor 530. Initial current flow through analyte sensor 530 due to the RC characteristics of analyte sensor 530 can occur and substantially dampen out during third delay state 1216. Accordingly, no current count measurements are captured by state machine 1430 and/or by supporting hardware or software as shown in at least FIG. 14 during third delay state 1216.

Upon expiration of third delay state 1216, state diagram 1200 advances to block 1218, which determines whether a second sampling state 1220 is enabled. If second sampling state 1220 is disabled, state diagram 1200 advances from block 1218 directly to block 1222. If second sampling state 1220 is enabled, state diagram 1200 advances to second sampling state 1220, during which the second voltage is maintained at the working electrode of analyte sensor 530 and one or more samples (e.g., digital counts) corresponding to the current induced in analyte sensor 530 by the second voltage potential are captured and/or processed by state machine 1430, as will be describe in more detail below in connection with FIGS. 13-15. Second sampling state 1220 can last for a configurable duration, e.g., ~3-4 milliseconds, depending on the application.

Upon expiration of second sampling state 1220, state diagram 1200 advances to block 1222, which determines whether a fourth delay state 1224 (e.g., delay 2 WE_H) is enabled. If fourth delay state 1224 is disabled, state diagram 1200 advances from block 1222 directly to block 1226. If fourth delay state 1224 is enabled, state diagram 1200 advances to fourth delay state 1224, which can last for a configurable duration, e.g., ~1-2 milliseconds or any other suitable duration. State machine 1430 can maintain or control the maintenance of the second voltage potential at the working electrode of analyte sensor 530 for the duration of fourth delay state 1224. No current count measurements are captured by state machine 1430 and/or by supporting hardware or software as shown in at least FIG. 14 during fourth delay state 1224.

Upon expiration of fourth delay state 1224, state diagram 1200 advances to block 1226, which determines whether a fifth delay state 1228 (e.g., an extended idle state) is enabled. If fifth delay state 1226 is disabled, state diagram 1200 advances from block 1226 directly back to block 1204 and state machine 1430 runs through state diagram 1200 again. If fifth delay state 1228 is enabled, state diagram 1200 advances to fifth delay state 1228, which can last for a configurable duration, e.g., ~1 millisecond to 64 seconds or any other suitable duration. At initiation of fifth delay state 1228, state machine 1430 can reapply or control the reapplication of the first voltage potential to the working electrode of analyte sensor 530, can provide or control provision of 0V to the working electrode of analyte sensor 530, or can provide or control provision of an open-circuit voltage (e.g., high-Z state) to the working electrode of analyte sensor 530 (e.g., by opening a switch in the circuit including analyte sensor 530). This potential can be maintained at the working electrode for the duration of fifth delay state 1228. No current count measurements are captured by state machine 1430 and/or by supporting hardware or software as shown in at least FIG. 14 during fifth delay state 1228.

In some embodiments, enablement of fifth delay state 1228 can be reserved for operation of state machine 1430 during storage mode, when analyte sensor 530 is not actively measuring analyte values and during which samples may only be collected intermittently during first and/or second sampling states 1208, 1220, which occur between longer periods of inactivity defined primarily by the duration of fifth delay state 1228.

Moreover, the first and second voltages described above can be fully configurable and, in some cases, independently configurable from one another. For example, the first and second voltages may be programmable from 0V to 1V in ~16 mV steps (e.g., 64 steps). In addition, the first and second voltages may each have different values depending on whether analyte sensor system 308 is currently in a "storage" mode, during which analyte sensor 530 is not inserted into the skin of the host, or in a "run" mode, during which analyte sensor 530 is inserted into the skin of the host and continuous and/or intermittent glucose measurements are being taken, determined and/or otherwise captured. For example, in such a "run" mode, the first voltage can be 0.6V and the second voltage can be 0.616V (e.g., 16 mV greater than the first voltage), while in such a "storage" mode, the first voltage can be 0V and the second voltage can be 0.016V (e.g., 16 mV greater than the first voltage).

In some embodiments, utilization of 0V for the first voltage during "storage" mode may be advantageous since applying defined, non-zero bias voltages across the terminals of analyte sensor 530 for extended periods of time can cause accelerated oxidation and/or damage to sensor 530. For similar reasons, applying an open-circuit voltage (e.g., a high-Z state), or alternatively 0V, to the working electrode of analyte sensor 530 during fifth delay state 1228 can help to ensure that no potentially damaging bias voltage is applied across the terminals of analyte sensor 530 for the often extended durations of fifth delay state 1228, thereby reducing oxidation or other damage to analyte sensor 530 during "storage" mode before analyte sensor 530 is deployed into the skin of the host.

Moreover, while examples of the durations of each of the states in state diagram 1200 are given above, the present disclosure is not so limited and any suitable durations are contemplated. In some embodiments, counter 1434 of FIG. 14 may comprise a configurable-bit counter. For example, counter 1434 may be configured as a 10-bit counter having a maximum value of 1 second and being configurable in ~976 microsecond (e.g., $1/1,024^{th}$ of a second) increments when timing each of first delay state 1206, second delay state 1212, third delay state 1216, second sampling state 1220, and fourth delay state 1224. In some embodiments, counter 1434 may be configured as a 19-bit counter having a maximum value of 8.53 minutes and being configurable in ~976 microsecond (e.g., $1/1,024^{th}$ of a second) increments when timing each of first sample state 1208 and fifth delay state 1228.

Operation of analyte sensor system 308 will be further discussed in connection with timing diagram 1300 of FIG. 13 and functional block diagram 1400 of FIG. 14 together below, in accordance with some embodiments.

Timing diagram 1300 of FIG. 13 illustrates example timing of several signals in relation to one or more of the states previously described in connection with state diagram 1200 of FIG. 12.

A Pulse_Count_Ready signal 1310 can be utilized to signal that a current count, corresponding to a current flowing through analyte sensor 530, determined and integrated by an analog-to-digital converter (ADC) of an analog front end (AFE) (e.g., sensor measurement circuitry 525) during second sampling state 1220, is ready for transmission to one or more modules of FIG. 14.

A Pre_Count_Ready signal 1320 can be utilized to signal that a current count, corresponding to a current flowing through analyte sensor 530, determined and integrated by the ADC of the AFE during first sampling state 1208, is ready for transmission to one or more modules of FIG. 14.

An INT_Enable signal 1330 can be utilized to signal the ADC of the AFE to integrate the current counts corresponding to the current flowing through analyte sensor 530 during one or both of the first and second sampling states 1208, 1220, based on signal 1330 being high at 1332 and 1334. Timing diagram 1300 also illustrates an example working electrode potential 1340 for analyte sensor 530 as applied during one or more of states 1206, 1208, 1212, 1216, 1220, 1224, 1228.

Block diagram 1400 of FIG. 14 illustrates example features of state machine 1430 and at least some hardware- and/or software-based features of, e.g., sensor measurement circuitry 525, activation detection circuit 520 and/or activation detection component 545 as previously described in connection with at least FIG. 5.

For example, block diagram 1400 illustrates state machine 1430, which can include a parameter register 1436 configured to store one or more parameters for one or more states of state machine 1430, e.g., as previously described in connection with FIG. 12. For example, parameters register 1436 can store indications of whether each potential state of state diagram 1200 is enabled and indications of one or more configurable counter values corresponding to a duration of each potential state of state diagram 1200. In some embodiments, one or more of the parameters of parameters register 1436 can be configured by controller 535 before controller 535 enters a sleep or lower power mode.

State machine 1430 can further include a counter 1434 configured to count continuously during each enabled state until a configurable counter value is reached. Such a configurable counter value can be defined by parameter register 1436. Counter 1434 reaching a configurable counter value can trigger a state change signal 1438 for advancing state machine 1430 to the next enabled state. Counter 1434 can be configured to reset based on reaching the configurable counter value for a particular state and begin counting for the timing of the next enabled state. As illustrated, counter 1434 can receive a clock signal 1432 coordinating such counting. In some embodiments, clock signal 1432 can be derived from a clock signal of the ADC of the AFE. For example, the ADC clock signal can be a 32 kHz clock signal provided by, e.g., a highly accurate quartz crystal. In some embodiments, this ADC clock signal can be divided by 32 to obtain clock signal 1432, having a frequency of 1,024 Hz. However, the present disclosure is not so limited and clock signal 1432 can be obtained and/or generated in any suitable method and can have any suitable frequency.

Block diagram 1400 further illustrates a pre-count sample buffer 1404 configured to receive and temporarily store one or more current count samples 1402 generated by the ADC based on a current flowing through analyte sensor 530 during pre-count sampling state 1208.

Block diagram 1400 further illustrates a differentiator 1406 configured to subtract the current count sample stored in precount sample buffer 1404 from a subsequently received current count sample 1402 generated by the ADC based on a current flowing through analyte sensor 530 during pulse-count sampling state 1220. Differentiator 1406 can output the difference value to a multiplexor (MUX) 1412. Based on a differential mode enable signal 1410, MUX 1412 can be configured to either pass current count samples 1402 directly from the ADC (e.g., differential mode enable=0) or pass the calculated difference value from differentiator 1406 (e.g., differential mode enable=1).

Block diagram 1400 further illustrates an accumulator 1414 configured to accumulate (e.g., integrate or sum) consecutive samples received from MUX 1412 and output an accumulated, integrated or summed sample to MUX 1416. Based on a sum enable signal 1418, MUX 1416 can be configured to either pass current count samples 1402 directly from MUX 1412 (e.g., sum enable=0) or pass the accumulated, integrated or summed sample from accumulator 1414 (e.g., sum enable=1).

Block diagram 1400 further illustrates a sample buffer 1420 (e.g., a first-in-first-out FIFO buffer) configured to receive and store one or more samples from MUX 1416. In some embodiments, sample buffer 1420 is configured to concurrently store up to 16 samples. However, the present disclosure is not so limited and sample buffer 1420 can be configured to concurrently store any number of samples, according to the particular implementation. However, in general, the more samples sample buffer 1420 is configured to store concurrently, the more power sample buffer 1420 would require.

A threshold detection module 1422 can be configured to determine whether a configurable number of consecutive or non-consecutive samples, output from MUX 1416, satisfy a predetermined and/or configurable threshold value. Threshold detection module 1422 can be configured to generate a controller wake-up signal 1424 based on satisfaction of the predetermined threshold value by the configurable number of consecutive or non-consecutive samples. Controller 535 can be configured to wake up, responsive to controller wake-up signal 1424, and further process the samples stored in sample buffer 1420 and/or transmit or control transmission of a signal based on such processing. In some embodiments, controller 535 can be configured to reenter the lower power sleep mode upon completion of such processing and/or signal transmission while the above-described process(es) are repeated.

An example state-by-state operation will now be described in connection with FIGS. 13 and 14 wherein all delay states and all sampling states of state machine 1430, as previously described in connection with FIG. 12, are enabled. For example, in some embodiments of a storage mode, state-by-state operation, differential mode enable signal 1410 and sum enable signal 1418 can both be set to high, such that MUX 1412 will ultimately pass an output of differentiator 1406 and MUX 1416 will ultimately pass an output of accumulator 1414.

As illustrated in FIG. 13, state machine 1430 can initially enter first delay state 1206. A first potential 1340 (e.g., 0V in "storage" mode, 0.6V in "run" mode) is applied to the working electrode of analyte sensor 530 during first delay state 1206. INT_enable signal 1330 is low during first delay state 1206. Accordingly, the ADC of sensor measurement circuitry 525 is not integrating and/or accumulating current counts corresponding to current flowing through analyte sensor 530 during first delay state 1206. Counter 1434 receives clock signal 1432 and continuously increments until a configurable absolute value, defined by parameter register 1436, is reached. Upon reaching the configurable absolute value, counter 1434 and/or another portion of state machine 1430 generates state change signal 1438, triggering a change to pre-count sampling state 1208 and a reset of counter 1434.

First potential 1340 (e.g., 0V in "storage" mode, 0.6V in "run" mode) is maintained at the working electrode of analyte sensor 530 for the duration of pre-count sampling state 1208. INT_Enable signal 1330 is set to high, e.g., at 1332, for the duration of pre-count sampling state 1208. Accordingly, the ADC of sensor measurement circuitry 525 integrates and/or accumulates current counts corresponding to a current flowing through analyte sensor 530 for the duration of pre-count sampling state 1208.

During pre-count sampling state 1208, counter 1434 receives clock signal 1432 and continuously increments until a configurable absolute value, defined by parameter register 1436 and corresponding to a duration of pre-count sampling state 1208, is reached. Upon reaching the configurable absolute value, counter 1434 or another portion of state machine 1430 generates state change signal 1438, which causes state machine 1430 to advance to second delay state 1212, sets INT_Enable signal 1330 to low, which signals the ADC to stop accumulating the current count sample, generates a pulse 1322 in Pre_Count_Ready signal 1320, which signals the ADC to output an accumulated current count sample 1402 to pre-count sample buffer 1404, and resets counter 1434. This accumulated current count sample 1402 can signify an average current flowing through analyte sensor 530 during pre-count sampling state 1208. While a single-arrow signal line is illustrated, the accumulated current count sample 1402 can comprise a multi-bit (e.g., 10- or 19-bit) sample value transmitted in parallel from the ADC to precount sample buffer 1404 via a parallel (e.g., 10- or 19-bit) data bus. Unless otherwise stated, all samples passed by other signal pathways in FIG. 14 can be similar multi-bit sample values transmitted in parallel via similar parallel data buses indicated by the signal arrows in FIG. 14.

Continuing with the discussion in relation to FIG. 13, first potential 1340 (e.g., 0V in "storage" mode, 0.6V in "run" mode) is maintained at the working electrode of analyte sensor 530 for the duration of second delay state 1212. INT_enable signal 1330 is low during second delay state 1212, so the ADC of sensor measurement circuitry 525 is not integrating and/or accumulating current counts corresponding to current flowing through analyte sensor 530 during second delay state 1212. Counter 1434 receives clock signal 1432 and continuously increments until a configurable absolute value, defined by parameter register 1436, is reached. Upon reaching the configurable absolute value, counter 1434 or another portion of state machine 1430 generates state change signal 1438, which triggers a change to third delay state 1216 and a reset of counter 1434.

At the onset of third delay state 1216, a second potential 1342 (e.g., 16 mV in "storage" mode, 0.616V in "run" mode) is applied to the working electrode of analyte sensor 530 and maintained for the duration of third delay state 1216. During at least the rising edge 1344 of second potential 1342, a current flowing through analyte sensor 530 will be substantially dominated by the RC characteristics of analyte sensor 530, which will substantially dampen out during third delay state 1216. INT_enable signal 1330 is low during third delay state 1216, so the ADC of sensor measurement circuitry 525 is not integrating and/or accumulating current counts corresponding to current flowing through analyte sensor 530 during third delay state 1216. Counter 1434 receives clock signal 1432 and continuously increments until a configurable absolute value, defined by parameter register 1436, is reached. Upon reaching the configurable absolute value, counter 1434 or another portion of state machine 1430 generates state change signal 1438, which triggers a change to pulse count state 1220 and a reset of counter 1434.

Second potential 1342 (e.g., 16 mV in "storage" mode, 0.616V in "run" mode) is maintained at the working electrode of analyte sensor 530 for the duration of pulse count sampling state 1220. INT_Enable signal 1330 is set to high for the duration of pulse count sampling state 1220. Accordingly, the ADC of sensor measurement circuitry 525 integrates and/or accumulates current counts corresponding to a current flowing through analyte sensor 530 for the duration of pulse count sampling state 1220.

During pulse count sampling state 1220, counter 1434 receives clock signal 1432 and continuously increments until a configurable absolute value, defined by parameter register 1436, is reached. Upon reaching the configurable absolute value, counter 1434 or another portion of state machine 1430 generates state change signal 1438, which causes state machine 1430 to advance to fourth delay state 1224, sets INT_Enable signal 1330 to low, which signals the ADC to stop accumulating the current count sample, generates a pulse 1312 in Pulse_Count_Ready signal 1310, which signals the ADC to output an accumulated current count sample 1402 to differentiator 1406, and resets counter 1434. This accumulated current count sample 1402 can signify an average current flowing through analyte sensor 530 during pulse count sampling state 1220.

Differentiator 1406 is configured to subtract the accumulated current count sample 1402 stored at the end of pre-count sampling state 1208 from the accumulated current count sample 1402 generated at the end of pulse count sampling state 1220 and output a differential current count sample to MUX 1412. Differentiator 1406 can be configured to set this differential current count sample to zero if the result would otherwise be a negative number. Since differential mode enable signal 1410 is set to high, MUX 1412 passes the differential current count sample to accumulator 1414, which stores the differential current count sample.

Second potential 1342 (e.g., 16 mV in "storage" mode, 0.616V in "run" mode) is maintained at the working electrode of analyte sensor 530 for the duration of fourth delay state 1212. INT_enable signal 1330 is low during fourth delay state 1224, so the ADC of sensor measurement circuitry 525 is not integrating and/or accumulating current counts corresponding to current flowing through analyte sensor 530 during fourth delay state 1224. Counter 1434 receives clock signal 1432 and continuously increments until a configurable absolute value, defined by parameter register 1436, is reached. Upon reaching the configurable absolute value, counter 1434 or another portion of state machine 1430 generates state change signal 1438, which triggers a change to fifth delay state 1228 and a reset of counter 1434.

At the onset of fifth delay state 1228, one of the first potential 1340 (e.g., 0V in "storage" mode, 0.60V in "run" mode), 0V, or an open-circuit voltage (e.g., a high impedance state) is applied to the working electrode of analyte sensor 530 and maintained for the duration of fifth delay state 1228. During at least the falling edge 1346 of second potential 1342, a current flowing through analyte sensor 530 may be substantially dominated by the RC characteristics of analyte sensor 530, which will substantially dampen out during fifth delay state 1228. INT_enable signal 1330 is low during fifth delay state 1228, so the ADC of sensor measurement circuitry 525 is not integrating and/or accumulating current counts corresponding to current flowing through analyte sensor 530 during fifth delay state 1228. Counter 1434 receives clock signal 1432 and continuously increments until a configurable absolute value, defined by parameter register 1436, is reached. Upon reaching the configurable absolute value, counter 1434 or another portion of state machine 1430 generates state change signal 1438, which triggers a change back to first delay state 1206 and a reset of counter 1434.

In some embodiments, (e.g., for determining an average impedance of analyte sensor 530 during a "run" mode in which analyte sensor 530 is already inserted in the skin of the host), state machine 1430 can be configured to cycle through the above-described states (or a subset thereof) a predetermined number of times (e.g., 125) over a predetermined interval of time (e.g., 10-12 seconds) before MUX 1416 is configured to pass an accumulated current count value from accumulator 1414 to sample buffer 1420 and/or to threshold detection module 1422 for determination of whether controller wakeup signal 1424 is to be generated to wakeup controller 535. In some such embodiments, accumulator 1414 is configured to integrate the differential current count samples passed by MUX 1412 (e.g., accumulator 1414 adds each subsequent differential current count sample to a running sum of differential current count samples previously passed by MUX 1412 during the integration period).

Once state machine 1430 has cycled through the above-described states (or an enabled subset thereof) the predetermined number of times, and accumulator 1414 has summed the differential current count samples generated during the predetermined number of cycles, accumulator 1414 is configured to pass the summed differential current count value to MUX 1416 and, based on Sum Enable signal 1418 being set to high, MUX 1416 is configured to pass that summed differential current count value to sample buffer 1420, which stores the summed differential current count value.

In some such embodiments, threshold detection module 1422 can be configured to generate controller wakeup signal 1424 responsive to MUX 1416 passing the summed differential current count value to sample buffer 1420 and, in some cases also to threshold detection module 1422. In such embodiments, a configurable threshold for generating controller wakeup signal 1424 would be receipt and/or storage of one summed differential current count value by sample buffer 1420. Responsive to controller wakeup signal 1424, controller 535 can be configured to wakeup and further process the summed differential current count value stored in sample buffer 1420 (e.g., dividing the summed differential current count value by a number "N" of differential current counts, thereby calculating an average current count value that can be utilized to calculate an average impedance of analyte sensor 530 according to any appropriate or known processing algorithm, e.g., Ohm's Law, etc.). Accordingly, the battery can be further conserved, even during a run mode, by sleeping controller 535 while state machine 1430 determines one or more current counts and saves one or more of them in sample buffer 1420.

In some other embodiments, (e.g., for determining an impedance of analyte sensor 530 during a "storage" mode in which analyte sensor 530 is not yet inserted in the skin of the host), state machine 1430 can be configured such that, for each cycle through the above-described states (or an enabled subset thereof), MUX 1412 passes the differential current count sample, generated by differentiator 1406 during pulse count sampling state 1220 as described above, directly to MUX 1416. MUX 1416, responsive to Sum Enable signal 1418 being low, can pass each of the differential current count samples to sample buffer 1420, which stores the differential current count samples. In such embodiments, accumulator 1414 may not integrate multiple differential current count samples from differentiator 1406 and may be effectively bypassed.

Moreover, in some such storage mode embodiments, threshold detection module 1422 can be configured to generate controller wakeup signal 1424 responsive to a predetermined and/or calibrated number "N" of the differential current count samples stored in sample buffer 1420 consecutively or non-consecutively satisfying (e.g., being any one of greater than, less than or equal to) a predetermined threshold value (e.g., 0x7FF in hexadecimal notation) or a range of predetermined threshold values (e.g., within a range of 0x700 and 0x7FF in hexadecimal notation). Responsive to controller wakeup signal 1424, controller 535 can be configured to wakeup and further process one or more of the differential current count values stored in sample buffer 1420 (e.g., determining whether a false wakeup has occurred and/or calculating an average impedance of analyte sensor 530 according to any appropriate or known processing algorithm, e.g., Ohm's Law). In the event that a wakeup responsive to generation of controller wakeup signal 1424 is subsequently determined to be a false wakeup, controller 535 may cause analyte sensor system 308 to re-enter "storage" mode and controller 535 may then revert to the lower power mode.

In some yet other embodiments, (e.g., during actual continuous glucose monitoring), state machine 1430 can be configured such that all states except pre-count sampling state 1208 are disabled and pre-count sample buffer 1404, differentiator 1406 and accumulator 1414 are effectively bypassed and/or otherwise disabled. In such embodiments, current count samples from the ADC of the AFE are passed directly to MUX 1412. Differential mode enable signal 1410 and Sum Enable signal 1418 can both be set to low. Accordingly, responsive to differential mode enable signal 1410 being low, MUX 1412 directly passes the current count samples to MUX 1416 and, responsive to Sum Enable signal 1418 being low, MUX 1416 directly passes the current count samples to sample buffer 1420, which stores each of the current count samples.

Moreover, in some such embodiments, threshold detection module 1422 can be configured to generate controller wakeup signal 1424 responsive to a predetermined number "N" of the current count samples being stored in sample buffer 1420. Responsive to controller wakeup signal 1424, controller 535 can be configured to wakeup and further process one or more of the current count values stored in sample buffer 1420 (e.g., calculating an analyte concentration value based at least in part on the current count values according to any appropriate or known processing algorithm).

In addition, the present disclosure also contemplates the disablement of one or more of states 1206, 1208, 1212, 1216, 1220, 1224, 1228 as previously described in connection with FIG. 12. For example, in some embodiments, fifth delay state 1228, which may also be considered an "extended idle" state, may only be enabled when analyte sensor system 308 is in an above-described "storage" mode in which analyte sensor 530 is not yet disposed in a skin of the host. Such an "extended idle" state may be utilized to keep a voltage bias across the terminals of analyte sensor 530 at 0V or open-circuit to avoid oxidation and/or other sensor damage that would otherwise be caused by a defined, non-zero voltage bias being applied across the terminals of analyte sensor 530.

In some embodiments, one or both of second delay state 1212 and fourth delay state 1224 may be disabled. For example, one purpose of delays 1206, 1212, 1216, 1224 is to suspend current count measuring, sensing and/or accumulating by the ADC of the AFE during time intervals immediately following a change in voltage bias applied to the working electrode of analyte sensor 530. Because the working electrode potential is held constant for the duration of each of pre-count sample state 1208 and pulse count state 1220, second delay state 1212 and fourth delay state 1224 may be superfluous in some such implementations.

In some embodiments where the working electrode potential is held at the same potential, e.g., 0V, in each of pre-count sampling state 1208 and enabled fifth delay state 1228, first delay state 1206 may be disabled if it would otherwise directly follow fifth delay state 1228 (e.g., all instances of first delay state 1206 except a first instance during a session), since there would be no change in voltage potential at the transition from fifth delay state 1228 directly to pre-count sampling state 1208.

In some embodiments where the working electrode potential is held at the same potential, e.g., 0.6V while taking continuous analyte concentration measurements during an above-described "run" mode, all states except pre-count sampling state 1208 can be disabled, since pulse count sampling state 1220 is not enabled and there would be no change in voltage potential applied to the working electrode of analyte sensor 530 where no transitions from one state to any other state occur. Moreover, where pulse count sampling state 1220 is disabled, differential mode enable signal 1410 may be forced to the low, disabling state, since without pulse count sampling state 1220, differential current count samples are not generated or utilized.

Figure 15:
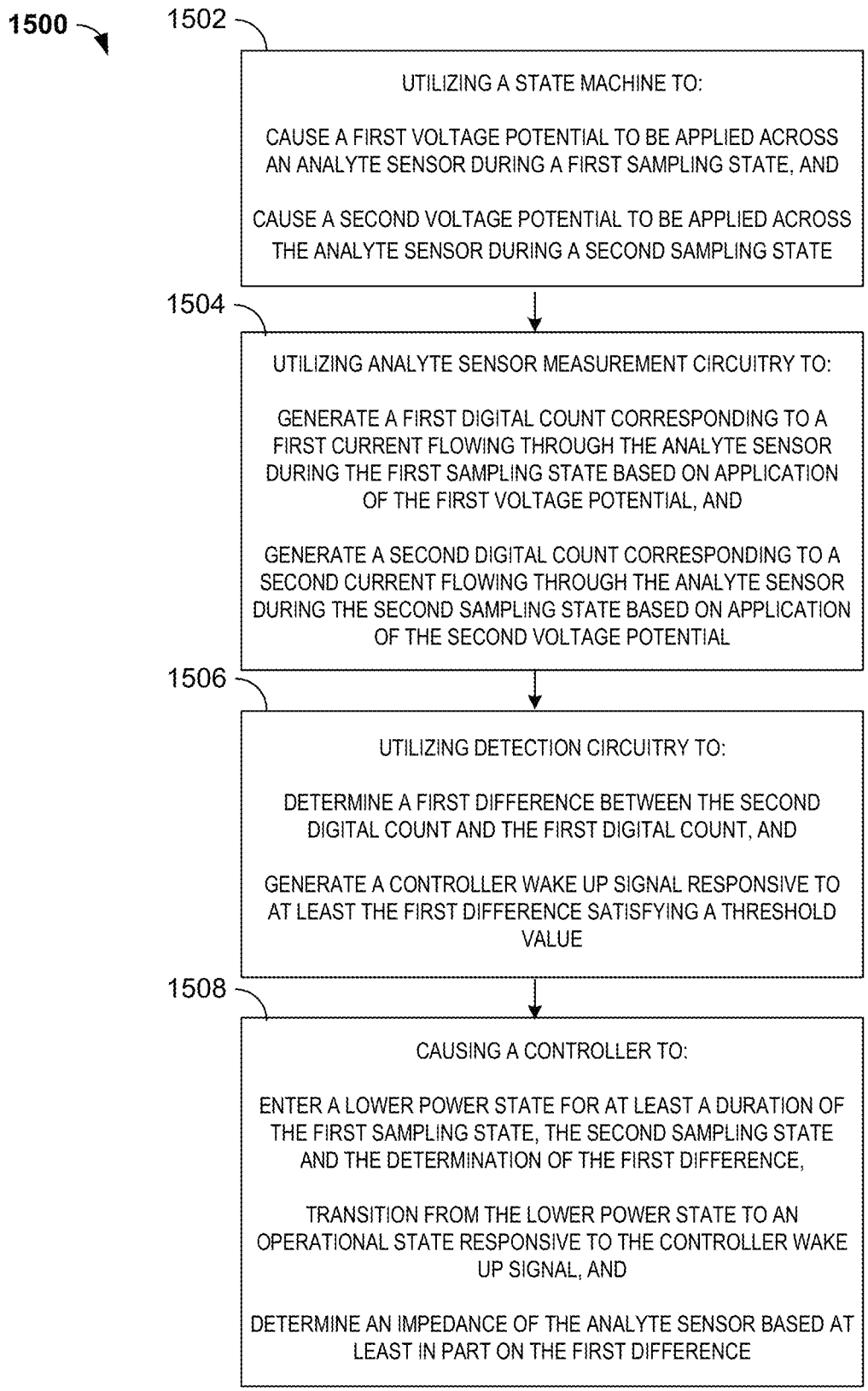
FIG. 15 illustrates a flowchart for a method of controlling an analyte sensor system, in accordance with some embodiments.

An example method 1500 for controlling an analyte sensor system is provided below in connection with FIG. 15. Method 1500 comprises one or more steps or actions, which may be interchanged with one another without departing from the scope of the claims. In other words, unless a specific order of steps or actions is specified, the order and/or use of specific steps and/or actions may be modified without departing from the scope of the claims. Method 1500 may correspond at least to the previous description in connection with FIGS. 12-14.

Block 1502 includes utilizing a state machine to cause a first voltage potential to be applied across an analyte sensor during a first sampling state and cause a second voltage potential to be applied across the analyte sensor during a second sampling state. For example, as previously described in connection with at least FIGS. 12-14, state machine 1430 can be configured to cause first voltage potential 1340 to be applied across analyte sensor 530 during first sampling state 1208 and cause a second voltage potential 1342 to be applied across analyte sensor 530 during second sampling state 1220. As previously described in connection with at least FIGS. 13 and 14, in a first operating mode (e.g., a "storage" mode during which analyte sensor 530 is not yet inserted into the skin of the host), first voltage potential 1340 can be zero volts and second voltage potential 1342 is greater than first voltage potential 1340 by a predetermined amount (e.g., 16 mV). In a second operating mode (e.g., a "run" mode during which analyte sensor 530 is inserted into the skin of the host), first voltage potential 1340 can be the same as the voltage potential applied across analyte sensor 530 to determine analyte concentrations within the host (e.g., 0.6V) and second voltage potential 1432 (e.g., 0.616V) is greater than first voltage potential 1430 by the predetermined amount (e.g., 16 mV).

Block 1504 includes utilizing analyte sensor measurement circuitry to generate a first digital count corresponding to a first current flowing through the analyte sensor during the first sampling state based on application of the first voltage potential and generate a second digital count corresponding to a second current flowing through the analyte sensor during the second sampling state based on application of the second voltage potential. For example, analyte sensor measurement circuitry 525 can be configured to generate a first digital count 1402 corresponding to a first current flowing through analyte sensor 530 during first sampling state 1208 based on application of first voltage potential 1340 and generate a second digital count 1402 corresponding to a second current flowing through analyte sensor 530 during second sampling state 1220 based on application of second voltage potential 1342 as previously described in connection with at least FIGS. 13 and 14.

Block 1506 includes utilizing detection circuitry to determine a first difference between the second digital count and the first digital count and generate a controller wake up signal responsive to at least the first difference satisfying a threshold value or a range of threshold values. For example, differentiator 1406 can be configured to determine a first difference between the first and second digital counts 1402 and threshold detection module 1422 can be configured to generate controller wake up signal 1424 responsive to at least the first difference satisfying a threshold value as previously described in connection with at least FIGS. 13 and 14.

Block 1508 includes causing a controller to enter a lower power state for at least a duration of the first sampling state, the second sampling state and the determination of the first difference, transition from the lower power state to an operational state responsive to the controller wake up signal and determine an impedance of the analyte sensor based at least in part on the first difference. For example, as previously described in connection with at least FIGS. 12-14, controller 535 can be configured to enter a lower power state (e.g., a sleep state) while state machine 1430 cycles through those of states 1206, 1208, 1212, 1216, 1220, 1224, 1228 that are enabled. Controller 535 can further be configured to transition from this lower power state to an operational state responsive to controller wake up signal 1424. Once woken, controller 535 can determine an impedance of analyte sensor 530 based at least in part on the difference between a first digital current count 1402 corresponding to the current flowing through analyte sensor 530 while first voltage potential 1340 is being applied across analyte sensor 530 during first sampling state 1208 and a second digital current count 1402 corresponding to the current flowing through analyte sensor 530 while second voltage potential 1342 is being applied across analyte sensor 530 during second sampling state 1220. For example, one or more counts stored in sample buffer 1420 (see, e.g., FIG. 14) are utilized by controller 535, upon wake up, to make such a determination of the impedance of analyte sensor 530

In some embodiments, method 1500 may further comprise initiating application of first voltage potential 1340 across analyte sensor 530 during delay state 1206, which immediately precedes first sample state 1208 and suspending generation of digital counts 1402 by analyte sensor measurement circuitry 525 during delay state 1206, as previously described in connection with at least FIGS. 13 and 14.

In some embodiments, method 1500 may further comprise initiating application of second voltage potential 1342 across analyte sensor 530 during delay state 1216, which immediately precedes second sample state 1220 and suspending generation of digital counts 1402 by analyte sensor measurement circuitry 525 during delay state 1220, as previously described in connection with at least FIGS. 13 and 14.

In some embodiments, method 1500 may further comprise utilizing state machine 1430 to cause a zero-voltage potential (e.g., first voltage potential 1340 or an open-circuit voltage) to be applied across analyte sensor 530 during delay state 1228, which follows second sample state 1220 and suspending generation of digital counts 1402 by analyte sensor measurement circuitry 525 during delay state 1228, as previously described in connection with at least FIGS. 13 and 14.

In some embodiments, method 1500 may further comprise storing the first digital count 1402 in pre-count sample buffer 1404 prior to the differentiator 1406 determining the difference between the digital current count 1402 received from the ADC during first sampling state 1208 and the digital current count 1402 received from the ADC during second sampling state 1220, as previously described in connection with at least FIGS. 13 and 14.

In some embodiments, method 1500 may further comprise receiving, by differentiator 1406, the first digital count 1402 from pre-count sample buffer 1404, receiving, by differentiator 1406, the second digital count 1402 from the ADC, and utilizing differentiator 1406 to determine the difference between those digital current counts, as previously described in connection with at least FIGS. 13 and 14.

In some embodiments, method 1500 may further comprise utilizing accumulator 1414 to generate a sum of the first difference and at least a second difference between a third digital count 1402 and a fourth digital count 1402, wherein the third digital count corresponds to a third current flowing through analyte sensor 530 during a subsequent instance of first sampling state 1208 and wherein the fourth digital count corresponds to a fourth current flowing through analyte sensor 530 during a subsequent instance of second sampling state 1220, as previously described in connection with at least FIGS. 13 and 14.

In some embodiments, method 1500 may further comprise generating controller wake up signal 1424 responsive to at least the sum of the first difference and the second difference satisfying the threshold value, as previously described in connection with at least FIGS. 13 and 14.

In some embodiments, method 1500 may further comprise utilizing controller 535 to define at least one parameter of state machine 1430 (e.g., as stored in parameter register 1436) before entering the lower power state.

Combinations of Activation Detection Techniques

In some embodiments, for a robust wake-up procedure and to avoid false wakeups, multiple indicators of analyte sensor 530 implantation can be used to determine that analyte sensor system 308 should exit the lower power state. Care should generally be taken, however, to avoid damaging or changing the performance properties of analyte sensor system 308, to maintain robustness against humidity events that may trigger activation prior to implantation of analyte sensor 530, and to maintain relatively lower power operation, which can be important for battery-operated devices.

In embodiments, the primary and secondary signals from analyte sensor 530 may be used for triggering activation of analyte sensor system 308. For example, a secondary signal generated using analyte sensor 530, such as impedance, may be monitored and compared to a threshold or other condition. If the secondary signal meets or satisfies the threshold or other condition, then analyte sensor 530 may be caused to gather information related to a level of an analyte in a host. If the level of the analyte in the host meets a second threshold or condition, then analyte sensor system 308 can be caused to exit the lower power state. In embodiments in which the potentiostat is always on, such that analyte sensor 530 is continuously or regularly caused to gather information related to the level of the analyte in the host, the secondary signal can be monitored for purposes of activating other circuits and subsystems of analyte sensor system 308.

In embodiments, the primary signal from analyte sensor 530 (which, as described above, relates to or can be used to calculate a level of an analyte in the user) may be used in combination with a secondary signal obtained using analyte sensor 530 and/or a signal from a sensor or other component that may be included in or used in conjunction with activation detection circuit 520 and/or activation detection component 545, in order to control activation of analyte sensor system 308 and reduce false wakeups. In embodiments, the primary and secondary signals from analyte sensor 530 and/or the secondary signals from a sensor or other component that may be included in or used in conjunction with activation detection circuit 520 and/or activation detection component 545 may be used for activation purposes, where such analyte sensor 530 and other signals are monitored at more than one time period (e.g., at the various discrete phases where detectable events may typically occur, from before implantation of analyte sensor 530, implantation, and beyond implantation). Various of these signals can be measured/characterized at different times in order to provide a more robust activation scheme.

Referring further to FIG. 5 (by way of example), in embodiments, a secondary signal from activation detection component 545 may be indicative of analyte sensor system 308 being removed from its product packaging, or otherwise indicative of a determination that implantation of analyte sensor 530 and/or deployment of analyte sensor system 308 is likely to occur in the near future, and a secondary signal from analyte sensor 530 may be indicative of implantation occurring. For example, a secondary signal from an accelerometer or other component/switch used for activation purposes (e.g., as described herein) can be monitored, and when the secondary signal indicates that analyte sensor system 308 has been removed from product packaging therefor, or that implantation of analyte sensor 530 has occurred or is likely to occur in the near future, analyte sensor 530 may be used to generate a primary signal related to the level of analyte in a host. For example, a primary signal related to the level of analyte in a host may be used to determine whether implantation of analyte sensor 530 has occurred. If the primary signal related to the level of the analyte in the host meets a threshold or condition, then analyte sensor system 308 can be caused to exit the lower power state. In embodiments, a secondary signal from an accelerometer can be monitored and another secondary signal may be monitored by a temperature sensor, conductivity sensor, capacitive sensor, inductance sensor, voltage sensor, impedance sensor, or any other sensor capable of determining an electrical, physical, magnetic, or chemical property indicative of implantation of analyte sensor 530 into a host.

In embodiments, activation detection circuit 520 may monitor for a secondary signal generated by a bridge-based switch/sensor, a pull tab switch/sensor, an audio sensor, a proximity sensor, an RFID sensor, a magnetic field based switch/sensor, or any other switch/sensor/technique, including those discussed herein, where such switches/sensors/components are capable of determining that analyte sensor system 308 has been removed from product packaging and/or an applicator, or that implantation of analyte sensor 530 has occurred or is likely to occur in the near future. For example, a secondary signal may be generated by electrical contacts of a bridge-based switch/sensor being disconnected or connected (e.g., as describe above in connection with FIG. 6C), which may indicate that analyte sensor system 308 has been removed from product packaging and/or an applicator. In embodiments, a pull tab-based switch/sensor may be used to cause analyte sensor system 308 to generate a secondary signal for activation purposes. For example, and as discussed herein, a non-conductive material may be placed between spring-loaded electrical contacts. In response to the nonconductive material between the spring-loaded electrical contacts being removed (with or without direct user intervention), the spring-loaded electrical contacts may be caused to form a physical/electrical connection that may electrically couple the contacts to one another. A secondary signal may indicate that the spring-loaded electrical contacts have been connected to one another, thus initializing the wakeup.

In embodiments, a proximity sensor may generate a secondary signal if the proximity sensor determines that analyte sensor system 308 has been removed to a threshold distance from product packaging and/or an applicator. In embodiments, an audio sensor may generate a secondary signal if an audio signature is recognized (e.g., by employing transducers and other audio components), where the audio signature may indicate that analyte sensor system 308 has been removed from product packaging and/or applicator, or that implantation of analyte sensor 530 has occurred or is likely to occur in the near future. Similarly, a secondary signal may be generated using an RFID sensor, magnetic field sensor, or any other sensor capable of determining that analyte sensor system 308 has been removed from product packaging and/or an applicator, or that implantation of analyte sensor 530 has occurred or is likely to occur in the near future.

In embodiments, after a secondary signal is detected using one or more of activation detection component 545 and activation detection circuit 520, where the secondary signal may be indicative of analyte sensor system 308 being removed from product packaging and/or an applicator, a primary signal may be generated using analyte sensor 530, where the primary signal relates to a level of an analyte in a host. Using the level of the analyte in the host and a threshold value or other condition/characteristic that may be indicative of analyte sensor 530 implantation, it may be determined whether or not implantation of analyte sensor 530 has likely occurred.

For example, a secondary signal may be generated using a temperature or pressure sensor. If the secondary signal generated by the temperature/pressure sensor meets a threshold value or condition, then analyte sensor system 308 may triggered to exit a lower power state. In this example, the threshold condition may be a temperature related to the average body temperature of a host such that analyte sensor system 308 may be caused to check whether the lower power state should be exited based upon the measured temperature or temperature gradient. In embodiments, a secondary signal may be generated using a capacitance sensor or measurement, where the threshold condition may be related to the expected measured capacitance associated with analyte sensor 530 following implantation into a host. In embodiments, a secondary signal may be generated using a voltage sensor or measurement, where the threshold condition may be related to an expected voltage across one or more electrodes of analyte sensor 530 following implantation into a host. A secondary signal may be generated using any an electrical, physical, magnetic, or chemical sensor capable of measuring a property indicative of implantation of analyte sensor system 308 into a host.

In embodiments, primary and/or one or more secondary signals may be used for causing analyte sensor system 308 to exit the lower power state. Using primary and/or one or more secondary signals may increase the robustness of the activation scheme for analyte sensor system 308 by reducing the occurrence of false wakeups. In embodiments, monitoring a primary signal may be conditioned upon analyte sensor system 308 detecting two secondary signals that indicate that analyte sensor system 308 has been removed from product packaging and/or an applicator, or that implantation of analyte sensor 530 has occurred or is likely to occur in the near future. For example, monitoring a primary signal may be conditioned on a secondary signal generated using an accelerometer and a secondary signal generated using a bridge-based switch/sensor both satisfying certain conditions. After both secondary signals are determined to satisfy respective conditions associated with likely implantation of analyte sensor 530 or deployment of analyte sensor system 308, analyte sensor 530 may then monitor for a primary signal (e.g., relating to an analyte level) to determine that implantation of analyte sensor 530 has occurred.

In embodiments, any number of secondary signals may be monitored using any combination of the various techniques described herein and monitoring the primary signal may be conditioned upon the secondary signals satisfying respective conditions. In embodiments, the secondary signals may be monitored simultaneously or in a staged fashion, where subsequent secondary signals are only monitored in response to certain secondary signals meeting conditions associated therewith. For example, secondary signals may be obtained at any time by any secondary switch/sensor/component scheme/technique discussed herein using activation detection circuit 520 and/or activation detection component 545.

In embodiments, as alluded to above, the secondary signals may be monitored in a particular order or sequence. For example, activation detection circuit 520 may initially obtain the secondary signal generated using a bridge-based switch/sensor and a determination may be made as to whether this secondary signal indicates that analyte sensor system 308 has been removed from product packaging and/or an applicator. Thereafter, if this bridge-derived secondary signal so indicates, activation detection circuit 520 may obtain a secondary signal generated using an accelerometer, and a determination may be made as to whether movement of analyte sensor system 308 is consistent with that of typical human handling or gait, as discussed herein, or is otherwise characteristic of analyte sensor system 308 being deployed. If so, the primary signal that is generated using analyte sensor 530 can then be obtained and checked for purposes of activating analyte sensor system 308 or causing the same to exit a lower power state.

Similarly, other combinations of signals may be used to cause for analyte sensor system 308 to exit the lower power state. For example, if a secondary signal related to temperature meets a threshold or condition, then analyte sensor system 308 may be caused to determine whether the level of analyte in the host that can be measured using analyte sensor 530 satisfies a threshold value or condition. In embodiments, two or more secondary signals from any of the switches/sensor/component schemes described herein may be used in connection with determining whether analyte sensor system 308 should be caused to exit the lower power state. In embodiments, the secondary signals may be monitored simultaneously or they may be monitored in a particular or staged order.

Figure 10:
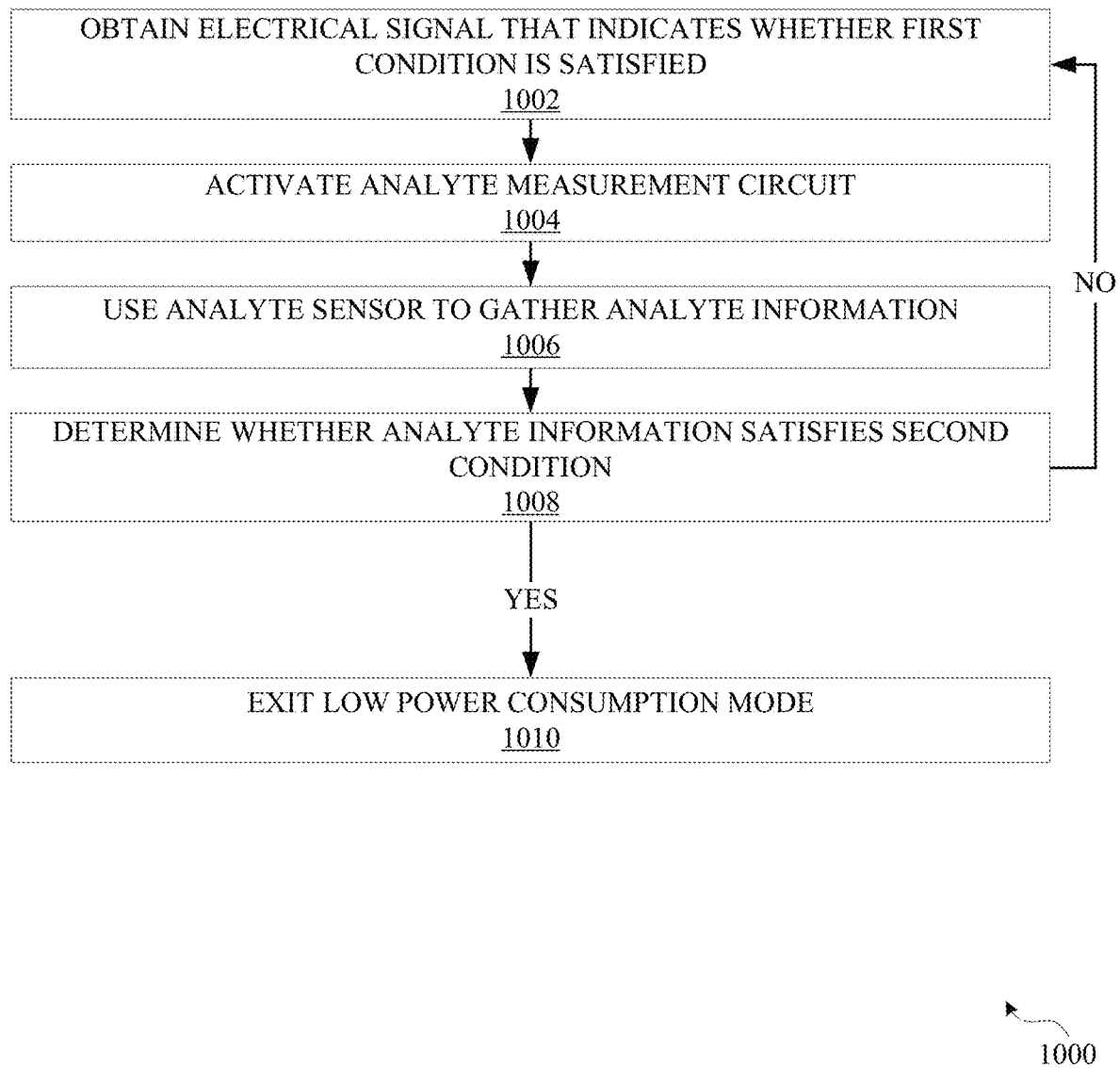
FIG. 10 is an operational flow diagram illustrating various operations that may be performed, in accordance with some embodiments.

FIG. 10 is an operational flow diagram illustrating various example operations of method 1000 that may be performed in accordance with embodiments of the disclosure. In embodiments, method 1000 may be used for determining whether a first condition and a second condition are satisfied before activating analyte sensor system 308 or causing the same to exit a lower power mode. Operation 1002 involves obtaining an electrical signal using activation detection circuit 520 and/or activation detection component 545 (referring to FIG. 5, for example). The electrical signal may indicate whether the first condition is satisfied. For example, the first condition being satisfied may depend on whether a first sensor characteristic from a switch/sensor (e.g., such as an accelerometer, temperature sensor, or any of the other techniques that may be implemented using one or more of activation detection circuit 520 and activation detection component 545) is detected and/or a threshold condition is met. The electrical signal may be generated using one or more sensors if the first sensor characteristic is detected and/or the threshold condition is met.

As described above, the electrical signal may be generated using one or more of a detected proximity between analyte sensor system 308 and a reference object (e.g., an applicator or packaging for analyte sensor system 308); a temperature; an output of an accelerometer; a response generated using wireless signaling transmitted or received by analyte sensor system 308; a detected change in air pressure; audio information; a signal generated by analyte sensor system 308 in response to detecting photons; a conductivity, voltage, impedance, resistance, or capacitance, e.g., as measured between two or more terminals of analyte sensor system 308 and/or analyte sensor 530; a mechanical or electromechanical switch located on or within a housing of analyte sensor system 308 or the packaging or applicator thereof; the detection of magnetic field; a measured strain; or another detectable event/condition as described herein.

At operation 1004, method 1000 may include activating analyte measurement device 810 (such as, for example, a potentiostat etc.) in response to analyte sensor system 308 obtaining or generating the electrical signal. For example, a bias voltage may also be applied across first and second terminals 828 and 830 of analyte sensor 808 of circuit 800 (referencing FIG. 8A by way of example) in response to analyte sensor system 308 obtaining the electrical signal. At operation 1006, method 1000 may include using analyte sensor 808 to gather analyte information from the host. For example, measurement device 810 may be used in conjunction with analyte sensor 808 to measure a primary signal that may be indicative of a level of an analyte in a host.

At operation 1008, method 1000 may include determining whether the primary signal (e.g., related to analyte information) satisfies a second condition or characteristic. For example, the primary signal may satisfy a second condition if the primary signal meets a predetermined threshold or other characteristic (e.g., value, gradient, count condition, etc.). The second condition or characteristic may be satisfied if the primary signal remains constant above a threshold or changes, over a certain time period. At operation 1010, if the primary signal satisfies the second condition, method 1000 may include analyte sensor system 308 exiting the lower power consumption mode.

By way of example, if the first condition is satisfied at operation 1002, and the second condition is satisfied at operation 1008, circuit 800 may then be used to generate output 836 that can cause activation of analyte sensor system 308 into a working or operating mode (or for example, a triggered state, referencing embodiments in connection with FIG. 9). In the working mode or the like, circuit 800 may continue to be used to gather analyte information, and such information may be stored in storage 515 and/or transmitted using TRX 510 (again, referencing FIG. 5 by way of example). If, however, it is determined at operation 1008 that the analyte information does not satisfy the second condition, method 1000 may return to operation 1002, and analyte sensor system 308 may remain in a lower power consumption mode (or for example, a non-triggered state, referencing embodiments in connection with FIG. 9). In example embodiments, the electrical signal may be obtained and/or monitored/checked at operation 1002 according to a frequency/time period/interval that is predetermined, programmable, adaptable, variable, and/or configurable or the like.

ADDITIONAL EMBODIMENTS

One of skill in the art will appreciate upon studying the present disclosure that various additional embodiments not described explicitly herein are within the spirit and scope of the present disclosure.

Figure 11:
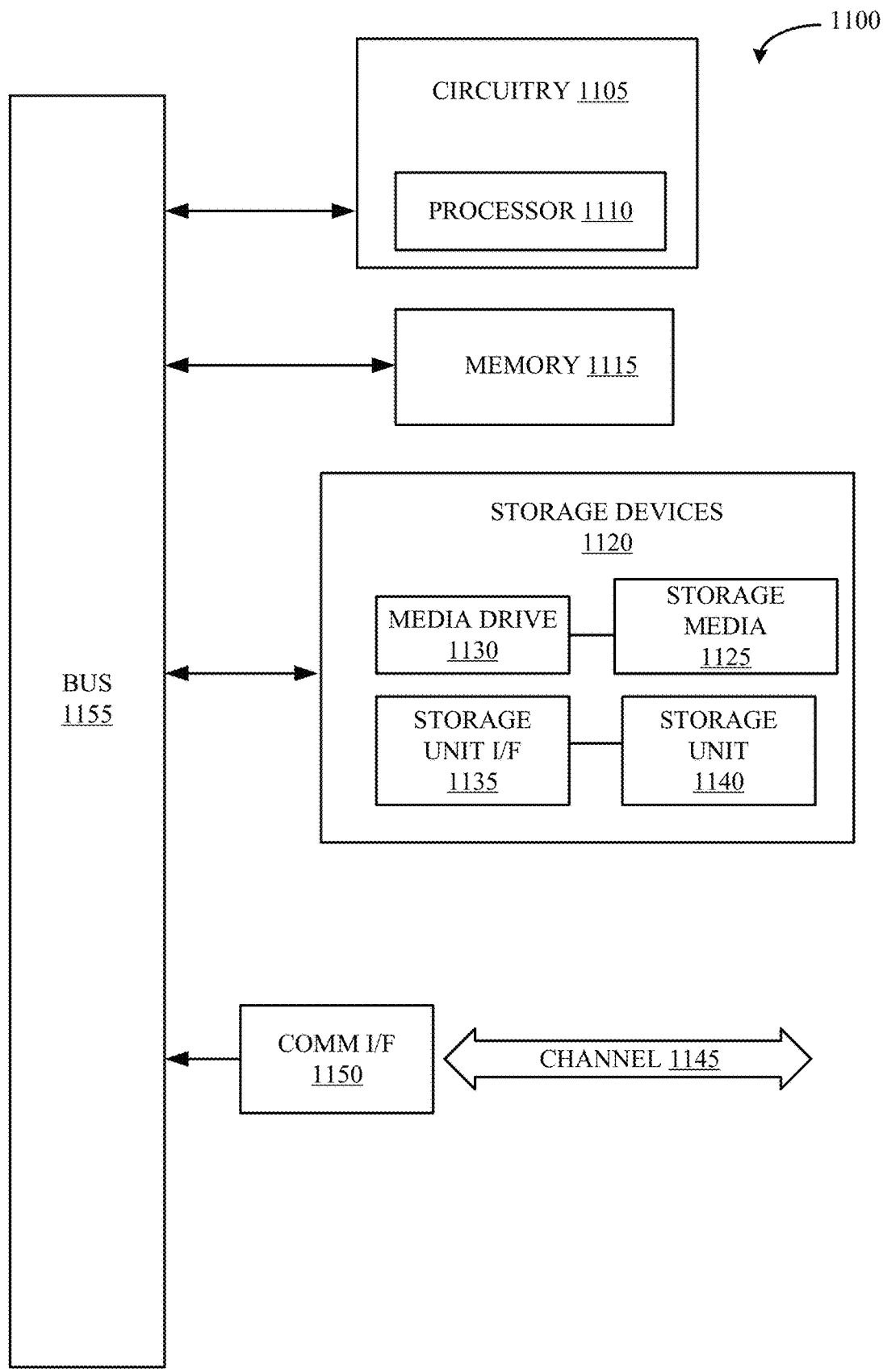
FIG. 11 illustrates an example computing module, in accordance with some embodiments.

FIG. 11 illustrates example computing module 1100, which may in some instances include a processor/microprocessor/controller resident on a computer system (e.g., in connection with server system 334, any of the display devices described herein (e.g., display devices 120, 130, 140, 310 (*a, b*, etc.), partner devices 315 (*a, b*, etc.), and/or analyte sensor system 8, 308, etc. Computing module 1100 may be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, including embodiments of analyte sensor system 308, display device 310, partner devices 315, server system 334, and components of or used in connection with the foregoing as described and/or contemplated herein, etc., one of skill in the art will appreciate upon studying the present disclosure the additional variations and details regarding the functionality of these embodiments that may be carried out by computing module 1100. In this connection, it will also be appreciated by one of skill in the art upon studying the present disclosure that features and aspects of the various embodiments (e.g., systems, devices, and/or apparatuses, and the like) described herein may be implemented with respected to other embodiments (e.g., methods, processes, and/or operations, and the like) described herein without departing from the scope or spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In example implementations, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 11. Various embodiments are described in terms of example computing module 1100. After reading this description, it will become apparent to a person skilled in the relevant art how to implement the application using other computing modules or architectures.

Referring now to FIG. 11, computing module 1100 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 1100 is specifically purposed.

Computing module 1100 may include, for example, one or more processors, microprocessors, controllers, control modules, or other processing devices, such as a processor 1110, and such as may be included in circuitry 1105. Processor 1110 may be implemented using a special-purpose processing engine such as, for example, a microprocessor, controller, or other control logic. In the illustrated example, processor 1110 is connected to bus 1155 by way of circuitry 1105, although any communication medium may be used to facilitate interaction with other components of computing module 1100 or to communicate externally.

Computing module 1100 may also include one or more memory modules, simply referred to herein as main memory 1115. For example, random access memory (RAM) or other dynamic memory may be used for storing information and instructions to be executed by processor 1110 or circuitry 1105. Main memory 1115 may also be used for storing temporary variables or other intermediate information during execution of instructions to be executed by processor 1110 or circuitry 1105. Computing module 1100 may likewise include a read only memory (ROM) or other static storage device coupled to bus 1155 for storing static information and instructions for processor 1110 or circuitry 1105.

Computing module 1100 may also include one or more various forms of information storage devices 1120, which may include, for example, media drive 1130 and storage unit interface 1135. Media drive 1130 may include a drive or other mechanism to support fixed or removable storage media 1125. For example, a hard disk drive, a floppy disk drive, a magnetic tape drive, an optical disk drive, a CD or DVD drive (R or RW), or other removable or fixed media drive may be provided. Accordingly, removable storage media 1125 may include, for example, a hard disk, a floppy disk, magnetic tape, cartridge, optical disk, a CD or DVD, or other fixed or removable medium that is read by, written to or accessed by media drive 1130. As these examples illustrate, removable storage media 1125 may include a computer usable storage medium having stored therein computer software or data.

In alternative embodiments, information storage devices 1120 may include other similar instrumentalities for allowing computer programs or other instructions or data to be loaded into computing module 1100. Such instrumentalities may include, for example, fixed or removable storage unit 1140 and storage unit interface 1135. Examples of such removable storage units 1140 and storage unit interfaces 1135 may include a program cartridge and cartridge interface, a removable memory (for example, a flash memory or other removable memory module) and memory slot, a PCMCIA slot and card, and other fixed or removable storage units 1140 and storage unit interfaces 1135 that allow software and data to be transferred from removable storage unit 1140 to computing module 1100.

Computing module 1100 may also include a communications interface 1150. Communications interface 1150 may be used to allow software and data to be transferred between computing module 1100 and external devices. Examples of communications interface 1150 include a modem or soft-modem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 1150 may in examples be carried on signals, which may be electronic, electromagnetic (which includes optical) or other signals capable of being exchanged by a given communications interface 1150. These signals may be provided to/from communications interface 1150 via channel 1145. Channel 1145 may carry signals and may be implemented using a wired or wireless communication medium. Some non-limiting examples of channel 1145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including, for example, when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; the term "set" should be read to include one or more objects of the type included in the set; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A system for controlling activation of analyte sensor electronics circuitry, the system comprising:
    an analyte sensor that is electrically and mechanically coupled to the analyte sensor electronics circuitry prior to transitioning the system into an operational state;
    wherein the analyte sensor electronics circuitry is adapted to:
        trigger an indication for the system to exit a lower power state and transition into the operational state, wherein the indication is a non-analyte signal that is triggered based on a first threshold value associated with an indication of insertion of the analyte sensor into a host;
        responsive to the indication, generate a control signal operable to cause the analyte sensor to gather information related to a level of an analyte in the host; and
        generate a comparison between the information related to the level of the analyte in the host and a condition, wherein the condition comprises the level of the analyte in the host exceeding a second threshold value;
    wherein the system exits the lower power state and transitions into the operational state based on the indication being triggered and the comparison indicating that the level of the analyte in the host satisfies the condition.

2. The system of claim 1, wherein the analyte sensor electronics circuitry is further adapted to cause the system to trigger the indication in response to the first threshold value being satisfied for at least a predetermined amount of time.

3. The system of claim 1, wherein the non-analyte signal is generated using one or more of an activation detection circuit and an activation detection component that are adapted to detect one or more of the insertion of the analyte sensor into the host and deployment of the system.

4. The system of claim 1, wherein the control signal is a signal operable to cause a potentiostat to apply a voltage bias to the analyte sensor and thereby cause the analyte sensor to gather the information related to the level of the analyte in the host.

5. The system of claim 1, wherein, after the system transitions to the operational state, the system is configured to continue to gather the information related to the level of the analyte in the host and is configured to communicate the information to one or more display devices or one or more partner devices.

6. The system of claim 1, wherein the second threshold value is related to a level of a known analyte typically present in a human host.

7. The system of claim 1, wherein the indication is generated using one or more of:
    a detected proximity between the analyte sensor electronics circuitry and a reference object;
    a temperature monitored using the analyte sensor electronics circuitry;
    an output of an accelerometer of the analyte sensor electronics circuitry;
    a response generated using wireless signaling transmitted or received by the analyte sensor electronics circuitry;
    a detected change in air pressure measured by the analyte sensor electronics circuitry;
    audio information monitored by the analyte sensor electronics circuitry;
    a signal generated by the analyte sensor electronics circuitry in response to photons detected by the analyte sensor electronics circuitry;
    a conductivity measured between two terminals of the analyte sensor electronics circuitry;
    a mechanical switch located on or within a housing of the analyte sensor electronics circuitry;
    a component adapted to change a connection between two conductive elements of the analyte sensor electronics circuitry, in response to movement of the component; and
    a measured strain.

8. The system of claim 1, wherein the condition comprises the level of the analyte in the host exceeding the second threshold value for programmed intervals of time.

9. The system of claim 1, wherein the analyte sensor electronics circuitry is adapted such that the information related to the level of the analyte in the host is used to generate detected counts, wherein the condition further comprises a threshold characteristic, and wherein if the comparison indicates that the detected counts meet the threshold characteristic, the system is configured to exit the lower power state and enters the operational state.

10. A method for controlling analyte sensor electronics circuitry, the method comprising:
    the analyte sensor electronics circuitry obtaining a first electrical signal generated using one or more of an analyte sensor and a secondary sensor;
    determining whether a first condition is met based on the first electrical signal obtained by the analyte sensor electronics circuitry, wherein the first electrical signal is a non-analyte signal that is generated in response to insertion of the analyte sensor into a host;
    responsive to the first condition being met, the analyte sensor electronics circuitry activating an analyte measurement circuit;
    the analyte measurement circuit using the analyte sensor to gather information related to an analyte value in the host, wherein the analyte sensor was coupled to the analyte sensor electronics circuitry before the analyte sensor was implanted into the host;
the analyte sensor electronics circuitry determining whether the information related to the analyte value in the host meets a second condition, wherein the second condition is met if the information related to the analyte value indicates that a level of the analyte value in the host exceeds a threshold value;
responsive to the analyte sensor electronics circuitry determining that the information related to the analyte value in the host meets the second condition, the analyte sensor electronics circuitry exiting a lower power consumption mode; and
responsive to the analyte sensor electronics circuitry determining that the information related to the analyte value in the host does not meet the second condition, the analyte sensor electronics circuitry remaining in the lower power consumption mode and obtaining a second electrical signal that indicates whether the first condition has been met.

11. The method of claim 10, wherein the threshold value is related to a level of a known analyte typically present in a human host.

12. The method of claim 10, wherein the first condition represents a proximity of the analyte sensor electronics circuitry to a reference point.

13. The method of claim 10, wherein the first condition represents a level of acceleration detected using an accelerometer.

14. The method of claim 10, wherein the first condition relates to one or more electrical characteristics measured for the analyte sensor.

15. A system for monitoring an analyte in a host, the system comprising:
an analyte sensor comprising one or more electrodes that are adapted to gather information related to a level of the analyte in the host; and
sensor electronics circuitry mechanically and electrically coupled to the analyte sensor before the analyte sensor is implanted into the host, wherein:
the sensor electronics circuitry is adapted to generate an indicator using a first condition and a measurement of an electrical signal passed between at least two of the one or more electrodes;
the first condition comprises a threshold value indicative of implantation of the analyte sensor into the host;
the sensor electronics circuitry is further adapted to cause the system to enter an active state in response to the sensor electronics circuitry generating a confirmation of the indicator using a second condition and the information related to the level of the analyte in the host; and
the second condition comprises the level of the analyte in the host exceeding a threshold value.

16. The system of claim 15, wherein the sensor electronics circuitry is further adapted to use the measurement of the electrical signal passed between the at least two of the one or more electrodes to determine one or more of an impedance, capacitance, voltage, and current associated with the one or more electrodes.

17. A system for monitoring an analyte in a host, the system comprising:
analyte sensor electronics circuitry;
an analyte sensor that is mechanically and electrically coupled to the analyte sensor electronics circuitry before the analyte sensor is implanted into the host; and
an activation detection circuit coupled to the analyte sensor and adapted to generate a control signal operable to cause the analyte sensor to obtain information related to a level of the analyte in the host, wherein:
the control signal is generated in response to an electrical signal indicating that a first condition is satisfied;
the first condition comprises a threshold value indicative of implantation of the analyte sensor into the host;
the analyte sensor electronics circuitry is adapted to cause the system to change states if the level of the analyte in the host satisfies a second condition and if the electrical signal indicates that the first condition is satisfied; and
the second condition comprises the level of the analyte in the host exceeding another threshold value.

18. The system of claim 17, wherein the electrical signal indicating that the first condition is satisfied is generated using one or more of:
a detected proximity between the analyte sensor electronics circuitry and a reference object;
a temperature monitored by the analyte sensor electronics circuitry;
an output of an accelerometer of the analyte sensor electronics circuitry;
a response generated using wireless signaling transmitted or received by the analyte sensor electronics circuitry;
a detected change in air pressure measured by the analyte sensor electronics circuitry;
audio information monitored by the analyte sensor electronics circuitry;
a signal generated by the analyte sensor electronics circuitry in response to photons detected by the analyte sensor electronics circuitry;
a conductivity measured between two terminals of the analyte sensor electronics circuitry;
a mechanical switch located on or within a housing of the analyte sensor electronics circuitry;
a component adapted to change a connection between two conductive elements of the analyte sensor electronics circuitry, in response to movement of the component; and
a measured strain.

19. A system for monitoring an analyte in a host, the system comprising:
analyte sensor electronics circuitry;
an analyte sensor adapted to be coupled to the analyte sensor electronics circuitry before the analyte sensor is implanted into the host; and
an activation detection circuit coupled to the analyte sensor and adapted to monitor a secondary sensor according to a sampling frequency and to increase the sampling frequency in response to a first event detected using the secondary sensor;
wherein the activation detection circuit is further adapted to monitor the secondary sensor according to the increased sampling frequency and to generate a control signal in response to detecting a second event, wherein the control signal is operable to cause the analyte sensor to make a measurement for obtaining information indicative of a level of the analyte in the host when the analyte sensor is implanted in the host; and
wherein the analyte sensor electronics circuitry is further adapted to cause the system to change states in response to the information indicative of the level of the analyte in the host satisfying a condition, and further in response to the activation detection circuit detecting the second event, wherein the condition comprises the level of the analyte in the host exceeding a threshold value.

20. The system of claim 19, wherein the system is configured such that the sampling frequency is set according to a classification of one or more of the first event and the second event as determined by an activation detection component.

\* \* \* \* \*